United States Patent [19]

Scheller

[11] Patent Number: 5,693,476
[45] Date of Patent: Dec. 2, 1997

[54] METHODS OF SCREENING FOR COMPOUNDS CAPABLE OF MODULATING VESICULAR RELEASE

[75] Inventor: Richard H. Scheller, Palo Alto, Calif.

[73] Assignee: The Board of Trustees of the Leland Stanford Junior University, Stanford, Calif.

[21] Appl. No.: 393,985

[22] Filed: Feb. 24, 1995

[51] Int. Cl.[6] .................. G01N 33/53; G01N 33/567; G01N 33/543
[52] U.S. Cl. .................. 435/7.1; 435/7.2; 435/7.8; 435/7.92; 435/973; 436/518; 530/839
[58] Field of Search ............... 435/7.1, 7.2, 7.8, 435/7.92, 973; 436/518; 530/839

[56] References Cited

PUBLICATIONS

Bennett, M.K., and R.H. Scheller, "A Molecular Description of Synaptic Vesicle Membrane Trafficking," *Annu. Rev. Biochem.* 63: 63–100 (1994).
Bennett, M.K., et al., "The Syntaxin Family of Vesicular Transport Receptors," *Cell* 74: 863–873 (1993).
Bennett, M.K., and R.H. Scheller, "The molecular machinery for secretion is conserved from yeast to neurons," *Proc. Natl. Acad. Sci. USA* 90: 2559–2563 (1993).
Brommert, K., et al., "Inhibition of neurotransmitter release by C2–domain peptides implicates synaptotagmin in exocytosis," *Nature* 363: 163–165 (1993).
Calakos, N., et al., "Protein–Protein Interactions Contributing to the Specificity of Intracellular Vesicular Trafficking," *Science* 263: 1146–1149 (1994).
Chapman, E.R., et al., "SNAP–25, a t–SNARE Which Binds to Both Syntaxin and Synaptobrevin via Domains That May Form Coiled Coils," *J. Biol. Chem.* 269(44): 27427–27432 (1994).
DeBello, W.M., et al., "SNAP–mediated protein–protein interactions essential for neurotransmitter release," *Nature* 373: 626–630 (1995).

Garcia, E.P., et al., "A rat brain Sec1 homologue related to Rop and UNC18 interacts with syntaxin," *Proc. Natl. Acad. Sci. USA* 91: 2003–2007 (1994).
Hata, Y., et al., "Synaptic vesicle fusion complex contains unc–18 homologue bound to syntaxin," *Nature* 366: 347–351 (1993).
Hayashi, T., et al., "Synaptic vesicle membrane fusion complex: action of clostridial neurotoxins on assembly," *The EMBO Journal* 13(21): 5051–5061 (1994).
Hodel, A., et al., "In Chromaffin Cells, the Mammalian Sec1p Homologue Is a Syntaxin 1A–binding Protein Associated with Chromaffin Granules," *J. Biol. Chem.* 269(12): 8623–8626 (1994).
O'Conner, V., et al., "Synaptic Vesicle Exocytosis: Molecules and Models," *Cell* 76: 785–787 (1994).
Pevsner, J., et al., "Specificity and Regulation of a Synaptic Vesicle Docking Complex," *Neuron* 13: 353–361 (1994).
Pevsner, J., et al., "n–Sec1: A neural–specific syntaxin–binding protein," *Proc. Natl. Acad. Sci. USA* 91: 1445–1449 (1994).
Rothman, J., "Mechanisms of intracellular protein transport," *Nature* 372: 55–63 (1994).
Söllner, T., et al., "A Protein Assembly–Disassembly Pathway In Vitro That May Correspond to Sequential Steps of Synaptic Vesicle Docking, Activation, and Fusion," *Cell* 75: 409–418 (1993).
Söllner, T., et al., "SNAP receptors implicated in vesicle targeting and fusion," *Nature* 362: 318–324 (1993).
Warren, G., "Bridging the gap," *Nature* 362: 297–298 (1993).
Whiteheart, S.W., et al., "SNAP family of NSF attachment proteins includes a brain–specific isoform," *Nature* 362: 353–355 (1993).

*Primary Examiner*—Ponnathapura Achutamurthy
*Attorney, Agent, or Firm*—Charles K. Sholtz; Peter J. Dehlinger

[57] ABSTRACT

Methods of identifying compounds capable of affecting binding of a SNAP-25, α-SNAP, n-sec1 or VAMP to syntaxin are disclosed. Compounds identified by such methods are useful for modulating vesicular release, such as release at neural synapses.

15 Claims, 12 Drawing Sheets

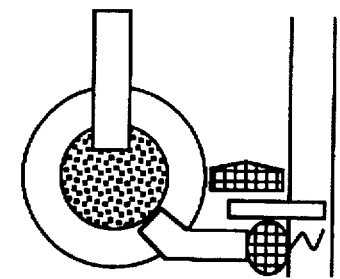
Fig. 1A
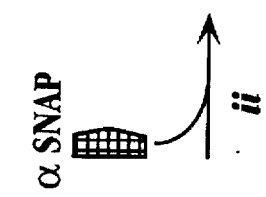
Fig. 1B
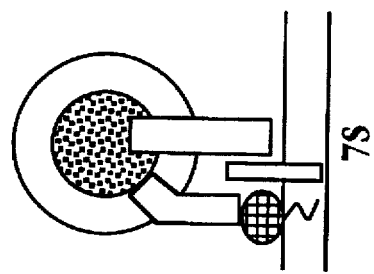
Fig. 1C
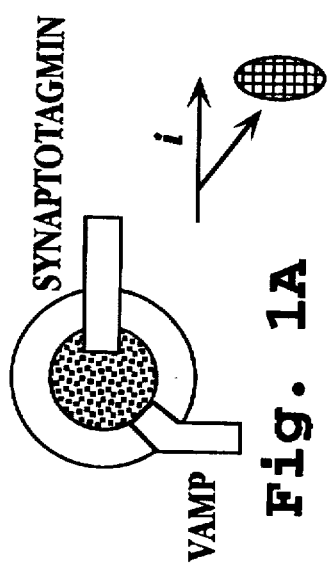
Fig. 1D
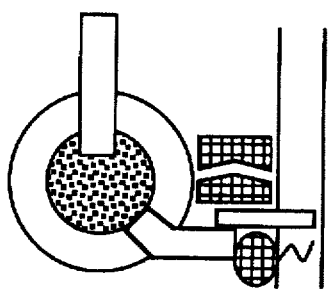
Fig. 1E
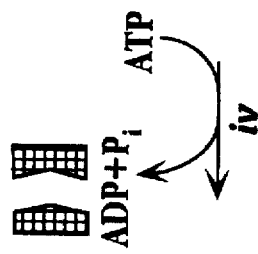
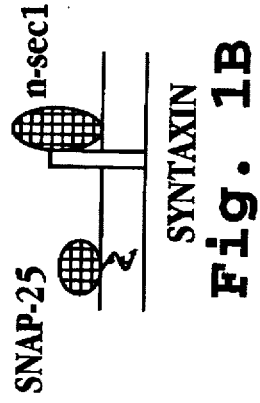
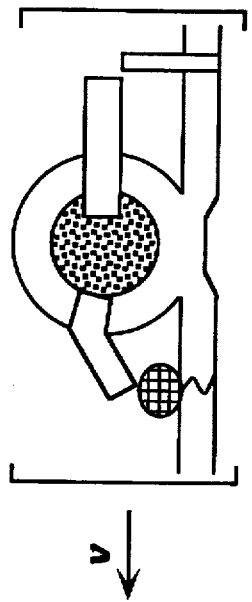
Fig. 1F
Fig. 1G

GST Fusion Protein

↓ Bind to bead

↓ Add ⊘

↓ Wash unbound

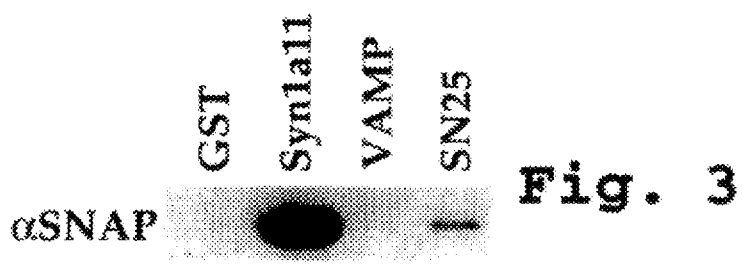
Fig. 3
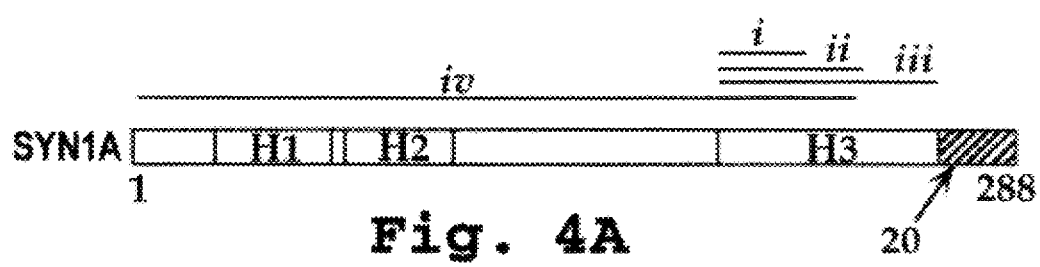
Fig. 4A
Fig. 4B

|       | i<br>SN25 | ii<br>αSNAP | iii<br>VAMP | iv<br>n-sec1 |
|-------|-----------|-------------|-------------|--------------|
| 1A4   |           |             |             |              |
| 1A5   |           |             |             |              |
| 1A6   |           |             |             |              |
| 1A13  |           |             |             |              |
| 1A17  |           |             |             |              |
| 1A11  |           |             |             |              |
| 1A9   |           |             |             |              |
| 1A16  |           |             |             |              |
| 1A12  |           |             |             |              |

Fig. 4C

| EcoRI/RBS | 6xHis |
|---|---|
| ATGAGAGGATCG | |

SEQ ID NO: 34

| | BamHI | SalI | PstI | HindIII | |
|---|---|---|---|---|---|
| | GGATCCGTGACCTGCAGCCAAGCTT | | | | AATTAGCTGAG |

SEQ ID NO: 35

METHODS OF SCREENING FOR COMPOUNDS CAPABLE OF MODULATING VESICULAR RELEASE

This work was supported in part by NIMH Grants 2R01 MH38710-09 and 5p50 MH48108-04. Accordingly, the United States Government has certain rights in this invention.

FIELD OF THE INVENTION

The present invention relates to methods of identifying compounds capable of modulating vesicular release.

REFERENCES

Aalto, M. K., et al., *EMBO J.* 12:4095–4104 (1993).

Ausubel, F. M., et al., *Current Protocols in Molecular Biology* (John Wiley and Sons, Inc., Media, Pa.).

Barbas, C. F., et al., *Proc. Natl. Acad. Sci. USA* 89(10):4457 (1992).

Bartel, P., et al., *BioTechniques* 14:920–924 (1993).

Bennett, M. K., et al., *Science* 257:255 (1992).

Bennett, M. K., et al., *J. Neurosci.* 13:1701 (1993a).

Bennett, M. K., et al., *Cell* 74:863 (1993b).

Bennett, M. K., and Scheller, R. H., *Proc. Natl. Acad. Sci. USA* 90:2559–2563 (1993).

Bennett, M. K., and Scheller, R. H., *Annu. Rev. Biochem.* 63:63–100 (1994).

Brent, R., et al., *Cell,* 43:729–736 (1985).

Bittner, M. A., and Holz, R. W., *J. Biol. Chem.* 267:16226 (1992).

Bunin, B. A. and Ellman, J. A., *J. Am. Chem. Soc.* 114:10997 (1992).

Bunin, B. A., et al., *Proc. Natl. Acad. Sci. USA* 91:4708 (1994).

Calabrese, G. S., et al., *Anal. Chem.* 59:833–837 (1987).

Calakos, N., et al., *Science* 263:831–844 (1994).

Chapman, E. R., et al., *J. Biol. Chem.* 269:27427–27432 (1993).

Chien, C.-t, et al., *Proc. Natl. Acad. Sci. U.S.A.,* 88:9578 (1991).

Chomczynski, P., and Sacchi, N., *Anal. Biochem.* 162:156–159 (1987).

Corsel, J. W., et al., *J. Colloid. Interface Sci.* 111:544–554 (1986).

Cullen, D. C., et al., *Biosensors* 3:211–225 (1988).

DiAntonio, A., and Schwarz, T. L., *Neuron* 12:909–920 (1994).

Dooley, C. T., et al., *Proc. Natl. Acad. Sci. USA* 90(22):10822 (1993a).

Dooley, C. T., et al., *Life Sci.* 52(18):1509 (1993b).

Durfee, T., et al., *Genes & Development* 7:555 (1993).

Ecker, D. J., et al., *Nuc. Acids Res.* 21(8):1853 (1993).

Edelmann, L., et al., *EMBO J.* 14:224 (1995).

Eichler, J., et al., *Biochemistry* 32(41):11035 (1993).

Elferink, L. A., et al., *Cell* 72:153 (1993).

Fields, S., et al., *Nature* 340:245 (1989).

Furka, A., et al., *Int. J. Pept. Protein Res.* 37:487–493 (1991).

Geppert, M., et al., *Cell* 79:717–727 (1994).

Guan, K. L. and Dixon, J. E., *Anal. Biochem.* 192:262 (1991).

Gyuris J., et al., *Cell,* 75:791–803 (1993).

Hardwick, K. G., and Pelham, H. R. B., *J. Cell Biol.* 119:513–521 (1992).

Harlow, E., et al., *ANTIBODIES: A LABORATORY MANUAL,* Cold Spring Harbor Laboratory Press (1988).

Hayashi, T., et al., *EMBO J.* 13:5051–5061 (1994).

Houghten, R. A., *Proc. Natl. Acad. Sci. USA* 85:5131–5135 (1985).

Houghten, R. A., et al., *BioTechniques* 4:522–528 (1986).

Houghten, R. A., et al., *Nature* 354:84–86 (1991).

Houghten, R. A., et al., *BioTechniques* 13:412–421 (1992).

Houghten, R. A., *Current Biology* 4:564 (1994).

Inoue, A., et al., *J. Biol. Chem.* 267:10613–10619 (1992).

Jahn, R., and Südhof, T. C., *Annu. Rev. Neurosci.* 17:219–246 (1994).

Johnsson, B., et al., *Anal. Biochem.* 198:268 (1991).

Jönsson, U., et al., *Colloids Surfaces* 13:333–339 (1985).

Kramer, A., et al., *Pept. Res.* 6(6):314 (1993).

Lam, K. S., et al., *Nature* (London) 354:82–84 (1991).

Lam, K. S., et al., *Bioorg. Med. Chem. Lett.* 3:419–424 (1993).

Liedberg, B., et al., *Z. Phys.* 4:299–304 (1983).

Mullis, K. B., U.S. Pat. No. 4,683,202, issued 28 Jul. 1987.

Mullis, K. B., et al., U.S. Pat. No. 4,683,195, issued 28 Jul. 1987.

Nellen, Ph. M., and Lukosz, W., *Sensors Actuators* B1:592–596 (1990).

Ngeh-Ngwainbi, J., et al., *Biosens. Bioelectronics* 5:13–26 (1990).

Ngo, T. T., Ed. in *ELECTROCHEMICAL SENSORS IN IMMUNOLOGICAL ANALYSIS* (Plenum Press, New York, N.Y.) (1987).

Niemann, H., et al., *Trends in Cell Biol.* 4:179–185 (1994).

Nonet, M. L., et al., *Cell* 73:1291–1305 (1993).

Ohlmayer, M. H., et al., *Proc Nat Acad Sci, USA,* 90(23):10922 (1993).

O'Shannessy, D. J., et al., *Anal. Biochem.* 212:457 (1993).

Oyler, G. A., et al., *J. Cell Biol.* 109:3039–3052 (1989).

Oyler, G. A., et al., *Dev. Brain Res.* 65:133 (1992).

Pevsner, J., et al., *Neuron* 13:353–361 (1994a).

Pevsner, J., et al., *Proc. Natl. Acad. Sci. USA* 91:1445–1449 (1994b).

Pinilla, C., et al., *Biotechniques* 13(6):901 (1992).

Pinilla, C., et al., *Gene* 128(1):71 (1993).

Rajakovic, L., et al., *Anal. Chim. Acta* 217:f111–121 (1989).

Roederer, J. E., and Bastiaans, G. J., *Anal. Chem.* 55:2333–2336 (1983).

Rothman, J. E., *Nature* 372:55–63 (1994).

Sambrook, J., et al., *MOLECULAR CLONING: A LABORATORY MANUAL,* Second Edition, Cold Spring Harbor Laboratory (Cold Spring Harbor, N.Y.) (1989).

Schiavo, G., et al., *Trends in Microbiology* 1:170–174 (1993).

Sebestyen, F., et al., *Bioorg. Med. Chem. Lett.* 3:413–418 (1993).

Smith, D. B. and Johnson, K. S., *Gene* 67:31 (1988).

Sogaard, M., et al., *Cell* 78:937–948 (1994).

Söllner, T., et al., *Cell* 75:409–418 (1993a).

Söllner, T., et al., *Nature* 362:318–324 (1993b).

Thomas, P., et al., *Neuron* 11:93 (1993).

Trimble, W., et al., *J. Neurosci.* 10:1380 (1990).

Virgilio, A. A. and Ellman, J .A., *J. Am. Chem. Soc.* 116:11580 (1994).

Vroman, L., and Adams, A. L., *Surface Sci.* 16:438–446 (1969).

Ward, M. D., and Buttry, D. A., *Science* 249:1000–1007 (1990).

Whiteheart, S. W., et al., *Nature* 362:353 (1993).

Wilson, D. W., et al., *J. Cell Biol.* 117:531–538 (1992).

Yang, X., et al., *Science* 257:680 (1992).

Zuckermann, R. N., et al., *Int. J. Pept. Protein Res.* 40:498–507 (1992).

BACKGROUND OF THE INVENTION

Signal transmission between nerve cells typically involves the release of neurotransmitter from a presynaptic cell onto a postsynaptic cell. The neurotransmitter in the presynaptic cell is contained in synaptic vesicles positioned above the release sites at the presynaptic membrane (active zones). In response to a release signal (typically a local influx of calcium due to a depolarization of the presynaptic terminal), the vesicles undergo a series of mobilization steps culminating in the fusion of the vesicles with the presynaptic terminal membrane, and a dumping of vesicle contents into the synaptic cleft.

The neurotransmitter molecules diffuse across the synaptic cleft and bind to corresponding receptors in the postsynaptic membrane to communicate the appropriate signal (typically a depolarization or hyperpolarization of the postsynaptic membrane) to the postsynaptic cell. Much of the neurotransmitter in the synapse is subsequently re-absorbed by the presynaptic cell through specific transmitter uptake mechanisms.

A number of drugs affecting signalling in the central nervous system (CNS) and the peripheral nervous system (PNS) have been developed. Some of these, such as phenoxybenzamine, block specific post-synaptic receptors; others, such as clonidine and diethylamide, stimulate such receptors; still others (e.g., desipramine, imipramine) act on reuptake mechanisms, and some act on neurotransmitter synthesis (e.g., α-Methyltyrosine, p-Chlorophenylalanine) or degradation (e.g., monoamine oxidase inhibitors, iproniazid, pargyline).

The present invention provides a tool for the screening and identification of drugs capable of affecting neurotransmitter release at the active zones of presynaptic membranes.

SUMMARY OF THE INVENTION

In one aspect, the present invention includes a method of identifying a compound capable of affecting binding of a SNAP-25 (synaptosomal-associated protein of 25 kDa), α-SNAP (soluble NSF attachment protein, where "NSF" is N-ethylmaleimide-sensitive factor), n-sec1 or VAMP (vesicle-associated membrane protein) syntaxin-binding protein (SBP) to syntaxin. The method includes (i) contacting such an SBP with a corresponding binding-protein binding site (BPBS) from a region of the syntaxin protein, in the presence and absence of a test compound, (ii) measuring the effect of the test compound on the extent of binding between the SBP and the BPBS, and (iii) identifying the compound as effective if its measured effect on the extent of binding is above a threshold level.

The syntaxin is preferably syntaxin 1A. When the SBP is SNAP-25, the BPBS is contained in a fragment corresponding to the region of syntaxin 1A defined by SEQ ID NO:21. When the SBP is α-SNAP, the BPBS is contained in a fragment corresponding to the region of syntaxin 1A defined by SEQ ID NO:20. When the SBP is VAMP, the BPBS is contained in a fragment corresponding to the region of syntaxin 1A defined by SEQ ID NO:19. When the SBP is n-sec1, the BPBS is contained in a fragment corresponding to the region of syntaxin 1A between amino acids 4 and 240.

In one embodiment, the test compound is effective to inhibit binding between the SBP and the BPBS, and in a related embodiment, the test compound is effective to displace the SBP from the BPBS. In another embodiment, the test compound is effective to potentiate or enhance the binding between the SBP and the BPBS. The contacting may include contacting an SBP that is immobilized on a solid support, or it may include contacting a BPBS that is immobilized on a solid support.

The test compound may be a small molecule, macromolecule or peptide, such as one of a plurality of small molecules in a small molecule combinatorial library, or one of a plurality of peptides in a peptide combinatorial library.

These and other objects and features of the invention will become more fully apparent when the following detailed description is read in conjunction with the accompanying drawings.

BRIEF DESCRIPTION OF THE FIGURES

FIGS. 1A, 1B, 1C, 1D, 1E, 1F and 1G are simplified schematic diagrams of steps involved in vesicle mobilization and show the roles and interactions of proteins associated with vesicle docking and release.

FIG. 3 is a computer-operated image of a Western blot showing the binding of soluble NSF attachment protein (α-SNAP) to immobilized GST, syntaxin 1A, vesicle-associated membrane protein (VAMP) and synaptosomal-associated protein of 25 kDa (SNAP-25).

FIGS. 4A, 4B and 4C show data on the binding of VAMP, α-SNAP, SNAP-25 and n-sec1 to a set of syntaxin deletion mutants. FIG. 4A is a schematic of the syntaxin 1A polypeptide (SYN1A), along with a summary of regions important for binding of (i) SNAP-25, (ii) α-SNAP, (iii) VAMP and (iv) n-sec1. FIG. 4B shows the extent of the deletion mutants relative to the schematic in FIG. 4A. FIG. 4C presents a computer-generator image of a Western blot showing the degree of binding of the four ligands, SNAP-25, α-SNAP, VAMP and n-sec1 to each of the syntaxin deletion mutants.

BRIEF DESCRIPTION OF THE SEQUENCES

Figure 2A:
FIGS. 2A, 2B, 2C and 2D are schematic diagrams of a protein binding assay employing a fusion protein linked, through a glutathione-S-transferase (GST) moiety at its N-terminal, to glutathione agarose beads.

SEQ ID NO:1 is the nucleotide sequence of rat syntaxin 1A 3' end, encoding amino acids 4–288 (GenBank M95734).

SEQ ID NO:2 is the predicted amino acid sequence of SEQ ID NO:1.

SEQ ID NO:3 is the nucleotide sequence of rat syntaxin 1B (GenBank M95735).

SEQ ID NO:4 is the predicted amino acid sequence of SEQ ID NO:3.

SEQ ID NO:5 is the nucleotide sequence of rat syntaxin 2 (GenBank L20823).

SEQ ID NO:6 is the predicted amino acid sequence of SEQ ID NO:5.

SEQ ID NO:7 is the nucleotide sequence of rat syntaxin 3 (GenBank L20820).

SEQ ID NO:8 is the predicted amino acid sequence of SEQ ID NO:7.

SEQ ID NO:9 is the nucleotide sequence of rat syntaxin 4 (GenBank L20821).

SEQ ID NO:10 is the predicted amino acid sequence of SEQ ID NO:9.

SEQ ID NO:11 is the nucleotide sequence of rat syntaxin 5 (GenBank L20822).

SEQ ID NO:12 is the predicted amino acid sequence of SEQ ID NO:11.

SEQ ID NO:13 is the nucleotide sequence of rat VAMP-1 (GenBank M24104).

SEQ ID NO:14 is the predicted amino acid sequence of SEQ ID NO:13.

SEQ ID NO:15 is the nucleotide sequence of rat VAMP-2 (GenBank M24105).

SEQ ID NO:16 is the predicted amino acid sequence of SEQ ID NO:15.

SEQ ID NO:17 is the nucleotide sequence of mouse SNAP-25 (GenBank M22012).

SEQ ID NO:18 is the predicted amino acid sequence of SEQ ID NO:17.

SEQ ID NO:19 is the amino acid sequence of the region of Syn1A between amino acid positions 191 and 266 (H3 region).

SEQ ID NO:20 is the amino acid sequence of the region of Syn1A between amino acids 191 and 240.

SEQ ID NO:21 is the amino acid sequence of the region of Syn1A between amino acids 191 and 221.

SEQ ID NO:22 is the nucleotide sequence encoding the cytoplasmic domain of rat syntaxin 1A (amino acids 4–266; Syn1A11).

SEQ ID NO:23 is the predicted amino acid sequence of SEQ ID NO:22.

SEQ ID NO:24 is the amino acid sequence of a fragment at the amino terminus of the VAMP 2 recombinant protein used in surface plasmon resonance (SPR) experiments.

SEQ ID NO:25 is the amino acid sequence of the amino terminus fragment of syntaxin 1A (amino acids 4–193) used to inhibit binding of VAMP 2 to syntaxin 1A.

SEQ ID NO:26 is the nucleotide sequence of the oligonucleotide used to generate mutant M1.

SEQ ID NO:27 is the nucleotide sequence of the oligonucleotide used to generate mutant M4.

SEQ ID NO:28 is the nucleotide sequence of the oligonucleotide used to generate mutant M6.

SEQ ID NO:29 is the nucleotide sequence of the oligonucleotide used to generate mutant M2.

SEQ ID NO:30 is the nucleotide sequence of the oligonucleotide used to generate mutant M3.

SEQ ID NO:31 is the nucleotide sequence of the oligonucleotide used to generate mutant M5.

SEQ ID NO:32 is the polylinker of the pGEX-KG vector.

SEQ ID NO:33 is the amino acid sequence predicted from SEQ ID NO:32.

SEQ ID NO:34 represents a nucleotide sequence between the RBSII and 6xHis regions of pQE-9.

SEQ ID NO:35 represents a nucleotide sequence between the 6xHis and $t_O$ regions of pQE-9.

DETAILED DESCRIPTION OF THE INVENTION

I. Definitions

The term "syntaxin polynucleotide" refers to (i) the polynucleotide that encodes a full-length syntaxin, (ii) a fragment of (i) which encodes a binding protein binding site (BPBS) of syntaxin, or (iii) a polynucleotide that selectively hybridizes with a polynucleotide having a sequence represented by the complement of any of SEQ ID NO:1, SEQ ID NO:3, SEQ ID NO:5, SEQ ID NO:7, SEQ ID NO:9 and SEQ ID NO:11. Exemplary syntaxin polynucleotides have sequences presented herein as SEQ ID NO:1, SEQ ID NO:3, SEQ ID NO:5, SEQ ID NO:7, SEQ ID NO:9, SEQ ID NO:11, and SEQ ID NO:22.

The term "syntaxin" or "syntaxin polypeptide" refers to (i) a full length syntaxin polypeptide, (ii) a fragment of (i) containing a BPBS, or (iii) a polypeptide encoded by the open reading frame of a syntaxin polynucleotide. It will be appreciated that various amino acid changes, insertions, deletions, etc., may be made to a syntaxin polypeptide without substantially altering its BPBS, in particular, without substantially altering the affinity of the BPBS for the corresponding syntaxin binding protein (SBP), and that polypeptides having such changes, insertions, deletions, etc., are also included in the definition of syntaxin. Exemplary syntaxin polypeptides have sequences presented herein as SEQ ID NO:2, SEQ ID NO:4, SEQ ID NO:6, SEQ ID NO:8, SEQ ID NO:10, SEQ ID NO:12, SEQ ID NO:19, SEQ ID NO:20, SEQ ID NO:21, and SEQ ID NO:23.

II. Syntaxin in Synaptic Transmission

A. Model of Synaptic Transmission

Synaptic transmission in the brain proceeds through a series of vesicle mobilization steps involving specific proteins. Many of these steps and proteins are similar to those involved in other types of secretion in mammals and in other species, including yeast. FIGS. 1A–1G illustrate a series of vesicle mobilization steps (i–v) and the corresponding protein complexes consistent with the studies carried out in support of the present invention. Additional experimental support for these steps and the roles of the specific proteins are comprehensively reviewed, for example, in Bennett and Scheller (1994) and Jahn and Södhof.

Vesicles at a synapse typically appear in vesicle arrays near active zones (sites of vesicle release). FIG. 1A shows one such vesicle positioned above the presynaptic membrane (FIG. 1B). The vesicle contains VAMP (vesicle-associated membrane protein) and synaptotagmin, while the presynaptic membrane contains SNAP-25 (synaptosomal-associated protein of 25 kDa) and syntaxin.

The targeting of a vesicle to the appropriate acceptor membrane occurs through the formation of a 7S complex (FIG. 1C) which is comprised of the two vesicle proteins, VAMP and synaptotagmin, along with the two target membrane proteins, SNAP-25 and syntaxin. These four proteins co-migrate on glycerol gradients and co-precipitate from detergent solubilized brain extracts (Söllner, et al., 1993a).

Studies with recombinant VAMP, SNAP-25 and syntaxin demonstrate that all three proteins specifically bind one another in the micro-molar range. The SNAP-25/syntaxin 1A complex, however, forms a higher affinity binding site for VAMP, making the heterotrimeric complex considerably more stable than any of the individual paired interactions (Pevsner, et al., 1994a; Hayashi, et al.). Formation of the stable trimeric complex is specific for syntaxin 1, not syntaxin 2, 3 or 4, suggesting that at least a component of the specificity for vesicle targeting is achieved through these protein-protein interactions (Pevsner, et al., 1994a).

The synaptic vesicle protein, VAMP (also referred to as synaptobrevin), is found associated with synaptophysin on the vesicle; however, synaptophysin is not present in the 7S complex (Calakos, et al.; Edelmann, et al.). Similarly, the soluble protein n-sec1 (also referred to as munc-18 and rb-sec1) is associated with syntaxin on the plasma membrane (FIG. 1B) but not found in the 7S complex (FIG. 1C; Pevsner, et al., 1994a).

A series of steps, that eventually lead to membrane fusion, follow the formation of the 7S particle. Initially, α-SNAP (soluble NSF attachment protein) is added to the 7S complex (step ii, FIG. 1D), followed by the binding of NSF (N-ethylmaleimide-sensitive factor; step iii, FIG. 1E) and ATP hydrolysis (step iv, FIG. 1F; Söllner, et al., 1993a). The addition of recombinant α-SNAP to detergent extracts of brain followed by immunoprecipitation with syntaxin antibodies showed that as α-SNAP associates with the 7S complex there is a corresponding dissociation of synaptotagmin (step ii, FIGS. 1C, 1D). NSF associates with the complex only after α-SNAP has bound, forming a 20S particle (step iii, FIG. 1E). To form a stable 20S complex, a non-hydrolyzable form of ATP must be bound to NSF. While the precise stoichiometry of the components in this complex is not known, it is thought that a single molecule of VAMP, syntaxin and SNAP-25 associate with multiple copies of α-SNAP and NSF. Upon ATP hydrolysis by NSF, the 20S complex dissociates into its component subunits (step iv, FIG. 1F).

After the hydrolysis of ATP by NSF, several intermediate states, indicated by the brackets in FIG. 1F, may be encountered prior to membrane fusion. This conclusion arises from studies in which ATP was removed from permeabilized cells or the $Mg^{++}$ required for ATP hydrolysis was chelated. Transitions between three of these intermediates are sensitive to temperature, pH, $Ca^{++}$ ions (Thomas, et al., and Bittner and Holz).

While an influx of calcium is the physiological trigger for vesicle fusion, or "fast" exocytosis, there is not presently a consensus in the literature as to the identity of the calcium sensor protein. This uncertainty does not, however, affect the general steps outlined in FIGS. 1A–1G or the methods and compositions of the present invention.

Results of experiments performed in support of the present invention indicate that three multimeric complexes of the protein syntaxin are important in neurotransmitter secretion: (i) syntaxin and n-sec1 (FIG. 1B); (ii) syntaxin, VAMP and SNAP-25 (FIG. 1C; 7S complex); and (iii) syntaxin, VAMP, SNAP-25, α-SNAP and NSF (FIG. 1E; 20S complex). The results demonstrate that unique, overlapping, domains of syntaxin are required to form these complexes. Further, the results demonstrate that the formation of higher-order heteromultimers has a distinct set of structural requirements from those required for dimeric interactions between any two interacting proteins. For example, dissociation of the 20S complex by NSF following ATP hydrolysis requires amino terminal regions of syntaxin which are outside of the binding domains for the 20S constituent proteins. These data are consistent with a model whereby conformational changes in syntaxin, resulting from protein-protein interactions and ATP hydrolysis by NSF, mediate vesicle docking and fusion.

B. Localization of Binding Regions on Syntaxin

Experiments performed in support of the present invention have localized the binding sites for the syntaxin binding proteins (SBPs) SNAP-25 (SN25), α-SNAP, VAMP 2 and n-sec1 on the syntaxin 1A protein. These binding sites are termed herein "binding protein binding sites" (BPBSs). The binding site localizations were performed using protein-protein binding assays ("partner-capture assays") and syntaxin deletion mutants as detailed in the Materials and Methods section, and Examples 1 and 2, below.

Figure 2B:
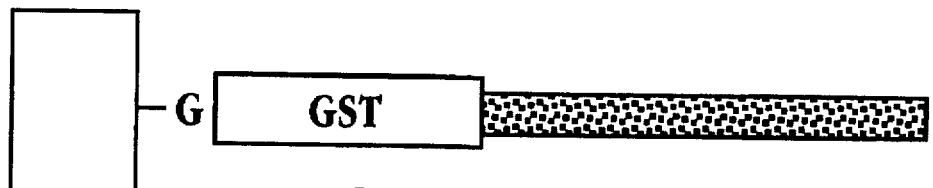

The proteins used in the assays were produced in bacteria as fusions between glutathione-S-transferase (GST) and the recombinant protein. Bacterial cell lysates were prepared and passed over agarose beads derivatized with glutathione as described below. This resulted in the attachment of the GST portions of the fusions to the glutathione on the agarose beads (as shown in FIG. 2B). In the assays, the "immobilized" protein was left attached to the beads, while the "free" protein was cleaved from the beads with thrombin as described below.

Figure 2C:
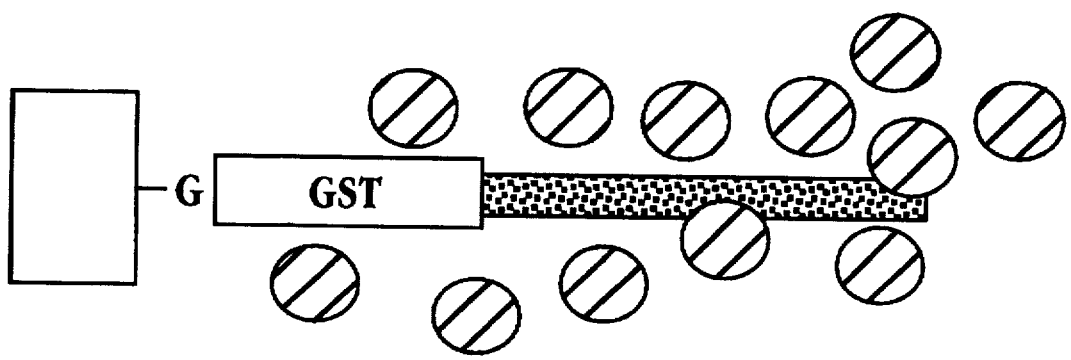
Figure 2D:
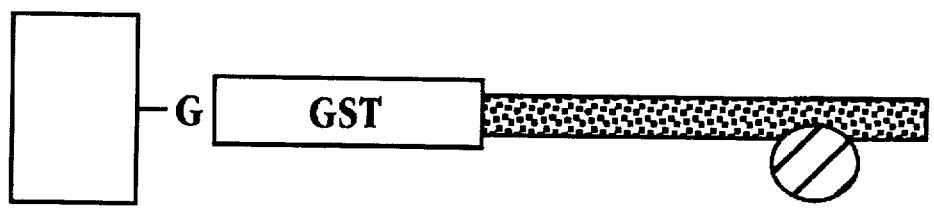

The binding assay, illustrated in FIGS. 2A, 2B, 2C and 2D, was designed to measure the binding between two interacting proteins (typically syntaxin or a syntaxin mutant and one the following: α-SNAP, SNAP-25, VAMP or n-sec1). One of the proteins (FIG. 2A) was immobilized to agarose beads (FIG. 2B), and the other ("free") protein was passed over the beads containing the immobilized protein (FIG. 2C). Unbound free protein was washed off, and free protein that bound to the immobilized protein (FIG. 2D) was detected using an antibody directed against the free protein.

Experiments performed in support of the present invention employed a binding assay such as is described above to identify regions of the syntaxin molecule necessary to bind various SBPs, such as SNAP-25, α-SNAP, VAMP and n-sec1. The first set of experiments employed the above assay to detect the binding of one such SBP, free α-SNAP, to GST fusion proteins containing either syntaxin 1A, VAMP, or SNAP-25, as described in Example 1A. The binding of syntaxin was detected using a Western blot probed with anti-α-SNAP antibodies.

Exemplary results from this binding assay are presented in FIG. 3. A strong signal was observed for the binding of α-SNAP to syntaxin, with a weaker but significant signal for the binding of α-SNAP to SNAP-25. No α-SNAP binding to VAMP was observed. These data suggest that multiple α-SNAP proteins can be added to the 20S complex through independent binding sites on SNAP-25 and syntaxin.

1. Deletion Mutant Analysis. Regions on syntaxin (BPBSs) required for its binding to n-sec1, VAMP, SNAP-25 and α-SNAP were identified using a series of syntaxin 1A deletion mutants (FIG. 4B), constructed as described in the Materials and Methods and Table 1. The constructs were expressed in bacteria, and fusion proteins purified using glutathione columns were used in binding assays such as described above and in FIG. 2. Each of the syntaxin deletion constructs produced a protein which migrated at the expected molecular weight when analyzed by SDS polyacrylamide gel electrophoresis (SDS-PAGE). Recombinant VAMP, SNAP-25, α-SNAP and n-sec1, produced as described in the Materials and Methods section, were used as ligands to study their binding to the various syntaxin deletions.

Binding was assayed as described in Materials and Methods and Example 1B. The GST-syntaxin deletion fusion proteins, immobilized on glutathione beads, were incubated with the ligands, washed, denatured and fractionated by SDS-PAGE. Bound ligand protein (n-sec1, VAMP, SNAP-25 or α-SNAP) was detected by Western blotting (Materials and Methods, Example 1B, FIG. 4C).

The results of the analyses are summarized in FIG. 4A. The full-length syntaxin, either with (amino acids 8–288; Syn 1A) or without (amino acids 4–266; Syn 1A11) the membrane anchor, bound to n-sec1, VAMP, SNAP-25 and α-SNAP. As the protein was deleted from the carboxyl terminal end, a progressive loss of binding sites was observed. For example, deletion of amino acids 241–266 (Syn 1A17) resulted in the loss of VAMP binding. Similarly, deletion of the next amino terminal domain, corresponding to amino acids 222–240 (Syn 1A13), resulted in a loss of α-SNAP and n-sec1 binding. Loss of amino acids 191–221 (Syn 1A6) eliminated all binding, as did further upstream deletions from the carboxyl terminal end of syntaxin (Syn 1A4 and Syn 1A5).

The region of syntaxin adjacent the membrane anchor (amino acids 191–266) was necessary and sufficient for the binding of VAMP, SNAP-25 and α-SNAP, but was not sufficient (though still necessary) to bind n-sec1 in the absence of upstream regions. Similarly, regions upstream of H3 were necessary but not sufficient to bind n-sec1. Accordingly, these data define four overlapping binding sites or domains. SNAP-25 binding requires amino acids 191–221 (SEQ ID NO:21), α-SNAP binding requires amino acids 191–240 (SEQ ID NO:20), VAMP binding requires amino acids 191–266 (SEQ ID NO:19), and n-sec1 binding requires amino acids 4–240 of the syntaxin 1A sequence. With the exception of the n-sec1 binding domain, all of the binding sites are encompassed by the H3 domain (SEQ ID NO:19) of syntaxin (FIG. 4A). This domain is highly conserved with respect to syntaxin homologues in species as distant as yeast (e.g., sso1p from *Saccharomyces cerevisiae*; Aalto et al., 1993), and is predicted to be a helical region capable of protein-protein interaction through its coiled-coil motif (Hardwick and Pelham, 1992). VAMP, α-SNAP and SNAP-25 proteins are also predicted to have helical domains, suggesting that protein-protein interaction through their respective coiled-coil motifs may mediate the binding of these proteins to syntaxin.

Regions in other syntaxins, such as syntaxin 2, 3, 4, or 5, which correspond to the BPBSs of syntaxin 1A, may be identified by aligning the amino acid sequences of syntaxin 1A with any of the other syntaxins (using, for example, the align feature of the program "MACVECTOR" (Eastman Kodak Co., New Haven, Conn.)).

Figures 5A, 5B:
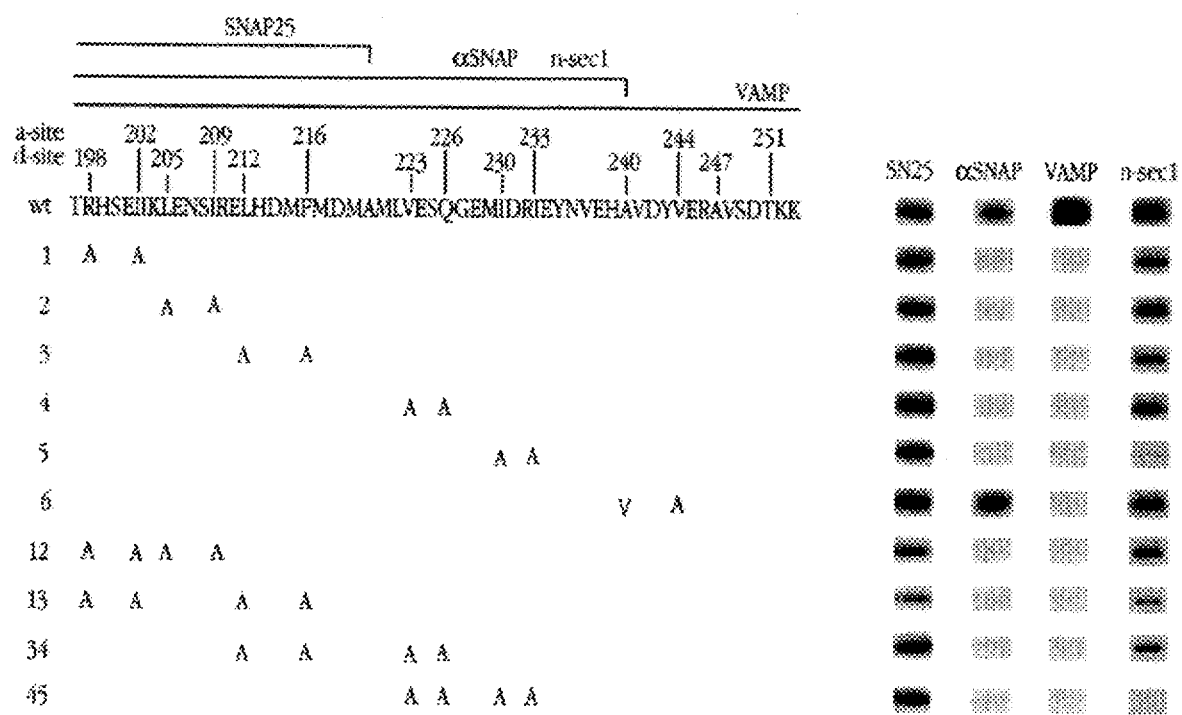
FIG. 5A shows the predicted amino acid sequences of syntaxin point deletion mutants in the H3 region of syntaxin relative to normal (unmutated) syntaxin 1A sequence (top).
FIG. 5B is a computer-generated image of a Western blot showing the binding of SNAP-25, α-SNAP, VAMP and n-sec1 to the different point mutants in FIG. 5A.

2. Point Mutation Analysis. The relative importance of selected amino acid residues in the H3 region of syntaxin 1A on binding to SBPs was assayed using site-directed, or point mutation analysis. Point mutations were generated at those locations that correspond to "a" or "d" sites in the coiled-coil model (Hardwick and Pelham, 1992). Syntaxin 1A mutants carrying mutations resulting in the alteration of two or four selected amino acid residues were constructed as described in the Materials and Methods section and Table 2. The location and identity of the amino acid changes for each mutant are summarized in FIG. 5A. The binding of SNAP-25, α-SNAP, VAMP and n-sec1 to these mutants was analyzed as described above and detailed in Example 1C. Exemplary results from one such binding assay are shown in FIG. 5B. The results indicate that none of the point mutants completely eliminated the binding of SNAP-25 to syntaxin. In two of the constructs (mutants 12 & 13), however, the level of binding was significantly reduced. These constructs contained four point mutations within the domain determined to be required for SNAP-25 binding to syntaxin by deletion analysis.

In contrast to the results presented for SNAP-25, all of the point mutations eliminated the binding of VAMP to syntaxin. These results are consistent with the observation that the entire H3 region was required for binding VAMP. Thus, VAMP binding to syntaxin may be more sensitive to the conformation of the H3 region and the amino acid sequence at the "a" and/or "d" sites of the helix, while SNAP-25 binding may be comparatively insensitive to these same structural features.

A more complex pattern was observed for α-SNAP binding to the mutant syntaxins. In all mutant constructs except for mutant 6, α-SNAP binding was eliminated. The observation that binding was not affected in mutant 6 was not surprising, since the amino acid changes lie outside of the syntaxin binding site for α-SNAP as determined from the deletion analysis. The association of n-sec1 with syntaxin was particularly sensitive to mutations at positions 223, 226, 230 and 233 (mutants 5 and 45). Overall, the binding profile suggested that amino acids between 212 and 233 are important for the binding of syntaxin to n-sec1 (mutants 5, 13 and 45). In view of the above results, the point mutation data are consistent with the data obtained from the deletion mutant analyses, and confirm the four overlapping binding domains for VAMP, SNAP-25, α-SNAP and n-sec 1 on syntaxin.

Information obtained from point mutation analyses such as described above may be employed to aid in the design of compounds effective to alter or effect the binding of an SBP to a BPBS. For example, the structure of a native fragment and a mutant, non-binding fragment of syntaxin may be determined (using, for example, NMR or X-ray crystallography), and the difference in structure due to the mutant amino acid(s) ascertained. This information may then be used to select classes of test compounds for screening in, e.g., one of the test compound screening assays described below.

3. Formation and Dissociation of the 20S Complex. The addition of NSF, α-SNAP and non-hydrolyzable ATP to brain extracts results in the formation of a heterogeneous series of particles which migrate at about the 20S region in glycerol gradients. Analysis of these particles on SDS polyacrylamide gels suggests that multiple copies of α-SNAP and NSF may be added to the complex. To further define and characterize the binding of multiple SBPs to syntaxin, the protein-protein interactions in 20S particles were analyzed by assembling complete 20S complex particles from purified recombinant proteins as described in Example 2. The cytoplasmic domain of syntaxin was expressed as a GST fusion protein, bound to glutathione agarose beads, and combined with recombinant VAMP and SNAP-25 to form a heterotrimeric complex. Further addition of recombinant NSF and α-SNAP in the presence of non-hydrolyzable ATP (either ATPγS or ATP/EDTA) resulted in the formation of a heteropentameric complex (FIGS. 6A and 6B), indicating the purified components listed above are sufficient for the assembly of the particle with no requirement for additional accessory factors under these conditions.

When $Mg^{++}$ was added, the complex dissociated in the presence of ATP but not ATPγS. Approximately 80–90% of VAMP, 70–90% of α-SNAP and 40–80% of NSF dissociated from syntaxin following ATP hydrolysis by NSF. However, about 90% of SNAP-25 remained associated with the GST-syntaxin beads, suggesting that perhaps additional factors not otherwise associated with the 20S complex may be necessary for the disassembly of the particle.

A similar set of studies, also detailed in Example 2, was carried out using the syntaxin deletion mutants. As predicted from the experiments in Example 1, syntaxin deletions of the H3 region (constructs 1A5 and 1A6) did not bind any of the other 20S components (FIG. 6). Deletion mutant Syn 1A13, encompassing syntaxin residues 4 to 221, contained only the SNAP-25 binding site. When the four components VAMP, SNAP-25, α-SNAP and NSF were tested for their ability to bind, both VAMP and SNAP-25 associated with Syn 1A13, while no α-SNAP and very little NSF bound to the complex (the level of NSF binding was similar to that seen in with GST-only controls). This binding profile indicates that the complete region necessary for VAMP binding in the dimeric assay (Example 1; FIGS. 4A, 4B, 4C) is not necessary in the presence of SNAP-25. In contrast, no α-SNAP binding was observed, indicating that the presence of SNAP-25 does not enhance binding in the absence of the full α-SNAP binding domain on syntaxin.

Figure 6A:
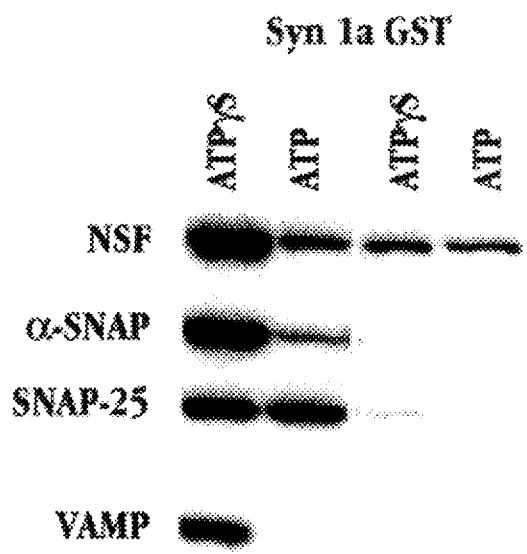
FIG. 6A is an image of a Western blot showing the assembly and dissociation of a complex between either GST-syntaxin 1A (left two lanes) or GST alone (right two lanes) and VAMP, SNAP-25, α-SNAP and NSF in the presence of either ATPTS or ATP.
Figures 7A, 7B:
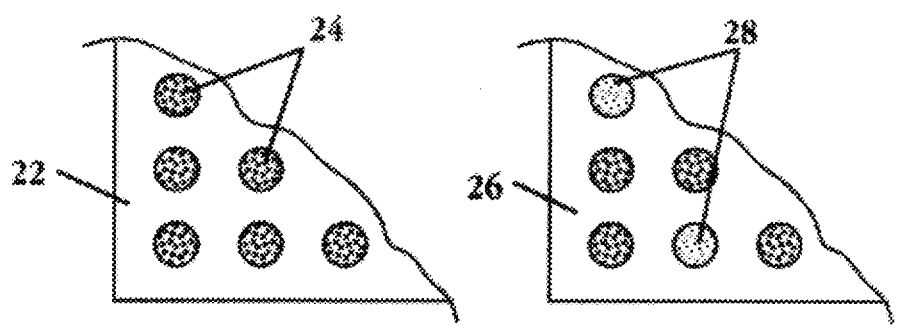
FIGS. 7A and 7B show fragmentary plan views of control (FIG. 7A) and experimental (FIG. 7B) multiwell plates used in a biochemical binding assay to identify compounds affecting binding of an SBP to a BPBS.
Figure 6B:
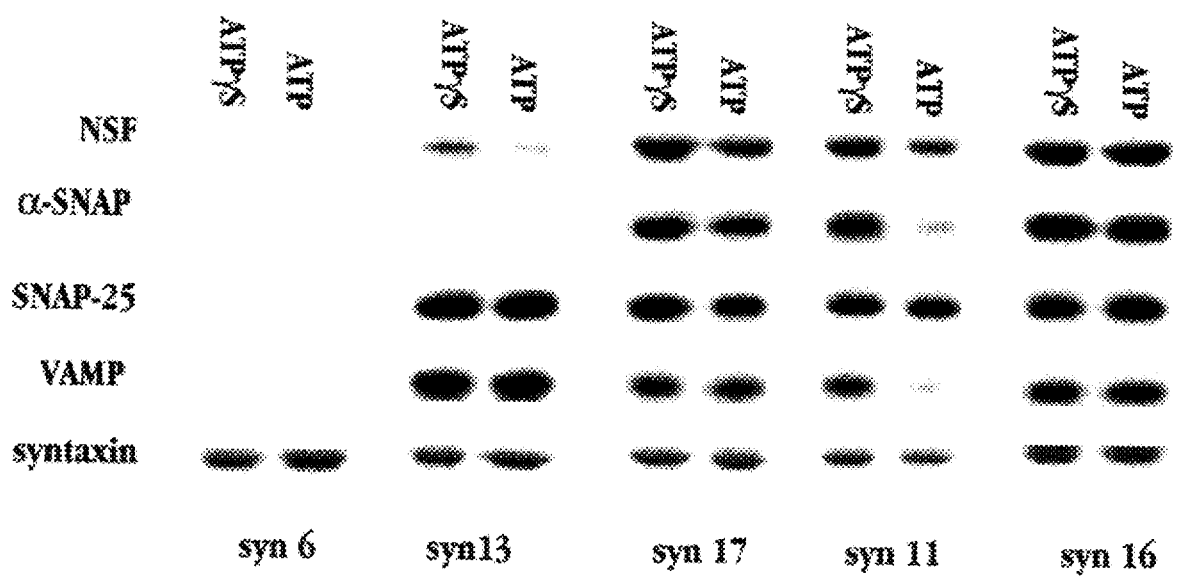
FIG. 6B is a computer-generated image of Western blots showing the assembly and dissociation of the 20S particle complex with five syntaxin deletion mutants.

The addition of the residues between 221 and 240 (deletion mutant Syn 1A17) allowed α-SNAP and NSF to add to the complex, but very little dissociation of the complex was observed in the presence of ATP and $Mg^{++}$. Approximately 30%, 25%, 0% and 0% of NSF, α-SNAP, SNAP-25 and VAMP, respectively, dissociated from syntaxin 1A17. In a similar fashion, the H3 domain construct (Syn 1A16), spanning residues 191–288, formed a complex that did not dissociate in the presence of ATP and $Mg^{++}$. Approximately 11%, 0%, 5% and 0% of NSF, α-SNAP, SNAP-25 and VAMP, respectively, dissociated from Syn 1A16 in the presence of ATP and $Mg^{++}$. Formation and hydrolysis of the 20S complex occurred only when it was formed on the syntaxin 1A11 construct (which contains residues 4–266; FIGS. 6A and 6B).

Analysis the above data suggests that the dissociation of the 20S complex requires the full cytoplasmic domain of the syntaxin protein. This dissociation may be the last energy-requiring step prior to the opening of the fusion pore. Further, these data are consistent with the binding site analysis and further indicate that amino terminal and carboxyl terminal domains, which are not needed to form the complex, are required for its dissociation. The lack of disassembly may be due to an inhibition of ATP hydrolysis by NSF, or to the lack of conformational changes necessary to dissociate VAMP, syntaxin and SNAP-25 following ATP hydrolysis.

The SBP n-sec1 had binding characteristics that differed somewhat from those of SNAP-25, VAMP and α-SNAP. In particular, n-sec1 was not observed as a component of the 7S or 20S complexes, but n-sec1 binding to syntaxin inhibited the binding of other proteins, including VAMP and SNAP-25, to syntaxin. While n-sec1 is not predicted to have coiled-coil domains, the H3 region of syntaxin was required for its binding. These data are consistent with n-sec1 stabilizing alternative conformations of syntaxin. For example, the n-sec1 protein may bind and stabilize a coiled-coil structure formed between the amino terminal (H1 and H2) and the carboxyl terminal (H3) domains of syntaxin. In this scenario, both amino and carboxyl terminal domains of syntaxin would be required for the binding n-sec1, and such binding would prevent the interaction of other proteins with the H3 helix.

III. Screens for Inhibitors of Synaptic Protein Interactions

The present invention includes methods of screening for compounds effective to modulate vesicular release involved in synaptic transmission and other secretory processes. The methods may be used to identify a compound capable of affecting binding of a syntaxin-binding protein (SBP), such as SNAP-25, α-SNAP, n-sec1 or VAMP, to its respective binding site on syntaxin. A selected SBP is contacted with a syntaxin polypeptide containing the binding site (binding protein binding site; BPBS) for the selected SBP, in the presence and absence of a test compound. The effect of the test compound on the extent of binding between the SBP and the BPBS is measured, and a compound is identified as effective if its effect on the extent of binding is above a threshold level (e.g., a several-fold difference in binding level between control and experimental samples).

It will be understood that the SBP may be only a fragment of a full length SNAP-25, α-SNAP, n-sec1 or VAMP, so long as that fragment retains the ability to bind to syntaxin at its normal binding site. Similarly, the polypeptide containing the BPBS may contain only portion of a full-length syntaxin sequence.

Compounds which affect the binding of a SNAP-25, α-SNAP, n-sec1 or VAMP syntaxin-binding protein (SBP) to syntaxin, when applied to target cells, typically modulate vesicular release by those cells. The modulation may be an inhibition of release or stimulation of release, either when the compound is applied alone, or when the compound is applied in conjunction with another compound having an effect on vesicular release.

Methods of the present invention may be applied to screen for compounds that selectively modulate release in a specific cell type or tissue. According to this aspect of the invention, the particular syntaxin and SBP used in the screening assay are selected such they correspond to the isoforms expressed together in the selected cell type or tissue. For example, Northern blot and immunofluorescence studies (Bennett, et al., 1992, 1993b) have shown that syntaxins 1A and 1B are expressed in the brain. Similar studies (in situ hybridization and Northern blot) have shown that VAMP 1 is expressed primarily in the spinal cord, while VAMP 2 is expressed primarily in the brain (Trimble, et al.). Western blot studies of n-sec1 expression (Pevsner, et al., 1994b), and in situ hybridization and immunofluorescence studies of SNAP-25 expression (Oyler, et al., 1989, 1992), have demonstrated that these molecules are also preferentially expressed in many regions of the brain.

Accordingly, modulators of vesicular release acting selectively in the brain, may be identified by employing a screen such as described herein using fusion proteins of syntaxin 1A and any of SNAP-25, nsec-1 or VAMP 2. Compounds identified as effective at altering or affecting the binding of these molecules with each other, but having a reduced effect on the binding of SBPs to syntaxin isoforms not preferentially expressed in the brain, such as syntaxins 2,3,4 or 5, (sequences of which are presented herein as SEQ ID NOs:5–12, respectively) are useful as selective modulators of vesicular release in the brain.

It will be understood that one of skill in the art having the benefit of the present disclosure may readily design experiments, such as in situ hybridization experiments, to assess the expression pattern of specific syntaxin and SBP isoforms in a selected tissue, and then construct fusion proteins of those isoforms for screening of compounds effective in that tissue. Techniques for analyzing expression patterns in various tissues, such as Northern and Western blot analysis and immunohistochemistry, are well known (e.g., Ausubel, et al.), as are methods of selectively assaying expression of closely-related isoforms (e.g., by using 5' and/or 3' untranslated sequences as probes). Expression patterns of such related isoforms may also be assayed immunohistochemically using isoform-specific antibodies and standard techniques. Such antibodies may be generated using standard methods (Harlow, et al.), for example, by immunizing rabbits with peptides corresponding to unique epitopes on related isoforms.

Methods for the production of recombinant proteins useful in the assays described below are detailed in the Materials and Methods section, below. Specifically, polynucleotide sequences encoding SBPs or BPBSs of the present invention may be cloned into an expression plasmid, such as p-GEX-KG (described below), to produce corresponding polypeptides. Recombinant pGEX-KG plasmids can be transformed into appropriate strains of *E. coli* and fusion protein production can be induced by the addition of IPTG (isopropyl-thio galactopyranoside). Solubilized recombinant fusion protein can then be purified from cell lysates of the induced cultures using glutathione agarose affinity chromatography according to standard methods (described below; Ausubel, et al.).

Affinity chromatography may also be employed for isolating β-galactosidase fusion proteins (such as those produced by lambda gt11 clones). The fused protein is isolated by passing cell lysis material over a solid support having surface-bound anti-β-galactosidase antibody.

Isolated recombinant polypeptides produced as described above may be purified by standard protein purification procedures. These procedures may include differential precipitation, molecular sieve chromatography, ion-exchange chromatography, isoelectric focusing, gel electrophoresis and affinity chromatography.

In addition to recombinant methods, SBP and/or BPBS proteins or polypeptides can be isolated from selected cells by affinity-based methods, such as by using appropriate antibodies (described below). Further, SBP and/or BPBS peptides may be chemically synthesized using methods known to those skilled in the art.

It will be understood that polypeptides or protein used as the "free" protein in a partner capture assay are synthesized so that they remain soluble during the binding assay. Proteins normally associated with lipid membranes, such as syntaxin, VAMP, and SNAP-25, may be modified for increased solubility by, for example, expressing truncated versions ("cytoplasmic domains") of the proteins minus their membrane anchors.

A. Protein-Interaction Binding Assays

A variety of approaches may be employed to assay the binding of an SBP, such as SNAP-25, VAMP, etc., with a corresponding binding site (BPBS) from a region of syntaxin. They include biochemical approaches (such as immobilized GST fusion protein constructs), bioassays (such as the yeast two-hybrid system), and physical biosensor assays (such as surface plasmon resonance). These assays are described in more detail below.

1. Biochemical Assays. Biochemical assays useful in the practice of the present invention include partner assays similar to those described above (FIGS. 2A–2D) for the localization of syntaxin-binding protein binding sites on syntaxin.

To identify a compound capable of affecting binding of an SBP to syntaxin, a test compound is included in the solution (containing the "free" soluble protein; e.g., the SBP) that is contacted with the immobilized protein (e.g., the BPBS). The amount of bound SBP is detected and compared to the amount bound under similar conditions in the absence of the test compound (control). If the compound has a significant effect on the binding of the SBP to the BPBS (i.e., if the compound significantly increases or significantly decreases the binding), and the effect exceeds a threshold value (which is set to a desired level by the practitioner of the invention; e.g., several-fold increase or several-fold decrease in binding), the compound is identified as effective to affect or alter the binding of the SBP to the BPBS.

Illustrations of results that may be obtained with such an assay in a multiwell plate are shown in FIGS. 7A and 7B. Both figures show fragmentary plan views of a multiwell plates. The plate 22 in FIG. 7A is the control plate (without test compounds). Detection of binding of the free protein to the immobilized protein is indicated by the stippled pattern in the wells 24. The wells of the plate 26 in FIG. 7B each contain different test compounds, two of which inhibit the binding of the free protein to the immobilized protein. This inhibition is evidenced by a lighter stippled pattern in the wells 28 containing the effective compounds.

It will be understood that various modification of the above-described assay are included within the scope of the present invention. For example, the roles of the proteins can be switched—that is, the SBP may be immobilized to the solid support and a solution containing the BPBS may be contacted with the SBP. Additionally, the immobilized protein or the free protein may be exposed to a test compound prior to the binding assay, and the effects of this pre-exposure may be assessed relative to controls. Compounds identified in this manner also inhibit the binding of the SBP to the BPBS or vice versa. Alternatively, the test compound may be added subsequent to the mixing of the SBP with the BPBS. A compound effective to reduce the level of binding in such an assay displaces the SBP from the BPBS, or vice versa. Further, it will be understood that the GST-based methods described above may be employed with other types of recombinant proteins thought to interact with syntaxin (SBPs), including β-SNAP, γ-SNAP, synaptotagmin and N-type calcium channels.

In addition to Western blots, other, more rapid, detection schemes, such as multiwell ELISA-type approaches, may be employed. For example, a partially-purified (e.g., by the GST methods above) syntaxin polypeptide may be attached to the bottoms of wells in a multiwell plate (e.g., 96-well plate) by introducing a solution containing the polypeptide into the plate and allowing the polypeptide to bind to the plastic. The excess peptide-containing solution is then washed out, and a blocking solution (containing, for example, bovine serum albumin (BSA)) is introduced to block non-specific binding sites. The plate is then washed several more times and a solution containing an SBP and, in the case of experimental (vs. control) wells, a test compound added. Different wells may contain different test compounds, different concentrations of the same test compound, different SBPs or BPBSs, or different concentrations of SBPs or BPBSs. Further, it will be understood that various modifications to this detection scheme may be made. For example, the wells of a multiwell plate may be coated with a polypeptide containing the SBP, rather than the BPBS, and binding interactions assayed upon addition of a free BPBS. The wells may also be precoated with substance (s) that enhance attachment of the protein to be immobilized and/or decrease the level of non-specific binding. For example, the wells may be derivatized to contain glutathione and may be pre-coated with BSA, to promote attachment of the immobilized protein in a known orientation with the binding site(s) exposed.

Detection methods useful in such assays include antibody-based methods (i.e., an antibody directed against the "free" protein), direct detection of a reporter moiety incorporated into the "free" protein (such as a fluorescent label), and proximity energy transfer methods (such as a radioactive "free" protein resulting in fluorescence or scintillation of molecules incorporated into the immobilized protein or the solid support).

In particular, multiwell plates (e.g., 96-well plates) that contain a scintillating material in the wells (available from, e.g., Wallac, Gaithersburg, Md.) may coated with the immobilized protein and used in conjunction with radioactively-labeled free protein. Free protein that binds the immobilized protein is constrained within a few nanometers of the well surface, resulting in light emission from the scintillation material in the wells. The signal can be quantitated using a plate reader or counter, such as the "MICROBETA PLUS" plate counter (Wallac), to generate standard binding plots. Such plots may be used to determine the optimal concentrations of proteins used in the assay, and may be useful in identifying compounds with more subtle effects on SBP/BPBS binding that can be detected using some other methods.

2. Yeast Two-Hybrid Assays. The yeast two-hybrid protein interactionassay may also be employed to identify compounds that affect the binding of an SBP to a BPBS. The assay is based on the finding that most eukaryotic transcription activators are modular (e.g, Brent, et al.), i.e., that the activators typically contain activation domains that activate transcription, and DNA binding domains that localize the activator to the appropriate region of a DNA molecule.

In a two hybrid system, a first fusion protein contains one of a pair of interacting proteins fused to a DNA binding domain, and a second fusion protein contains the other of a pair of interacting proteins fused to a transcription activation domain. The two fusion proteins are independently expressed in the same cell, and interaction between the "interacting protein" portions of the fusions reconstitute the function of the transcription activation factor, which is detected by activation of transcription of a reporter gene.

At least two different cell-based two hybrid protein-protein interaction assay systems have been used to assess binding interactions and/or to identify interacting proteins. Both employ a pair of fusion hybrid proteins, where one of the pair contains a first of two "interacting" proteins fused to a transcription activation domain of a transcription activating factor, and the other of the pair contains a second of two "interacting" proteins fused to a DNA binding domain of a transcription activating factor.

The yeast GAL4 two hybrid system (Fields, et al.; Chien, et al.; Durfee, et al.; Bartel, et al.) was developed to detect protein-protein interaction based on the reconstitution of function of GAL4, a transcriptional activator from yeast, by activation of a GAL1-lacZ reporter gene. Like several other transcription activating factors, the GAL4 protein contains two distinct domains, a DNA binding domain and a transcription activation domain. Each domain can be independently expressed as a portion of a fusion protein composed of the domain, and a second, "bait" interacting protein. The two fusion proteins are then independently expressed together in a cell. When the two GAL4 domains are brought together by a binding interaction between the two "interacting" proteins, transcription of a reporter gene under the transcriptional control of GAL4 is initiated. The reporter gene typically has a promoter containing GAL4 protein binding sites (GAL upstream activating sequences, $UAS_G$).

A two hybrid system such as is described above may be used to identify compounds effective to disrupt the binding of an SBP to a BPBS as follows. A polynucleotide encoding a BPBS is fused to the GAL4 DNA binding domain (G4BD) in a yeast expression vector (e.g., pG4BD-Syn1A11). The vector is used to generate yeast cells harboring pG4BD-Syn1A11 and a GAL4-activated reporter gene (e.g., LacZ). These cells are then transformed with a vector carrying a fusion between the transcription activating domain of yeast GAL4 (G4AD) and an SBP (e.g., pG4AD-VAMP). Transformants are screened (e.g., using a β-galactosidase (β-gal) assay on plates containing the chromogenic substrate X-gal) for expression of the reporter. Reporter-expressing cells are selected, cloned, and used to screen test compounds. Compounds which increase or decrease reporter expression relative to a user-defined threshold (e.g., five-fold increase or five-fold decrease) are identified as affecting binding of the SBP to syntaxin, and may be further evaluated, e.g., as described below, for effects on vesicular release.

A second two hybrid system, described in detail in Ausubel, et al., utilizes a native E. coli LexA repressor protein which binds tightly to appropriate operators. A plasmid is used to express one of a pair of interacting proteins (the "bait" protein) as a fusion to LexA.

The plasmid expressing the LexA-fused bait protein is used to transform a reporter strain of yeast, such as EGY48. In this strain, binding sites for LexA are located upstream of two reporter genes. In the first reporter system, the upstream activation sequences of the chromosomal LEU2 gene—required in the biosynthetic pathway for leucine (Leu)—are replaced in EGY48 with lexA operators, permitting selection for viability when cells are plated on medium lacking Leu.

In the second reporter system, EGY48 harbors a plasmid, pSH18-34, that contains a lexA operator-lacZ fusion gene, permitting discrimination based on color when the yeast is grown on medium containing Xgal (Ausubel, et al.).

LexA and GAL4 each have different properties that should be considered when selecting a system. LexA is derived from a heterologous organism, has no known effect on the growth of yeast, possesses no residual transcriptional activity, can be used in GAL4⁺ yeast, and can be used with a Gal-inducible promoter. Because GAL4 is an important yeast transcriptional activator, experiments must be performed in gal4 yeast strains to avoid background from endogenous GAL4 activating the reporter system. Both two hybrid systems have been successfully used for isolating genes encoding proteins that bind a target protein and as simple protein binding assays (e.g., Yang, et al., Gyuris, et al.), and both can be applied to the identification of compounds capable of affecting binding of a syntaxin-binding protein to syntaxin.

3. Biosensor-Based Assays. Yet another method of identifying a compound capable of affecting binding of a syntaxin-binding protein to syntaxin is through the use of affinity biosensor methods. Such methods may be based on the piezoelectric effect (Calabrese, et al.; Ngeh-Ngwainbi, et al.; Rajakovic, et al.; Roederer and Bastiaans; Ward and Buttry), electrochemistry (Ngo), or optical methods, such as ellipsometry (Corsel; Jönsson, et al.; Vroman and Adams), optical wave guidance (Nellen and Lukosz) and surface plasmon resonance (SPR, Cullen, et al.; Liedberg, et al.). SPR is particular advantageous for monitoring molecular interactions in real-time, enabling a sensitive and comprehensive analysis of the effects of test compounds on the binding interactions between two proteins than the methods discussed above. This advantage is somewhat offset, however, by the lower throughput of the technique (as compared with multiwell plate -based methods).

Figure 8A:
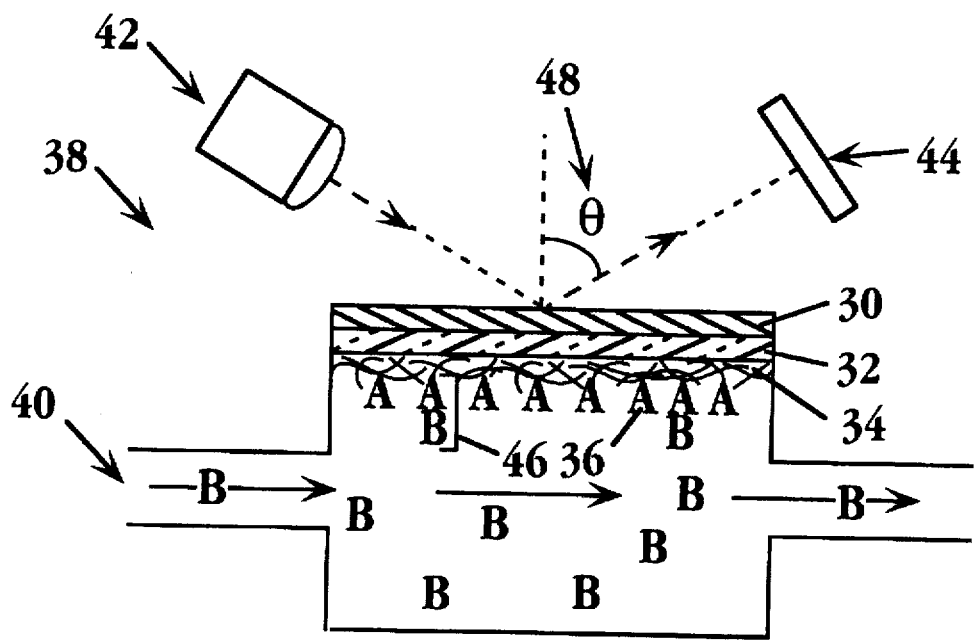
FIG. 8A is a schematic of a surface plasmon resonance (SPR) detection apparatus used to evaluate the rates of protein-protein binding.

In this approach, schematized in FIG. 8A, a thin layer of gold 32 deposited on a glass support 30 is derivatized with a flexible hydrophilic polymer 34 to facilitate attachment of a selected receptor "A" 36, such as a polypeptide containing BPBS. The support containing the gold film and ligand is placed into a cell 38 which allows a solution 40 to be passed over the surface containing the receptor. The gold film is illuminated at an angle with a light-emitting diode (42; LED), and reflected light is analyzed with a photodetector 44. Through an evanescent electric field generated by the interaction of incident light with the gold film, the reflected light is sensitive to the environment of a layer extending about 1 μm ($\lambda$=760 nm) from the attached polypeptide (receptor; "A") into the medium. Changes in the environment of the polypeptide, such as are caused by the binding of a ligand "B" (e.g., an SBP) to the polypeptide receptor 46, are detected as changes in the reflectance intensity at a specific angle 48 of reflection (the resonance angle).

Figure 8B:
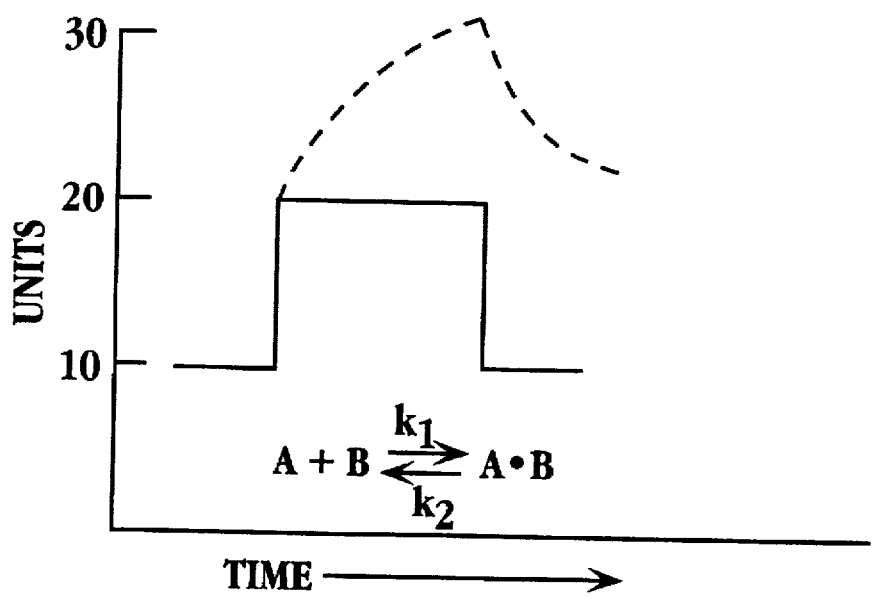
FIG. 8B is a representation of data which may be obtained from an apparatus such as shown in FIG. 8A.

FIG. 8B illustrates the type of data which may be obtained using an apparatus such as shown in FIG. 8A. In response to a step increase in the concentration of ligand protein "B", the resonance units (RU) increase with an exponential time-course reflecting the rate constants $k_1$ and $k_2$ of "B" binding to immobilized "A" to form the complex "AB". When "B" is eliminated from the flow-through solution, the RU units decay back to the starting value.

Figure 9A:
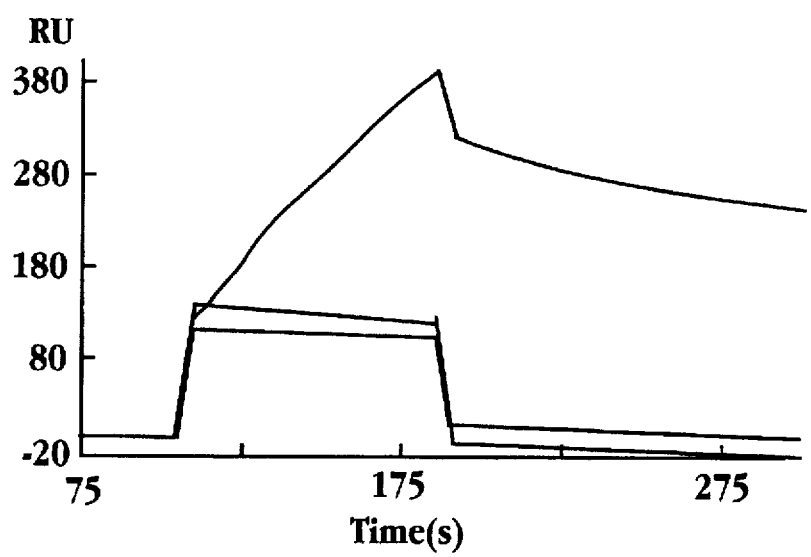
FIGS. 9A, 9B and 9C show exemplary data, obtained using an SPR detection apparatus, relating to syntaxin 1A binding to VAMP 2.
Figure 9B:
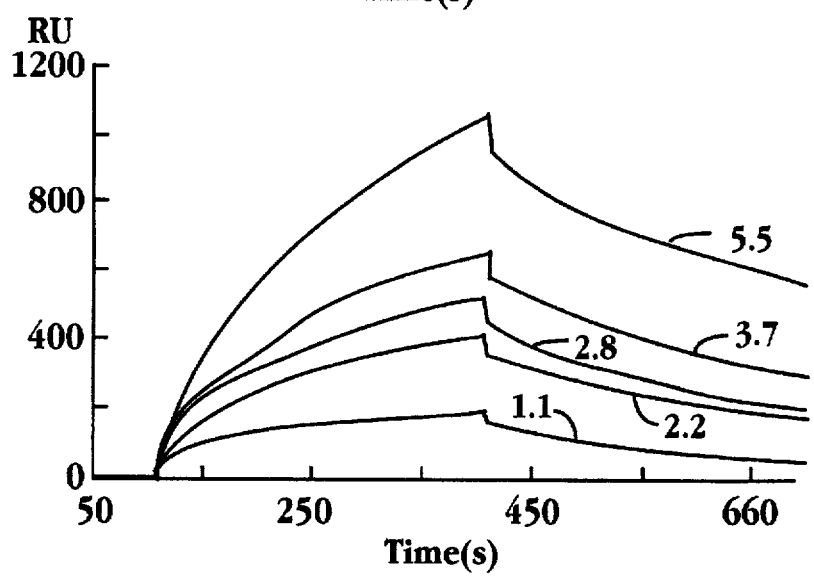
Figure 9C:
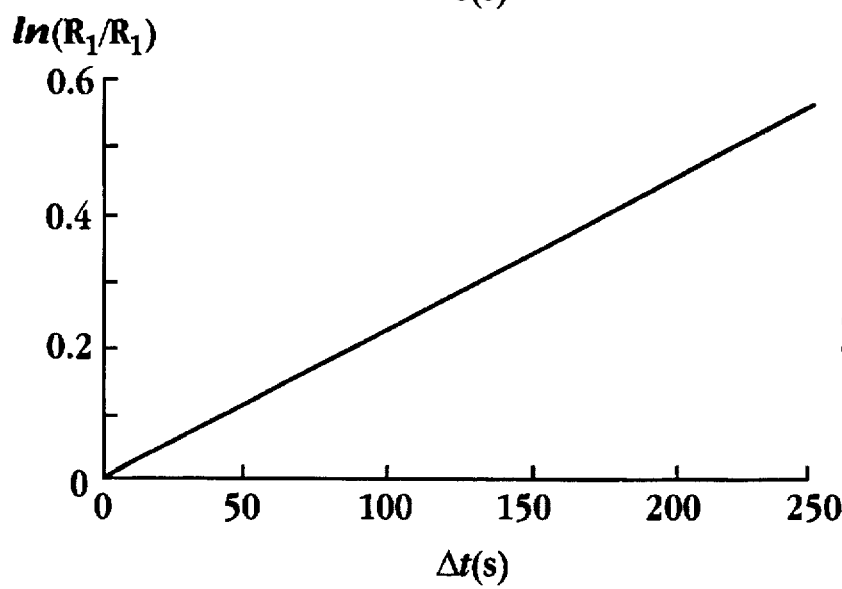

The SPR approach was used to detect the binding of immobilized VAMP 2 to different regions of "free", soluble syntaxin 1A, as detailed in Example 3. Exemplary results from these experiments are illustrated in FIGS. 9A, 9B and 9C. The data in FIG. 9A illustrate that the carboxyl domain of syntaxin 1A (amino acids 194–267; top trace), but not the amino (amino acids 4–193) or the complete cytoplasmic (amino acids 4–267) domains, bound to the immobilized cytoplasmic domain of VAMP 2 (amino acids 1–94). These results confirm the above-described localization of the VAMP-binding domain on syntaxin, and suggest that the N-terminal domain of "free", soluble syntaxin may interact with the carboxyl domain to inhibit binding of syntaxin to VAMP.

FIG. 9B shows that increasing concentrations (indicated at the right of the traces) of syntaxin 1A carboxyl-terminal domain result in increased total binding to VAMP 2. These data may be utilized to generate a plot of $\ln(R^i/R_s)$ as a function of $\Delta t$, shown in FIG. 9C. This plot is a linearizing transformation of the dissociation phase of the carboxyl-terminal domain of syntaxin 1A (5.5 μM) from VAMP 2, and can be used to calculate the dissociation rate. The concentration-dependent binding of the carboxyl-terminal syntaxin 1A fragment was used to calculate kinetic rate constants. The association rate constant, $k_a$, was 470±50 M⁻¹s⁻¹ (SEM) (n=13). The dissociation rate constant, $k_d$, was $2.2 \times 10^{-3} \pm 0.3 \times 10^{-3}$ s⁻¹ (SEM) (n=6). From these data, the calculated dissociation equilibrium constant ($K_D = k_d/k_a$) is 4.7 μM.

Figure 10A:
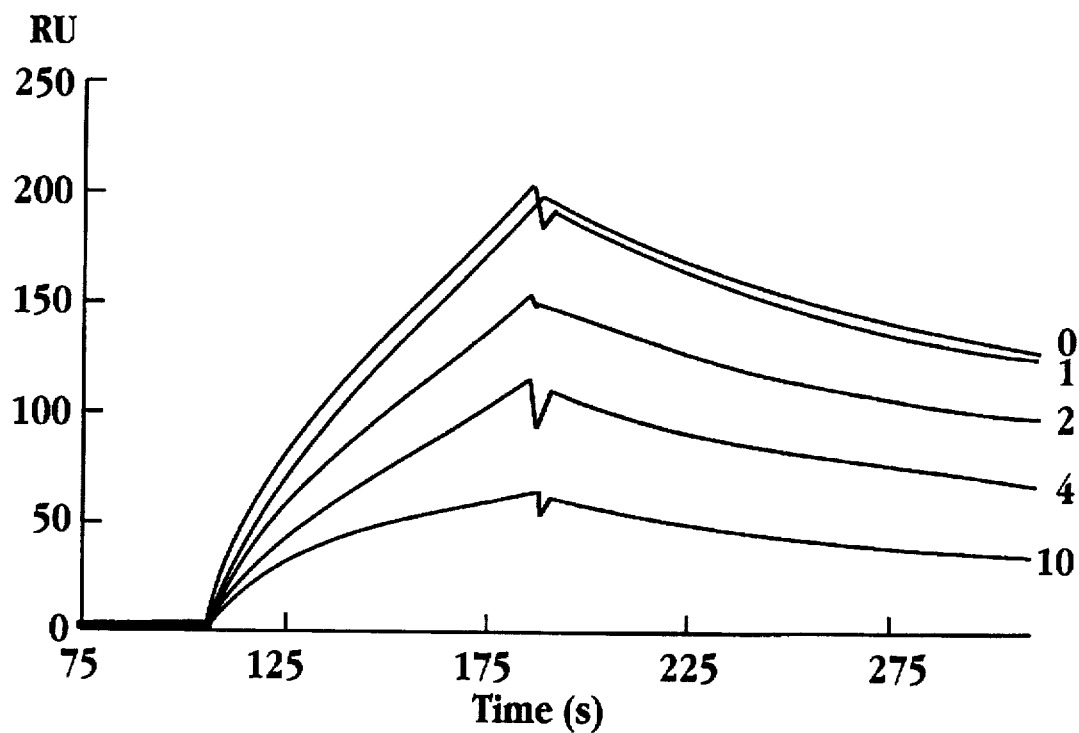
FIG. 10A illustrates SPR data showing the inhibition of syntaxin-VAMP binding by a polypeptide corresponding to the amino terminus of syntaxin 1A.
Figure 10B:
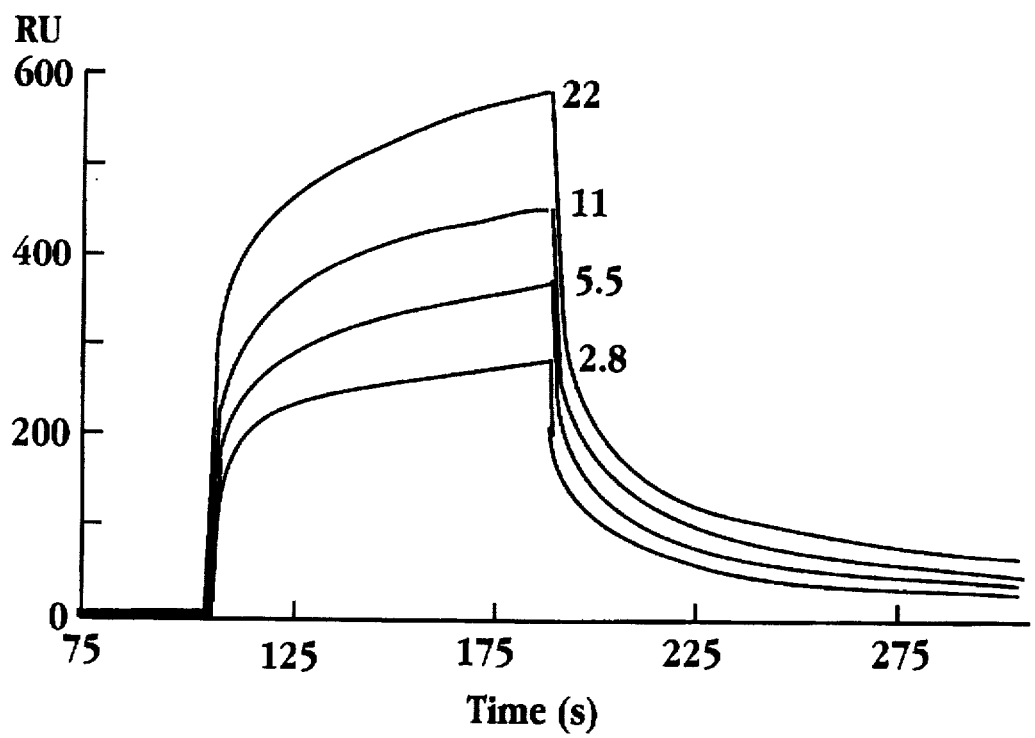
FIG. 10B illustrates SPR data showing syntaxin 1A carboxyl-terminal domain binding to immobilized syntaxin 1A amino-terminal domain.

SPR was also used to assess whether amino- and carboxyl-terminal domains of syntaxin 1A interact to effect VAMP 2 binding, as suggested by the data in FIG. 9A. Exemplary results are shown in FIGS. 10A and 10B. Data shown in FIG. 10A indicate that increasing concentrations (indicated at the right of the traces) of the amino terminal domain syntaxin 1A polypeptide (amino acids 4–193) inhibit the binding of the carboxyl-terminal domain (5.5 μM) to immobilized VAMP 2 cytoplasmic domain. Accordingly, the inhibitory peptide may be viewed as a compound identified as effective to alter the binding of an SBP (VAMP 2) to a BPBS (the carboxyl terminal domain of syntaxin).

The data presented in FIG. 10B demonstrate that syntaxin 1A carboxyl-terminal domain binds to immobilized syntaxin 1A amino-terminal domain, providing an interpretation of the results observed in FIGS. 9A and 10A (i.e., that inhibition of VAMP 2 binding to the carboxyl terminal domain of syntaxin may be due to the binding of the amino terminal domain of syntaxin to its carboxyl terminal domain).

B. Measuring the Effect of a Test Compound on the Extent of Binding

The type of measurement used to quantify the effect of a test compound on the extent of binding between the SBP and the BPBS depends on the type of screening assay and detection system used, and can be readily determined by one of skill in the art.

For example, in a biochemical screen employing a Western blot detection, such as illustrated in Examples 1 and 2, the extent of binding may be measured using densitometry, as described herein. The densitometry values may be normalized, and a threshold level may be set based on the amount of variation in the signal between a series of "control" samples (samples not containing test compounds). The smaller the variation, the smaller the effect of a test compound that can be reliably detected.

If a multiwell plate screen is used, the output of a plate reader used to score the results of the experiment may be used as a measure of the effect on the extent of binding, and a threshold set as described above. For binding studies using surface plasmon resonance, the actual equilibrium dissociation constants ($K_D$s) may be calculated from the data (e.g., as described in Example 3), and $K_D$s obtained in the presence and absence of a test compound can be directly compared.

C. Effects of Identified Compounds on Vesicular Release

Compounds identified by a screen such as one described above as affecting the binding of an SBP to an BPBS may be further evaluated for their effects on multimer formation (e.g., by using the 20s particle association/dissociation assays detailed in Example 2), as well as for their ability to modulate vesicular release in vitro and in vivo.

For example, the compounds may be tested using the PC12 cell DβH vesicular release assay (Bennett, et al., 1993b), which detects a membrane-associated form of the enzyme dopamine β-hydroxylase (DβH) on the luminal side of catecholamine-containing granules. When the cells are depolarized in the presence of calcium, granule fusion with the plasma membrane results in the exposure of DβH on the cell surface, where it can be quantitatively detected by innnunofluorescence microscopy (Elferink, et al.). By treating a sample of cells with a compound identified as affecting the binding of an SBP to a BPBS, depolarizing the cells (e.g., with a pulse of KCl) in the presence of calcium, and comparing the response to that obtained with an untreated sample of cells, the effects of the compound on vesicle release in PC12 cells may be assessed. Similar assays may be employed using freshly-isolated cells (e.g., in brain slices), or suitable animal models.

IV. Compounds Suitable for Screening

A variety of different compounds may be screened using methods of the present invention. They include peptides, macromolecules, small molecules, chemical and/or biological mixtures, and fungal, bacterial, or algal extracts. Such compounds, or molecules, may be either biological, synthetic organic, or even inorganic compounds, and may be obtained from a number of sources, including pharmaceutical companies and specialty suppliers of libraries (e.g., combinatorial libraries) of compounds.

In cases where an identified active compound is a peptide, the peptide may be utilized to aid in the discovery of orally-active small molecule mimetics. For example, according to the teachings of the present invention, a peptide having the sequence (SEQ ID NO:25) of the N-terminal portion of syntaxin 1A (amino acids 4–193) is effective at inhibiting the binding of VAMP 2 to its binding site (BPBS) at the C-terminal of the syntaxin polypeptide (Example 3, FIG. 10A). Further, as described herein, the effectiveness of this inhibitory peptide may be due to the H1 and H2 regions schematized in FIG. 4A. Accordingly, the structure of the polypeptide, or of a fragment containing the H1 and H2 domains, may be determined using, for example, NMR, and may be used to select the types of small molecules screened. Similar analyses may be applied to the binding sites on the SBPs that bind to the BPBSs.

Methods of the present invention are well suited for screening libraries of compounds in multi-well plates (e.g., 96-well plates), with a different test compound in each well. In particular, the methods may be employed with combinatorial libraries. A variety of combinatorial libraries of random-sequence oligonucleotides, polypeptides, or synthetic oligomers have been proposed (Kramer, et al.; Houghten, 1985, 1994; Houghten, et al., 1986, 1991, 1992; Ohlmayer, et al.; Dooley, et al., 1993a–1993b; Eichler, et al.; Pinilla, et al., 1992, 1993; Ecker, et al.; and Barbas, et al.). A number of small-molecule libraries have also been developed (e.g., Bunin, et al.; Bunin and Ellman; Virgilio and Ellman).

Combinatorial libraries of oligomers may be formed by a variety of solution-phase or solid-phase methods in which mixtures of different subunits are added stepwise to growing oligomers or parent compound, until a desired oligomer size is reached (typically hexapeptide or heptapeptide). A library of increasing complexity can be formed in this manner, for example, by pooling multiple choices of reagents with each additional subunit step (Houghten, et al., 1991).

Alternatively, the library may be formed by solid-phase synthetic methods in which beads containing different-sequence oligomers that form the library are alternately mixed and separated, with one of a selected number of subunits being added to each group of separated beads at each step (Furka, et al., 1991; Lam, et al., 1991, 1993; Zuckermann, et al.; Sebestyen, et al.).

The identity of library compounds with desired effects on the binding of an SBP to a BPBS can be determined by conventional means, such as iterative synthesis methods in which sublibraries containing known residues in one subunit position only are identified as containing active compounds.

V. Applications

Inhibitory compounds isolated using methods of the present invention may be employed to inhibit vesicle-mediated secretion of molecules from cells. Similarly, compounds which enhance or potentiate the binding of an SBP to a BPBS may be used to upregulate vesicle-mediated secretion. The ability to modulate secretion processes has utility in a variety of areas, some of which are identified below.

A. CNS Disease Applications

A number of disorders and/or conditions of the central nervous system (CNS) may be alleviated by selectively enhancing or inhibiting vesicular release in specific areas of the brain. They include affective disorders (e.g., depression), disorders of thought (e.g., schizophrenia) and degenerative disorders (e.g., Parkinson's disease), as well as applications such as anesthesia. A variety of drugs are currently used to treat such disorders and/or conditions. Compounds identified by methods of the present invention may be used either alone, or in combination with currently used therapies to alleviate symptoms associated with the disorders.

Drugs used to treat affective disorders, which include depression, manic-depressive disorders and anxiety disorders, typically fall into three classes: (i) monoamine oxidase (MAO) inhibitors, such as phenelzine, (ii) tricyclic compounds, such as imipramine, and (iii) serotonin uptake blockers, such as fluoxetine and trazodone. All of these drugs work, at least in part, by increasing the concentration of either serotonin or biogenic amine neurotransmitters in CNS synapses of treated individuals. According to methods of the present invention, compounds which enhance the release of serotonin or biogenic amines at selected brain synapses may be similarly effective at treating depressive disorders. Such compounds may be identified by screening for compounds effective to enhance the binding of selected SBPs for a BPBS.

Disorders of thought, such as schizophrenia, have been treated with a variety of antipsychotic drugs (including phenothiazines, such as chlorpromazine, butyrphenones, such as haloperidol, xithioxanthenes, and newer drugs, such as clozapine) now known to act as blockers of dopamine receptors. According to the teachings presented herein, compounds identified as inhibitors of release of dopamine-containing vesicles, particularly vesicles released from cells having their cell bodies in the arcuate nucleus of the hypothalamus, the substantia nigra, or the ventral tegmental area, may be employed to relieve symptoms of schizophrenia. Such compounds may be identified using a screening assay such as described above, with syntaxin 1A or 1B and VAMP 2, SNAP-25, and/or n-sec1.

Neurodegenerative diseases, such as Parkinson's disease and Huntington's disease, may also benefit from compounds identified according to the methods of the present invention. Parkinson's disease is due to degeneration of the nigrostriatal pathway, raphaei nuclei, locus ceruleus, and motor nucleus of vagus, which result in a reduction of dopamine, serotonin and norepinephrine levels. The symptoms of Parkinson's may be alleviated by administering compounds identified according to the teachings presented herein as stimulating release of vesicles containing the above neurotransmitters.

B. Other Applications

In addition to applications in the CNS, compounds identified employing methods of the present invention may be used to therapeutically intervene in a variety of other systems. They include the endocrine system for treatment of hormonal imbalances, the immune system for intervention in antigen processing, secreted immunomodulators, and viral processing, as well as anti-tumor applications, such as regulation of membrane trafficking during rapid cell division. Syntaxin constructs based on syntaxin 2, 3, 4 or 5 may be used in screens for compounds effective in the above systems, since these constructs are not preferentially expressed in the brain. To avoid CNS-related side-effects, compounds identified in such screens may also be tested with syntaxin 1 constructs to identify those that act selectively on the binding to syntaxins 2, 3, 4 or 5.

The following examples illustrate but in no way are intended to limit the present invention.

MATERIALS AND METHODS

Unless otherwise indicated, restriction enzymes and DNA modifying enzymes were obtained from New England Biolabs (Beverly, Mass.) or Boehringer Mannheim (Indianapolis, Ind.). [$^{125}$I]goat anti-rabbit secondary antisera and the Enhanced Chemo-Luminescence (ECL) system were obtained from Amersham Corp. (Arlington, Heights, Ill.). Nitrocellulose paper was obtained from Schleicher and Schuell (Keene, N.H.). "pBLUESCRIPT II SK$^{-}$" and R408 helper phage were obtained from Stratagene (La Jolla, Calif.). Materials for SDS-polyacrylamide gel electrophoresis (SDS-PAGE) were obtained from Bio-Rad Laboratories (Hercules, Calif.). Glutathione-agarose, thrombin, and other chemicals were purchased from Sigma (St. Louis, Mo.) or United States Biochemical (Cleveland, Ohio).

A. Buffers

Phosphate-buffered saline (PBS)
10x stock solution, 1 liter:
80 g NaCl
2 g KCl
11.5 g Na$_2$HPO4-7 H$_2$O
2 g KH$_2$PO$_4$
Working solution, pH 7.3:
137 mM NaCl
2.7 mM KCl
4.3 mM Na$_2$HPO$_4$-7 H$_2$O
1.4 mM KH$_2$PO$_4$
Suspension Buffer
0.05% Tween-20 in PBS
Cleavage Buffer
50 mM Tris-HCl (pH 8.0)
50 mM NaCl 2.5 mM CaCl$_2$
0.1% β-mercaptoethanol
10 µg/ml thrombin (~3000 U/mg)
HBS-T20 Buffer
20 mM HEPES, pH 7.4
150 mM KCl
0.05% Tween-20
Buffer A
25 mM Tris-HCl, pH 7.8
75 mM KCl
2 mM β-mercaptoethanol
1 mM phenylmethylsulfonyl fluoride (PMSF)
Buffer B
100 mM HEPES/KOH, pH 7
500 mM KCl
5 mM MgCl$_2$
2 mM β-mercaptoethanol
1 mM PMSF
0.5 mM ATP
Buffer C
20 mM HEPES/KOH, pH 7
200 mM KCl
2 mM β-mercaptoethanol
0.5 mM ATP
10% glycerol
Buffer D
20 mM HEPES, pH 7.4
150 mM potassium acetate
0.05% "TWEEN 20"
Buffer E
20 mM HEPES, pH 7.4
150 mM KCl
1 mM dithiothreitol
1% polyethylene glycol 3350
5% glycerol
0.05% "TWEEN 20"
Buffer F
20 mM HEPES, pH 7.4
150 mM KCl
2 mM CaCl$_2$

B. Cloning of Constructs

Plasmid vectors described herein were constructed by cloning selected cDNAs into either pGEX-KG (Guan and Dixon) or pQE-9 (Qiagen, Chatsworth, Calif). The plasmid pGEX-KG was derived from the pGEX-2T plasmid (Pharmacia Biotech, Piscataway, N.J.) by incorporation of an EcoRI fragment encoding a nine amino-acid glycine-rich linker (Guan and Dixon). The pGEX-2T plasmid was designed for inducible, high level intracellular expression of genes or gene fragments as fusions with *Schistosoma japonicum* glutathione S-transferase (GST; Smith and Johnson). It contains a tac promoter for chemically-inducible expression, the GST gene, a thrombin protease recognition site, a multiple cloning site, an ampicillin resistance gene, a pBR322 ori, and an internal lac Iq gene.

Figures 11A, 11B:
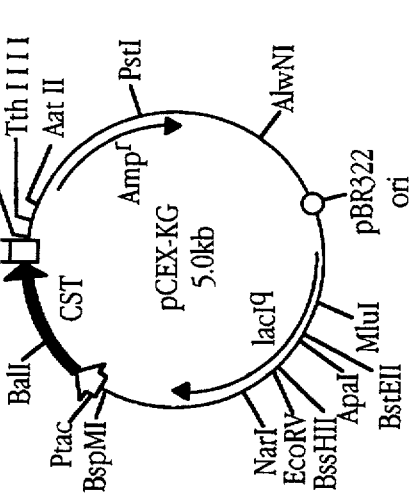
FIG. 11A shows the polylinker region of the pGEX-KG vector (Guan and Dixon).
FIG. 11B shows a map of the pGEX-KG vector.

The thrombin recognition sequence, glycine-rich linker and multiple cloning site of pGEX-KG are illustrated in FIG. 11A. A schematic of the entire plasmid is shown in FIG. 11B.

Figure 12A:
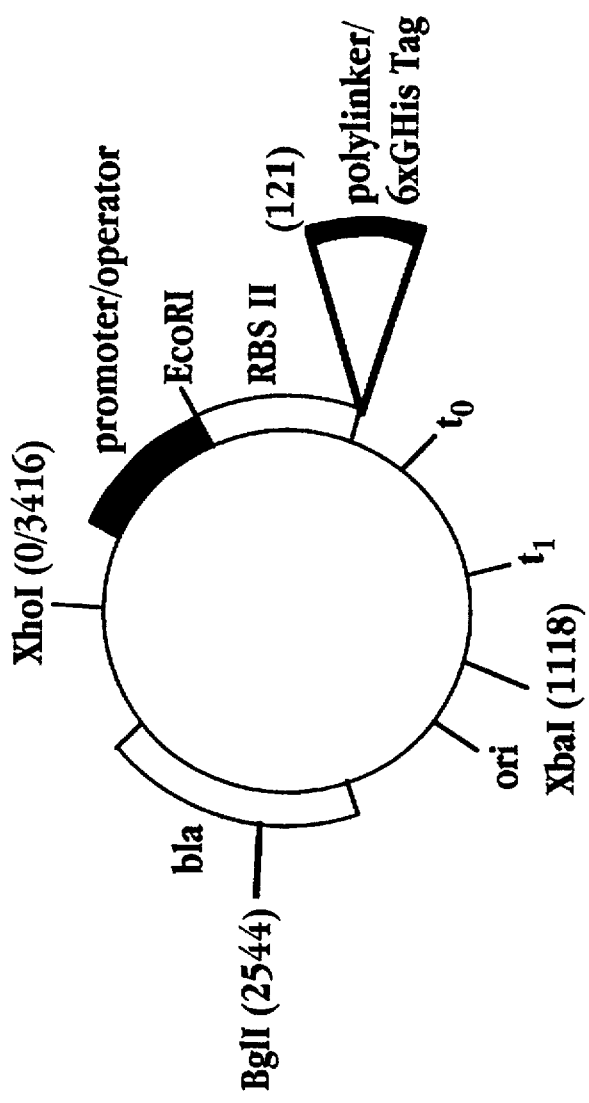
FIGS. 12A and 12B show schematic diagrams of the pQE-9 vector (FIG. 12A; Qiagen, Chatsworth, Calif.) and its polylinker region (FIG. 12B).
Figure 12B:
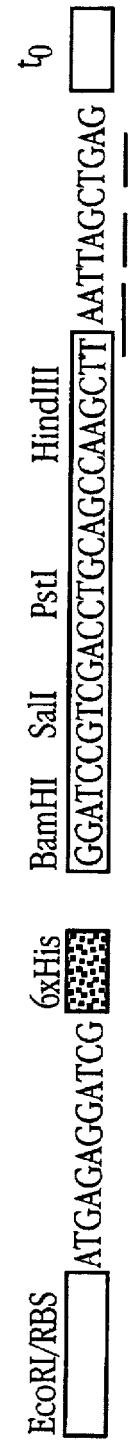

The plasmid pQE-9 (FIG. 12A) contains the phage T5 promoter and two lac operator sequences, a synthetic ribosome binding site (RBSII), a 6xHis tag coding sequence effective to express six histidines at the N-termini of the fusion proteins, a multicloning site, translational stop codons in all reading frames, t$_0$ and t$_1$ transcriptional terminators, an ampicillin resistance gene (bla), and the ColE1 origin of replication from pBR322. The sequence of the polylinker in relation to the RBS II, 6xHis and t$_0$ regions is shown in FIG. 12B.

The complementary DNA (cDNA) encoding a full-length transcript of the cytoplasmic domain of syntaxin isoform 1A (amino acids 4–267; SEQ ID NO:22) was cloned as a blunt/HindIII fragment into the XbaI (blunted)/HindIII sites of pGEX-KG, resulting in pGST-Syn1A11. The cDNA encoding a full-length VAMP 2 transcript, obtained from the "BLUESCRIPT" KS- VAMP 2 clone described in Calakos, et al., was cloned as an EcoRI/HindIII PCR fragment into the EcoRI/HindIII sites of pGEX-KG, resulting in pGST-VAMP2. The cDNA encoding a full-length n-sec1 transcript, obtained from plasmid K1 (Pevsner, et al., 1994b), was cloned as an NcoI/HindIII fragment into the NcoI/HindIII sites of pGEX-KG, resulting in pGST-n-sec1. Plasmid pQE-9-α-SNAP, containing a cDNA encoding a full-length α-SNAP transcript as a BamHI fragment, and plasmid pQE-9-NSF, containing a cDNA encoding a full-length NSF transcript as a BamHI fragment, were obtained from Dr. J. Rothman (Sloan-Kettering Institute, New York, N.Y.; Whiteheart, et al.).

C. Preparation of Fusion Proteins

Glutathione-S-transferase (GST) fusion proteins of n-sec1, SNAP25, and VAMP were prepared as previously described (Pevsner et al., 1994a). Briefly, coding sequences of the proteins, isolated as described above, were cloned into the pGEX-derived (Smith and Johnson) vector, pGEX-KG (Guan and Dixon), as described above. The resultant vectors were used to transform XL-1 Blue *E. coli* cells (Stratagene, La Jolla, Calif.). Bacterial clones containing the protein sequences were selected and grown at 37° C., with vigorous agitation, for approximately 4 hours in 1-liter of liquid culture (Super Broth; Howard Hughes Media Supply Facility, Stanford University, Stanford, Calif.). 1 ml of 100 mM isopropyl-1-thio-β-D-galactoside (IPTG) was added to induce protein expression, and the culture was incubated for approximately another two hours.

The cells were pelleted and resuspended in 10 ml ice-cold phosphate-buffered saline, lysed with a French Press (SLM Aminco, Rochester, N.Y.) until translucent, centrifuged briefly to pellet cellular debris, and the supernatant transferred to a fresh tube.

Five ml of a 50% (v/v) slurry of pre-swelled glutathione-agarose beads were added to the supernatant and mixed gently for approximately 1 hour at room temperature to allow fusion protein in the supernatant to bind to the beads. The beads were then washed three times to remove any unbound protein. Each wash consisted of adding 10 ml PBS, mixing, and centrifuging in a table-top centrifuge for ~5 minutes at maximum speed (2000×g) to collect the beads.

For some of the experiments described below, the fusion protein remained attached to the beads, while for others, it was eluted using the thrombin cleavage protocol (Ausubel, et al.). Briefly, 10–20 ml of the bead slurry were combined with 10 ml Cleavage Buffer and incubated at 25° C. for about 1 hour. Phenylmethylsulfonyl fluoride (0.6 mM final concentration) was then added to the protein elution, and the sample was concentrated to 0.5 ml using a "CENTRIPREP" concentrator (Amicon Inc., Beverly, Mass.). The protein was further purified by gel filtration on a "SUPEROSE 12" sizing column (Pharmacia, Piscataway, N.J.) in HBS-T20 Buffer. Control preparations were prepared identically from lysates expressing only the GST protein.

His-tagged α-SNAP and NSF were purified as described (Söllner et al., 1993b). Briefly, the coding regions of the sequences were engineered by PCR to contain a BamHI site immediately upstream of the insert initiation ATG codon. The inserts were cloned into the BamHI sites of pQE-9 (Qiagen, Chatsworth, Calif.), described above, and the resulting constructs (Whiteheart, et al.) were transformed into *E. coli* (XL-1 Blue, Stratagene, La Jolla, Calif.). Transformed cells were grown to a density of $A_{660}$=0.8 in super medium (Howard Hughes Media Preparation Facility, Stanford, Calif.) supplemented with 100 μg/ml ampicillin and 50 μg/ml tetracycline. Protein synthesis was induced by treating the cells for 4 hours with 1 mM IPTG.

$His_6$-α-SNAP-expressing cells were collected, washed in Buffer A, disrupted in a French Press, and the suspension was clarified by centrifugation at 100,000 Xg for 1 hour. The supernatant was passed over a Ni-NTA-agarose column (Qiagen; 5 ml bed volume) and the $His_6$-α-SNAP was eluted with a 40 ml, 20–500 mM imidazole gradient in Buffer A. $His_6$-NSF-expressing cells were disrupted in Buffer B. The Ni-NTA-agarose column was eluted with a 50–500 mM imidazole gradient in Buffer C.

Protein concentrations for all of the above-isolated proteins were estimated by Coomassie blue staining of protein bands after sodium dodecyl sulphate polyacrylamide gel electrophoresis (SDS-PAGE) using bovine serum albumin as a standard.

D. Preparation of Anti-α-SNAP and Anti-NSF Antisera

Anti-α-SNAP and anti-NSF antisera were prepared in rabbits with gel-purified His-tagged fusion proteins, prepared as described above, using standard methods (Harlow). Briefly, 250 μg of protein isolated from a polyacrylamide gel was suspended in 1 ml PBS and injected subcutaneously (sc) once every three weeks for 12 weeks. The initial injection contained complete Freund's adjuvant, while subsequent injections contained incomplete Freund's adjuvant. Serum was isolated after 12 weeks and used as described below.

E. SDS-PAGE and Western Blotting

Protein samples were electrophoresed on 12.5% resolving SDS-polyacrylamide (denaturing) gels, transferred to nitrocellulose paper (0.2 μM), and probed with the following antibodies: affinity-purified anti-n-sec1 antiserum (1:1000 dilution; Pevsner et al., 1994a and b), HPC-1 (a monoclonal antibody specific for syntaxin; 1:1000; Inoue et al., 1992), affinity-purified anti-SNAP25 antiserum (1:1000 dilution; Oyler et al., 1989), affinity-purified anti-VAMP antiserum (1:500 dilution, Pevsner et al., 1994a), anti-α-SNAP antiserum and anti-NSF antiserum (for both, 1:5000; prepared as described above). Proteins were visualized by enhanced chemiluminescence (ECL) system (Amersham Corp., Arlington, Heights, Ill.) and/or by autoradiography using $^{125}$I-labeled goat anti-rabbit antibodies as the secondary antibody. Protein bands were quantitated by densitometry and/or phosphor-imaging (Molecular Dynamics, Sunnyvale, Calif.).

F. Construction of Syntaxin 1A Deletion Mutants

Syntaxin 1A deletion mutants were prepared by subcloning syntaxin restriction fragments into pGEX-KG and expressed as GST-fusion proteins in AB1899 cells. The location and identity of restriction sites used in the generating the constructs are presented in Table 1, below. The amino acid numbering scheme is relative to the complete rat syntaxin 1A polypeptide. The sequence presented as SEQ ID NO:1 encodes a rat syntaxin 1A polypeptide that is missing the first three amino acids (i.e., the SEQ ID NO:1 encodes amino acids 4–288 of rat syntaxin 1A).

TABLE 1

CONSTRUCTION OF SYNTAXIN DELETION MUTANTS

| No. | Start | | End | |
|---|---|---|---|---|
| | Amino Acid | Restriction Site | Amino Acid | Restriction Site |
| 1A1 | 8 | EcoRI | 288 | EcoRI (stop) |
| 1A3 | 4 | EcoRI | 288 | EcoRI (stop) |
| 1A4 | 8 | EcoRI | 76 | SstI |
| 1A5 | 4 | EcoRI | 114 | BamHI |
| 1A6 | 4 | EcoRI | 190 | DraII |
| 1A13 | 4 | EcoRI | 221 | BstXI |
| 1A17 | 4 | EcoRI | 240 | DraII |
| 1A11 | 4 | EcoRI | 266 | BclI |
| 1A7 | 77 | SstI | 288 | EcoRI (stop) |
| 1A8 | 115 | BamHI | 288 | EcoRI (stop) |
| 1A9 | 191 | DraII | 288 | EcoRI (stop) |
| 1A16 | 191 | DraII | 266 | BclI |
| 1A12 | 221 | BstXI | 288 | EcoRI (stop) |

G. Construction of Syntaxin 1A Point Mutants cDNA coding for the full-length syntaxin 1A cytoplasmic domain (Syn1A11) was subcloned as a EcoRI/AatII (blunt ended) fragment from pGST-Syn1A11 into the EcoRI/HindIII (blunt ended) restriction sites of "pBLUESCRIPT II SK" (Stratagene, La Jolla, Calif.), resulting in Syn1A11-BS. The construct was transformed into bacterial strain RZ1032 (ung$^-$ dut$^-$) by electroporation, and mutagenized by oligonucleotide-directed mutagenesis as described in Ausubel, et al.

Briefly, Syn1A11-BS construct was transformed into and grown in RZ1032 E. coli strain to obtain single-stranded uracil containing Syn1A11-BS template. In vitro DNA synthesis was then carried out using oligonucleotides containing the desired mutation as the primer. The resulting DNA heteroduplex was transformed into E. coli strain NM522 (Stratagene, LaJolla, Calif.). E. coli colonies containing the mutagenized construct were identified by DNA sequencing.

The point mutants were generated using the oligonucleotides in Table 2, below. The left column indicates the name of the mutant (e.g., M1), and the identities and locations of the mutated amino acids (e.g., R198A indicates that the arginine at position 198 was changed to an alanine). The center column presents the sequence of the oligonucleotide used to generate the mutant, with the residues resulting in the aforementioned changes underlined. The right column indicates the SEQ ID NO that the corresponding oligonucleotide has in the Sequence Listing.

The mutants were screened by restriction enzyme digestion and/or double-stranded DNA sequencing using a Sequenase kit (United States Biochemical, Cleveland, Ohio). Mutagenized syntaxin 1A DNA inserts were subcloned into pGEX-KG, and GST-fusion proteins were expressed in bacterial strain AB1899 (lon$^-$). The fusion proteins were immobilized on glutathione-agarose beads as described above for in vitro binding studies.

H. Surface Plasmon Resonance (SPR) Analysis

SPR detection experiments were performed with the BIAcore Pharmacia Biosensor apparatus (Pharmacia Biotech, Piscataway, N.J.) according to manufacturer's instructions. All protein immobilizations were performed in 25 mM acetate buffer (pH 4.0), 15 mM NaCl, 0.05% Tween-20. The carboxylated dextran matrix of the flow cell was first activated with 1-ethyl-3-(3-dimethylaminopropyl) carbodiimide and N-hydroxysuccinimide, which allowed the subsequent crosslinking of injected protein through primary amine groups (Johnsson, et al.). After the protein was cross-linked to the flow cell, the reactive groups were blocked by the injection of an excess of primary amines, 1M ethanolamine (pH 8.5). Data for BIAcore SPR detection experiments were collected at 5 Hz. All binding was done in HBS-T20 buffer at room temperature.

I. Determination of Binding Kinetic Rate Constants using Surface Plasmon Resonance (SPR) Analysis Rate constants for association and dissociation were determined as follows. The association rate data were fitted to the exponential equation $R_t=[Ck_a R_{max}/(Ck_a+k_d)]\times[1-\exp(-(Ck_a+k_d)/t)]$ (O'Shannessy, et al.) with the "IGOR" non-linear least squares analysis software program (WaveMetrics, Lake Oswego, Oreg.). Variables: $R_t$=resonance units (RU) at time t (seconds); C=concentration of the injected analyte (M); $R_{max}$= maximum RU possible if the analyte bound 100% of the immobilized ligand. In no cases were the residual plots of the difference between the actual data and the predicted data greater than 10 RU, and most residuals were less than 4 RU in magnitude.

EXAMPLE 1

In Vitro Binding Assays

Protein-protein binding was evaluated in vitro as follows. Typical binding incubations consisted of approximately 0.3–2 µM GST-fusion proteins bound to glutathione agarose beads and approximately 1–4 µM soluble recombinant proteins in a total volume of ~50 µl of Buffer D. After a one hour incubation at 4° C. with gentle agitation, the beads were washed once with 200 µl Buffer D containing 1 mg/ml

TABLE 2

MUTATION SITES
(OLIGONUCLEOTIDES USED FOR SITE-DIRECTED MUTAGENESIS)

| | | |
|---|---|---|
| M1: R198A, I202A | GAC CGC GCA CAG TGA GGC CAT CAA GTT GGA (30 mer) | SEQ ID NO:26 |
| M4: V223A, Q226A | GCT GGC GGA GAG CGC GGG GGA GAT GAT T (28 mer) | SEQ ID NO:27 |
| M6: A240V, V244A | ACA CGT TGT GGA CTA CGC GGA GAG GGC CG (29 mer) | SEQ ID NO:28 |
| M2: L205A, I209A | TCA AGG CGG AGA ACA GCG CCC GGG AGC TAC (30 mer) | SEQ ID NO:29 |
| M3: L212A, F216A | GGG AGG CAC ACG ATA TGG CCA TGG ACA TGG (30 mer) | SEQ ID NO:30 |
| M5: I230A, I233A | AGA TGG CTG ACA GGG CCG AGT ACA ATG (27 mer) | SEQ ID NO:31 | gelatin and twice with 200 µl Buffer D containing 5% glycerol. Proteins on the beads were solubilized in 8 µl electrophoresis sample buffer and subjected to SDS-PAGE and Western blotting as described above.

A. Soluble α-SNAP/Immobilized Syn1a, VAMP and SNAP-25

For α-SNAP-binding to various GST-fusion synaptic proteins, 1 µM soluble His-tagged α-SNAP was added to glutathione agarose beads suspended in Suspension Buffer, and containing approximately 1–2 µM of either (i) immobilized GST, (ii) immobilized full cytoplasmic domain of syntaxin 1A (GST-syn1a11), (iii) immobilized full cytoplasmic domain of VAMP (GST-VAMP), or (iv) immobilized GST-SNAP-25. Protein that bound to the beads was eluted with thrombin, subjected to SDS-PAGE (0.3 µg protein per lane) and Western blotting and probed with anti-α-SNAP antiserum as described above. Bound α-SNAP was visualized by ECL and quantitated by densitometry.

Exemplary results of the above experiments are presented in the Western blot illustrated in FIG. 3. A very strong signal was observed in the lane containing material eluted from Syn1a11 beads, with weak to non-existent signals from the other lanes. The densitometry pixel values were 0, 1828, 8 and 33 for α-SNAP bound to GST, Syn1a11, VAMP, and SNAP-25, respectively.

The data indicate that α-SNAP binds relatively strongly to syntaxin and weakly to SNAP-25.

B. Syntaxin Deletion Mutant Binding

Soluble recombinant SNAP-25 (4 µM), α-SNAP (2.5 µM), VAMP (4 µM) or n-sec1 (1 µM) was added to GST-syntaxin deletion mutant fusion proteins (0.3 µM), synthesized as described above, immobilized on the glutathione agarose beads suspended in Suspension Buffer. Bound fusion proteins were eluted, fractionated and visualized and quantitated as described above.

The results are summarized in FIGS. 4A and 4B. Exemplary data are shown in FIG. 4C. FIG. 4A shows a schematic of the 288 amino acid syntaxin 1A polypeptide (N-terminal labeled "1", C-terminal labeled "288" for the first and last amino acid), illustrating the approximate positions of three regions predicted to be in helical conformations (H1, H2, H3). These domains may participate in protein-protein interaction through their coiled-coil motifs. The membrane anchor is illustrated as a hatched region at 20. Above the schematic of syntaxin are four lines, labeled (i), (ii), (iii) and (iv). The lines indicate the domains of syntaxin 1A required for binding of (i) SNAP-25, (ii) α-SNAP, (iii) VAMP and (iv) n-sec1. The lines were drawn based on data presented in FIG. 4C, described below.

FIG. 4B shows schematics of syntaxin 1A deletion mutants relative to the syntaxin polypeptide in FIG. 4A. The names of the mutants are indicated in the column along the left side of the figure. Each mutant is indicated by a line. The numbers of the first and last amino acid represented in each mutant (relative to the intact syntaxin 1A polypeptide in FIG. 4A) are shown above each line.

FIG. 4C presents images of Western blots showing the binding of the four ligands, SNAP-25 (i), α-SNAP (ii), VAMP (iii) and n-sec1 (iv), to the syntaxin mutants, or constructs, shown in FIG. 4B. The pixel values from densitometry analyses of the data in FIG. 4C were (top to bottom) 19, 19, 9, 417, 623, 797, 374, 644 and 24 for bound SNAP25 (i); 0, 0, 0, 0, 1660, 1667, 1440, 846 and 0 for bound α-SNAP (ii); 0, 0, 0, 0, 0, 286, 557, 1097 and 0 for bound VAMP (iii); and 0, 0, 0, 84, 2447, 2037, 26, 114 and 0 for bound n-sec1 (iv).

The results of the analyses are summarized in FIG. 4A. The full-length syntaxin, either with (amino acids 8–288; Syn 1A) or without (amino acids 4–266; Syn 1A11) the membrane anchor (amino acids 267–288), bound to n-sec1, VAMP, SNAP-25 and α-SNAP. As the protein was deleted from the carboxyl terminal end, a progressive loss of binding sites was observed. For example, deletion of amino acids 240–266 (Syn 1A17) resulted in the loss of VAMP binding. Similarly, deletion of the next amino terminal domain, corresponding to amino acids 221–240 (Syn 1A13), resulted in a loss of α-SNAP and n-sec1 binding. Loss of amino acids 190–221 (Syn 1A6) eliminated all binding, as did further upstream deletions from the carboxyl terminal end of syntaxin (Syn 1A4 and Syn 1A5).

The region of syntaxin adjacent the membrane anchor (amino acids 191–266) was necessary and sufficient for the binding of VAMP, SNAP-25 and α-SNAP, but was not sufficient (though still necessary) to bind n-sec1 in the absence of upstream regions. Similarly, regions upstream of H3 were necessary but not sufficient to bind n-sec1.

Accordingly, these data define four overlapping binding sites or domains. SNAP-25 binding requires amino acids 191–221 (SEQ ID NO:21), α-SNAP binding requires amino acids 191–240 (SEQ ID NO:20), VAMP binding requires amino acids 191–266 (SEQ ID NO:19), and n-sec1 binding requires amino acids 4–240.

C. Syntaxin Point Mutant Binding

Soluble recombinant SNAP-25 (1.25 µM), α-SNAP (1 µM), VAMP (2 µM), or n-sec1 (1 µM) protein was added to GST-syntaxin point mutants (0.3 µM) constructed as described above and immobilized on glutathione agarose beads. Bound soluble recombinant proteins were visualized and quantitated as described above.

Data from an exemplary experiment are illustrated in FIGS. 5A and 5B. FIG. 5A shows the sequences of variant syntaxins 1A between amino acids 197 and 253.The top row presents the wild-type sequence, numbered at residues that are different in the mutants. The sequences of point mutants, identified along the left portion as "1", "2", "3", "4", "5", "6", "12", "13", "34" and "45", are presented below the wild type sequence, and are shown only at those residues (typically "A" or "V") which differ from the wild type sequence. The extents of SNAP-25, α-SNAP, n-sec1 and VAMP binding sites, determined as described above, are presented as lines above the wild-type sequence.

The binding data for syntaxin 1A and the point mutants are shown in FIG. 5B. Note that neither n-sec1 nor SNAP-25 were particularly sensitive to these point mutations, whereas α-SNAP and VAMP binding was abolished in all mutants (except mutant 6 for α-SNAP binding). The pixel values from densitometry (from top to bottom) were 555, 586, 672, 866, 754, 824, 875, 361, 143, 712 and 640 for bound SNAP-25; 414, 53, 36, 23, 43, 25, 633, 23, 15, 10 and 7 for bound α-SNAP; 2613, 37, 17, 0, 0, 0, 0, 0, 0, 0 and 0 for bound VAMP; and 1067, 522, 779, 554, 623, 15, 687, 618, 79, 353 and 7 for bound n-sec1.

EXAMPLE 2

Assembly and Disassembly of the 20S Complex in vitro

His-tagged α-SNAP and NSF fusion proteins, and soluble SNAP-25, VAMP and GST-syntaxin 1A fusion proteins immobilized on glutathione agarose beads were prepared as described above, except that thrombin cleavage was carried out in Buffer F. All other incubations were carried out in Buffer E. Soluble fusion proteins were pre-incubated with GST bound to glutathione agarose beads for 0.5 hours at 25° C. prior to incubation with GST-syntaxin 1a beads to decrease the non-specific binding of fusion proteins to GST or glutathione agarose beads.

A. Full Length Syntaxin-1A-11 20S Complexes

The cytoplasmic domain of syntaxin (Syn 1A11) wast expressed as a GST fusion protein and bound to glutathione agarose beads. The 20S complex was formed by incubating 0.3 μM GST-syntaxin fusion proteins (or GST as a control for non-specific fusion protein binding) bound to glutathione agarose beads with 1 μM SNAP-25, 2 μM VAMP, 2 μM α-SNAP and 2 μM NSF (tetramer) in 50 μl Buffer E containing 2 mM EDTA and either 0.5 mM ATP or ATPγS for approximately 30 minutes at 25° C. Following the incubation, the reaction mixture was incubated with 8 mM $MgCl_2$ for 1 hour at 25° C. to dissociate the complex.

The beads were then washed once with 200 μl Buffer E containing 2 mM $MgCl_2$ and twice with 200 μl Buffer E containing 1 mM EDTA at 25° C. The remaining protein complexes were solubilized in 10 μl sample buffer and subjected to SDS-PAGE and Western blotting. The proteins comprising the remaining complexes were dissociated under the denaturing conditions of the SDS-PAGE, and were visualized as bands by Ponceau S staining of the filter (Ausubel, et al.). The blot was reacted with probes to NSF, α-SNAP, SNAP-25 and VAMP (see above), and reactive bands were visualized with enhanced chemiluminescence (ECL, Amersham). Quantitation of the bands was carried out by densitometry (Molecular Dynamics).

Exemplary results are presented in FIG. 6A. When the reaction was carried out in the presence of non-hydrolyzable ATP (either ATPγS or ATP/EDTA), a heteropentameric complex containing GST-syntaxin 1A fusion protein, NSF, α-SNAP, SNAP-25 and VAMP was formed. This complex remained intact during the 1 hour (25° C.) $MgCl_2$ incubation, and all of the individual components were detected (FIG. 6A, first lane from the left). Only the background non-specific binding of NSF was detected using GST alone rather than GST-syntaxin (FIG. 6A, third lane from the left). These results suggest that purified NSF, α-SNAP, SNAP-25 and VAMP, when combined in the presence of ATP, can form the 20S complex, and are sufficient for the assembly of the particle in the absence of other accessory factors.

However, when the reaction was carried out in the presence of (hydrolyzable) ATP, part of the complex dissociated during the 1 hour (25° C.) $MgCl_2$ incubation (FIG. 6A, second lane from the left). Specifically, approximately 80–90% VAMP, 70–90% α-SNAP and 40–80% NSF dissociated from syntaxin following ATP hydrolysis by NSF.

The densitometry results for data illustrated in FIG. 6A were as follows: at 25° C., pixel values for bound NSF, α-SNAP, SNAP-25 and VAMP bound to Syn 1A11 in the presence of ATPγS were 1592, 1487, 839 and 528 respectively; the pixel values for NSF, α-SNAP, SNAP-25 and VAMP bound to Syn 1A11 in the presence of ATP were 362, 132, 768 and 32 respectively.

B. Syntaxin Deletion Mutant 20S Complexes

The experiments described above were carried out with some of the syntaxin deletion mutants shown in FIG. 4B (Syn 1A6, Syn 1A13, Syn 1A17, Syn 1A16), as well as with Syn 1A11, as described above. Exemplary results are illustrated in FIG. 6B.

Syntaxin deletions of the H3 region, constructs 1A5 and 1A6, did not bind any of the components. Deletion mutant syn1A13, encompassing syntaxin residues 4 to 221, contained only the SNAP-25 binding site. This mutant formed a complex with both VAMP and SNAP-25, but not with appreciable amounts of either α-SNAP or NSF (the intensity of the NSF band is consistent with non-specific binding). This profile demonstrates that the complete region necessary for VAMP binding in the dimeric assay may not be necessary in the presence of SNAP-25. In contrast, the α-SNAP binding domain is not present in this syntaxin deletion mutant and, as a result, no significant levels of α-SNAP or NSF binding were observed. The addition of residues between 222 and 240 (deletion mutant Syn 1A17) enabled the binding of α-SNAP and NSF to the complex, but very little dissociation of the complex was observed in the presence of (hydrolyzable) ATP and $Mg^{++}$. Only about 30%, 25%, 0% and 0% of NSF, α-SNAP, SNAP-25 and VAMP, respectively, dissociated from Syn 1A17 under these conditions.

Similarly, the H3 domain construct (deletion mutant 16), spanning residues 191–288, formed a complex that did not dissociate in the presence of (hydrolyzable) ATP and $Mg^{++}$, with only about 11%, 0%, 5% and 0% of NSF, α-SNAP, SNAP-25 and VAMP, respectively, dissociating from Syn 1A16 under these conditions. Complete complex formation and hydrolysis occurred only when the complex was formed on the syntaxin 1All construct, which contains residues 4–266 as discussed above.

The densitometry results for data illustrated in FIG. 6B were as follows: following an 18° C. overnight $MgCl_2$ incubation, the pixel values for bound NSF, α-SNAP, SNAP-25 and VAMP were: 0, 0, 0, and 0, respectively, on Syn 1A6 beads in the presence of ATPγS; 0,0,0, and 0, respectively, on Syn 1A6 beads in the presence of ATP; 46, 0, 1340, and 1312, respectively, on Syn 1A13 beads in the presence of ATPγS; 12, 0, 1312 and 1560, respectively, on Syn 1A13 beads in the presence of ATP; 295, 1071, 415 and 812, respectively, on Syn 1A17 beads in the presence of ATPγS; 198, 793, 546 and 903, respectively, on Syn 1A17 beads in the presence of ATP; 163, 1041, 85 and 691, respectively, on Syn 1A11 beads in the presence of ATPγS; 92, 331, 75 and 133, respectively, on Syn 1A11 beads in the presence of ATP; 319, 1419, 504 and 944, respectively, on Syn 1A16 beads in the presence of ATPγS; and 357, 1542, 484 and 951, respectively, on Syn 1A16 beads in the presence of ATP.

The data described above are consistent with the syntaxin deletion mutant data presented in Example 1, and further demonstrate that amino terminal and carboxyl terminal domains, which may not be required to form the complex, are required for its dissociation. The lack of disassembly may be caused by an inhibition of ATP hydrolysis by NSF, or due to an inhibition of the conformational changes necessary to dissociate VAMP, syntaxin and SNAP-25.

EXAMPLE 3

Surface Plasmon Resonance (SPR) Analysis of VAMP/Syntaxin Binding

Real-time SPR detection of VAMP 2 binding to syntaxin 1A constructs was performed as described above. Constructs encoding the cytoplasmic (amino acids 4–267), amino-terminal (amino acids 4–193), and carboxyl-terminal (amino acids 194–267) domains of syntaxin 1A were generated as described in Bennett, et al., (1993a). A construct encoding the cytoplasmic domain of VAMP 2 (amino acids 1–94) was generated by polymerase chain reaction (PCR). The PCR fragments were directionally cloned into the EcoRI and HindIII sites of the pGEX-KG vector (Guan and Dixon). The VAMP 2 recombinant protein contains the sequence represented as SEQ ID NO:24 at the amino terminus after thrombin cleavage. All fusion proteins were expressed in the AB 1899 strain of *Escherichia coli*.

Exemplary results from SPR experiments are illustrated in FIGS. 9A, 9B and 9C. FIG. 9A shows the resonance units (RU) plotted as a function of time (sensorgrams) for three representative experiments: the carboxyl domain (9 μM; top trace), the cytoplasmic domain (3 μM middle trace), and the amino-terminal domain (8 μM; bottom trace) of syntaxin 1A were injected into a flow cell containing the immobilized cytoplasmic domain of VAMP 2. No interaction was seen with the cytoplasmic or amino-terminal domains at any concentration tested, up to 30 μM. The sharp vertical rise in RU at the beginning and end of the sample injection corresponds to the refractive index change between the sample and the flow buffer.

FIG. 9B shows sensorgrams of the carboxyl-terminal domain of syntaxin 1A binding to VAMP 2 (concentrations (μM) of syntaxin 1A are given to the right of each trace). A total of 2400 RU of VAMP 2 cytoplasmic domain was immobilized to the flow cell. The flow rate was 4 μl min$^{-1}$ during the association phase and 30 μl min$^{-1}$ during the dissociation phase. The higher flow rate during dissociation was chosen to minimize the possibility of analyte rebinding to the immobilized ligand.

FIG. 9C shows a plot of ln($R_t/R_o$) as a function of Δt, a linearizing transformation of the dissociation phase of the carboxyl-terminal domain of syntaxin 1A (5.5 μM) binding to VAMP 2 in the experiment in FIG. 9B ($R_o$=initial response, $R_t$=resonance units at time Δt, the time after the start of dissociation phase). The dissociation rate was obtained by averaging the slopes obtained from such an analysis of six experiments.

SPR was also used to assess whether amino- and carboxyl-terminal domains of syntaxin 1A interact to effect VAMP 2 binding. Exemplary results are shown in FIG. 10A. FIG. 10A shows sensorgrams of syntaxin 1A carboxyl-terminal domain (5.5 μM) binding to immobilized VAMP 2 cytoplasmic domain in the presence of increasing amounts of syntaxin 1A amino-terminal domain (concentrations (μM) are indicated at the right of each trace).

The data were derived by subtraction of the values obtained from the binding of syntaxin 1A to VAMP 2 from that of syntaxin 1A binding to a negative control surface. This manipulation removes the RU change due to the refractive index of the injected sample. The spikes at the start of dissociation are an artifact created by the subtraction, because the injection pulses were not exactly coincident between experiments. The inhibitory constant ($IC_{50}$) of the amino-terminal syntaxin 1A in this experiment was approximately 3 μM. A total of 2400 RU of VAMP 2 cytoplasmic domain was immobilized on the flow cell.

The control surface was an identical immobilization of a lysate expressing GST only, which was prepared as was the VAMP 2 lysate. The samples were preincubated on ice for 2 hours. The injection was 15 μl min$^{-1}$ at room temperature. A control preparation (lysate expressing only GST) when added to the syntaxin 1A carboxyl-terminal domain under identical conditions did not inhibit the binding to VAMP 2, nor did the addition of the syntaxin 1A amino-terminal domain block the interaction of rabbit immunoglobulin G with immobilized protein A.

FIG. 10B shows sensorgrams of syntaxin 1A carboxyl-terminal domain binding to immobilized syntaxin 1A amino-terminal domain. A total of 11,000 RU of syntaxin 1A amino terminal domain was immobilized. The injection was 15 μl min$^{-1}$ at room temperature. Kinetic rate constants (determined as described above) were $k_a$=2.2×10$^3$±0.7× 10$^3$M$^{-1}$ s$^{-1}$ (SEM), n=8; and $k_d$=9×10$^{-3}$±0.8×10$^{-3}$ s$^{-1}$ (SEM), n=8. The $K_D$ was 4.1 μM.

While the invention has been described with reference to specific methods and embodiments, it is appreciated that various modifications and changes may be made without departing from the invention.

---

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
    ( A ) LENGTH: 2097 base pairs
    ( B ) TYPE: nucleic acid
    ( C ) STRANDEDNESS: double
    ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
    ( C ) INDIVIDUAL ISOLATE: Rat syntaxin 1A 3'end (encoding amino
      acids 4-288; GenBank M95734)

( i x ) FEATURE:
    ( A ) NAME/KEY: CDS
    ( B ) LOCATION: 2..859

( x i ) SEQUENCE DESCRIPTION: SEQ ID NO:1:

C CGA ACC CAG GAG CTC CGC ACG GCC AAG GAC AGC GAT GAC GAC GAT    4 6

```
    Arg  Thr  Gln  Glu  Leu  Arg  Thr  Ala  Lys  Asp  Ser  Asp  Asp  Asp  Asp
     1              5                        10                       15

GAT  GTC  ACT  GTC  ACT  GTG  GAC  CGA  GAC  CGC  TTC  ATG  GAT  GAG  TTC  TTT              94
    Asp  Val  Thr  Val  Thr  Val  Asp  Arg  Asp  Arg  Phe  Met  Asp  Glu  Phe  Phe
                        20                        25                      30

GAA  CAG  GTG  GAA  GAG  ATC  CGG  GGC  TTT  ATT  GAC  AAG  ATT  GCT  GAA  AAC             142
    Glu  Gln  Val  Glu  Glu  Ile  Arg  Gly  Phe  Ile  Asp  Lys  Ile  Ala  Glu  Asn
                   35                        40                      45

GTG  GAG  GAG  GTG  AAG  AGG  AAA  CAC  AGC  GCC  ATC  CTG  GCC  TCC  CCG  AAC             190
    Val  Glu  Glu  Val  Lys  Arg  Lys  His  Ser  Ala  Ile  Leu  Ala  Ser  Pro  Asn
                   50                        55                      60

CCC  GAT  GAG  AAG  ACC  AAG  GAG  GAA  CTG  GAG  GAG  CTC  ATG  TCG  GAC  ATT             238
    Pro  Asp  Glu  Lys  Thr  Lys  Glu  Glu  Leu  Glu  Glu  Leu  Met  Ser  Asp  Ile
              65                        70                      75

AAG  AAG  ACA  GCG  AAC  AAA  GTT  CGC  TCC  AAG  CTA  AAG  AGC  ATC  GAG  CAG             286
    Lys  Lys  Thr  Ala  Asn  Lys  Val  Arg  Ser  Lys  Leu  Lys  Ser  Ile  Glu  Gln
         80                        85                      90                       95

AGC  ATC  GAG  CAG  GAG  GAA  GGT  CTG  AAC  CGC  TCG  TCG  GCG  GAC  CTG  AGG             334
    Ser  Ile  Glu  Gln  Glu  Glu  Gly  Leu  Asn  Arg  Ser  Ser  Ala  Asp  Leu  Arg
                        100                       105                     110

ATC  CGG  AAG  ACG  CAG  CAT  TCC  ACG  CTG  TCC  CGA  AAG  TTT  GTG  GAG  GTC             382
    Ile  Arg  Lys  Thr  Gln  His  Ser  Thr  Leu  Ser  Arg  Lys  Phe  Val  Glu  Val
                   115                       120                     125

ATG  TCC  GAG  TAC  AAC  GCC  ACT  CAG  TCA  GAC  TAC  CGA  GAA  CGC  TGC  AAA             430
    Met  Ser  Glu  Tyr  Asn  Ala  Thr  Gln  Ser  Asp  Tyr  Arg  Glu  Arg  Cys  Lys
              130                       135                     140

GGG  CGC  ATC  CAG  AGG  CAG  CTG  GAG  ATC  ACT  GGC  CGG  ACC  ACG  ACC  AGT             478
    Gly  Arg  Ile  Gln  Arg  Gln  Leu  Glu  Ile  Thr  Gly  Arg  Thr  Thr  Thr  Ser
         145                       150                     155

GAG  GAG  TTG  GAA  GAC  ATG  CTG  GAG  AGT  GGG  AAT  CCC  GCC  ATC  TTT  GCC             526
    Glu  Glu  Leu  Glu  Asp  Met  Leu  Glu  Ser  Gly  Asn  Pro  Ala  Ile  Phe  Ala
    160                       165                     170                     175

TCT  GGG  ATC  ATC  ATG  GAC  TCC  AGC  ATC  TCG  AAG  CAG  GCC  CTC  AGT  GAG             574
    Ser  Gly  Ile  Ile  Met  Asp  Ser  Ser  Ile  Ser  Lys  Gln  Ala  Leu  Ser  Glu
                        180                       185                     190

ATC  GAG  ACC  AGG  CAC  AGT  GAG  ATC  ATC  AAG  TTG  GAG  AAC  AGC  ATC  CGG             622
    Ile  Glu  Thr  Arg  His  Ser  Glu  Ile  Ile  Lys  Leu  Glu  Asn  Ser  Ile  Arg
                   195                       200                     205

GAG  CTA  CAC  GAT  ATG  TTC  ATG  GAC  ATG  GCC  ATG  CTG  GTG  GAG  AGC  CAG             670
    Glu  Leu  His  Asp  Met  Phe  Met  Asp  Met  Ala  Met  Leu  Val  Glu  Ser  Gln
              210                       215                     220

GGG  GAG  ATG  ATT  GAC  AGG  ATC  GAG  TAC  AAT  GTG  GAA  CAC  GCT  GTG  GAC             718
    Gly  Glu  Met  Ile  Asp  Arg  Ile  Glu  Tyr  Asn  Val  Glu  His  Ala  Val  Asp
         225                       230                     235

TAC  GTG  GAG  AGG  GCC  GTG  TCT  GAC  ACC  AAG  AAG  GCC  GTC  AAG  TAC  CAG             766
    Tyr  Val  Glu  Arg  Ala  Val  Ser  Asp  Thr  Lys  Lys  Ala  Val  Lys  Tyr  Gln
    240                       245                     250                     255

AGC  AAG  GCA  CGC  AGG  AAG  AAG  ATC  ATG  ATC  ATC  ATT  TGC  TGT  GTG  ATT             814
    Ser  Lys  Ala  Arg  Arg  Lys  Lys  Ile  Met  Ile  Ile  Ile  Cys  Cys  Val  Ile
                        260                       265                     270

CTG  GGC  ATC  ATC  ATC  GCC  TCC  ACC  ATC  GGG  GGC  ATC  TTT  GGA  TAGAAACCAC           866
    Leu  Gly  Ile  Ile  Ile  Ala  Ser  Thr  Ile  Gly  Gly  Ile  Phe  Gly
                        275                       280                  285

CCCACCCACG GCTCCATTCT GGATGGGTCT CCTGAGGAGG CCCCTGGCTG CTGCACCTAG             926

CTGGGTTGCC CTCCCCACTC CTGCCTTCTG GCTGGGAGTC CTTTTCCCTC CCATCCAACA             986

CCGCTCCCTC TCTGCCATGA GGCTCCCGTG CCCACCACCC TGCCCCAAGC CGTGTCGTGT            1046

GCATGATCTT GTGACAGTGT GTGTCTGTAC AGGAGGCAGA GGGGAGCAGG ATCGGGAACA            1106

GCCAGAGGGG CTGGGTACAG GCCAGTGTGG GCAAGACTCG GGCCCTGGCA GGTCCGCCTT            1166
```

-continued

```
CCTTCAGGCC TGGGGCTACG CTTCCCTGGG ACTCAGGCTC CTTTCTGGAC CCCAACCTTG     1226
CCCTCACTCG CCCTGCCCTC TGGCTTCCTC AGCTCTCCCC ACCATGCCAA GGCACCTGGA     1286
GGGTGGGGAC CAGCTGGTCA CATGGTGCTG CTTTTCAGGT TAGGGGTGGG GACAGCTCAG     1346
CACTGAGTCT TTGTTAGCTG CCCACTGCCA GGATGCTCAG GGTGCCACGG CTGCTGGTGT     1406
GCTAGGAGCA CCCAGTACCC CTCTTTGGCA AAGCCTGACA GTGTCTCTGG CCTCAGCTGC     1466
CCTTACCACA GCCCTGGGAG TCCTGTTCCT GGGCTGGGCC TGAGCCTAGT GATCCTTTGC     1526
TAAGAAGCTC AGTGGTGCCA TCTCCAGCCT TGCTCTGAGC TGGAGAGGTG GAGCAGGCCA     1586
TAGTCCTCTG CCCACAGTCT CTAACGGGCA TGTTAAGTCG TGGCCGGAGT TGCATGTTAG     1646
GGACAGCGGT TCCCTGCTCC CTTTCTGCTC TGAAAAGCCA GGTGTCACTT TGGGCCTGCA     1706
GTCTCACCCT GCCCTGTCTC CCATTGATGT GCCACGTGGT GTCAGGTGTA CTGGATGCAG     1766
TATTCAGCAG CCAGCTGGGG AGGGGCTCC CCACTTTCCT CCCCTGCCAA CTTGGGGCTT      1826
CTCAGAGTCA AAAATGTACC CCCATGCCCC AGGACCCCTT TCTCATCCAC AGGCAAGGAG     1886
TATGCATGCG ACTGCATGCA GCGGGAGCTG GGGCCGTGTC TGTGTGCCCC TTCCCCTNCG     1946
CTTTGCTCCT GCCCAGTGAC TGACCACTGT CCGTGCTGCC TTCTCTCATG GCCACTTCCC     2006
TTTACCCCAT CACCAAAGGT CTCGGTACAA CCAGCTGCCC ATTTTGTGAG ATTTTTATGT     2066
AGAATAAACA TTTGTATCTG GAAAAAAAA A                                     2097
```

( 2 ) INFORMATION FOR SEQ ID NO:2:

( i ) SEQUENCE CHARACTERISTICS:
        ( A ) LENGTH: 285 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Arg Thr Gln Glu Leu Arg Thr Ala Lys Asp Ser Asp Asp Asp Asp
 1               5                  10                  15

Val Thr Val Thr Val Asp Arg Asp Arg Phe Met Asp Glu Phe Glu
                20                  25                  30

Gln Val Glu Glu Ile Arg Gly Phe Ile Asp Lys Ile Ala Glu Asn Val
                35                  40                  45

Glu Glu Val Lys Arg Lys His Ser Ala Ile Leu Ala Ser Pro Asn Pro
50                       55                  60

Asp Glu Lys Thr Lys Glu Glu Leu Glu Glu Leu Met Ser Asp Ile Lys
65                       70                  75                  80

Lys Thr Ala Asn Lys Val Arg Ser Lys Leu Lys Ser Ile Glu Gln Ser
                85                  90                  95

Ile Glu Gln Glu Glu Gly Leu Asn Arg Ser Ser Ala Asp Leu Arg Ile
                100                 105                 110

Arg Lys Thr Gln His Ser Thr Leu Ser Arg Lys Phe Val Glu Val Met
                115                 120                 125

Ser Glu Tyr Asn Ala Thr Gln Ser Asp Tyr Arg Glu Arg Cys Lys Gly
130                      135                 140

Arg Ile Gln Arg Gln Leu Glu Ile Thr Gly Arg Thr Thr Thr Ser Glu
145                      150                 155                 160

Glu Leu Glu Asp Met Leu Glu Ser Gly Asn Pro Ala Ile Phe Ala Ser
                165                 170                 175

Gly Ile Ile Met Asp Ser Ser Ile Ser Lys Gln Ala Leu Ser Glu Ile
                180                 185                 190
```

```
Glu Thr Arg His Ser Glu Ile Ile Lys Leu Glu Asn Ser Ile Arg Glu
        195                 200                 205

Leu His Asp Met Phe Met Asp Met Ala Met Leu Val Glu Ser Gln Gly
    210                 215                 220

Glu Met Ile Asp Arg Ile Glu Tyr Asn Val Glu His Ala Val Asp Tyr
225                 230                 235                 240

Val Glu Arg Ala Val Ser Asp Thr Lys Lys Ala Val Lys Tyr Gln Ser
            245                 250                 255

Lys Ala Arg Arg Lys Lys Ile Met Ile Ile Ile Cys Cys Val Ile Leu
            260                 265                 270

Gly Ile Ile Ile Ala Ser Thr Ile Gly Gly Ile Phe Gly
        275                 280                 285
```

(2) INFORMATION FOR SEQ ID NO:3:

(i) SEQUENCE CHARACTERISTICS:
        (A) LENGTH: 3000 base pairs
        (B) TYPE: nucleic acid
        (C) STRANDEDNESS: double
        (D) TOPOLOGY: unknown (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Rat syntaxin 1B (GenBank M95735)

(ix) FEATURE:
        (A) NAME/KEY: CDS
        (B) LOCATION: 211..1077

(xi) SEQUENCE DESCRIPTION: SEQ ID NO:3:

```
ATCGCCACCG CAGCCTAGGC AGAGCCAGTC GGCCCAGGCC CCTGTCTCTG CCTGGCCTCA        60

GCTCCCCGCC GGCCCGCCGC GCACCTTACC CGCACATCCC TTGGAGGTCT AGCCGGGTGC       120

CCCCAGACCC CGGCCTCCAG CACAGAGGCA AGAGGCAGAG AGCAGCAGCG AGGGCGAGGA       180

CGAAGAAGGG GAGGAGGAGC TCGTCGCAGG ATG AAG GAT CGG ACT CAG GAG CTG       234
                                  Met Lys Asp Arg Thr Gln Glu Leu
                                    1               5

CGG AGT GCA AAA GAC AGT GAC GAT GAA GAG GAA GTG GTT CAT GTG GAT       282
Arg Ser Ala Lys Asp Ser Asp Asp Glu Glu Glu Val Val His Val Asp
        10              15                  20

CGA GAC CAC TTT ATG GAT GAG TTC TTT GAG CAG GTG GAA GAG ATC CGA       330
Arg Asp His Phe Met Asp Glu Phe Phe Glu Gln Val Glu Glu Ile Arg
 25              30                  35                  40

GGC TGC ATC GAG AAA CTG TCC GAG GAT GTG GAG CAA GTG AAG AAA CAG       378
Gly Cys Ile Glu Lys Leu Ser Glu Asp Val Glu Gln Val Lys Lys Gln
                45                  50                  55

CAC AGT GCC ATT CTT GCT GCC CCC AAC CCC GAT GAG AAG ACT AAA CAG       426
His Ser Ala Ile Leu Ala Ala Pro Asn Pro Asp Glu Lys Thr Lys Gln
            60                  65                  70

GAG CTG GAG GAC CTC ACG GCA GAC ATC AAA AAG ACG GCA AAC AAG GTC       474
Glu Leu Glu Asp Leu Thr Ala Asp Ile Lys Lys Thr Ala Asn Lys Val
        75                  80                  85

CGG TCC AAG TTG AAA GCG ATC GAG CAG AGC ATT GAG CAG GAA GAG GGG       522
Arg Ser Lys Leu Lys Ala Ile Glu Gln Ser Ile Glu Gln Glu Glu Gly
 90                  95                 100

TTG AAT CGT TCT TCT GCA GAC CTG CGT ATC CGT AAG ACC CAG CAC TCC       570
Leu Asn Arg Ser Ser Ala Asp Leu Arg Ile Arg Lys Thr Gln His Ser
105                 110                 115                 120
```

```
ACA CTC TCA CGG AAG TTC GTG GAG GTA ATG ACC GAA TAT AAT GCA ACT    618
Thr Leu Ser Arg Lys Phe Val Glu Val Met Thr Glu Tyr Asn Ala Thr
            125                 130                 135

CAG TCT AAG TAC CGG GAC CGC TGC AAG GAC CGT ATC CAG AGG CAG CTG    666
Gln Ser Lys Tyr Arg Asp Arg Cys Lys Asp Arg Ile Gln Arg Gln Leu
            140                 145                 150

GAG ATC ACT GGC AGG ACT ACT ACC AAC GAA GAG CTG GAA GAC ATG TTG    714
Glu Ile Thr Gly Arg Thr Thr Thr Asn Glu Glu Leu Glu Asp Met Leu
            155                 160                 165

GAA AGC GGG AAG CTG GCC ATC TTC ACG GAC GAC ATC AAA ATG GAC TCG    762
Glu Ser Gly Lys Leu Ala Ile Phe Thr Asp Asp Ile Lys Met Asp Ser
        170                 175                 180

CAG ATG ACA AAG CAA GCC CTG AAT GAG ATA GAG ACA AGG CAC AAT GAG    810
Gln Met Thr Lys Gln Ala Leu Asn Glu Ile Glu Thr Arg His Asn Glu
185                 190                 195                 200

ATC ATC AAA CTG GAA ACC AGC ATC CGA GAG CTG CAC GAC ATG TTT GTG    858
Ile Ile Lys Leu Glu Thr Ser Ile Arg Glu Leu His Asp Met Phe Val
            205                 210                 215

GAC ATG GCC ATG CTC GTG GAG AGC CAG GGT GAG ATG ATC GAC CGA ATT    906
Asp Met Ala Met Leu Val Glu Ser Gln Gly Glu Met Ile Asp Arg Ile
            220                 225                 230

GAG TAC AAT GTG GAA CAT TCT GTG GAC TAC GTG GAG CGA GCC GTG TCC    954
Glu Tyr Asn Val Glu His Ser Val Asp Tyr Val Glu Arg Ala Val Ser
            235                 240                 245

GAC ACC AAG AAA GCT GTG AAA TAT CAG AGC AAG GCC AGG AGG AAG AAA   1002
Asp Thr Lys Lys Ala Val Lys Tyr Gln Ser Lys Ala Arg Arg Lys Lys
        250                 255                 260

ATT ATG ATC ATC ATT TGC TGT GTG GTG CTG GGG GTG GTC TTG GCG TCA   1050
Ile Met Ile Ile Ile Cys Cys Val Val Leu Gly Val Val Leu Ala Ser
265                 270                 275                 280

TCT ATT GGG GGG ACA CTG GGC TTG TAGGCCCCTA CCCTTCTCTT CCCCAGGACC  1104
Ser Ile Gly Gly Thr Leu Gly Leu
            285

CTCCCCACAC ATCGGGAGCA ATACCCCCAC CACCCTTTCA CTCTTTCCCC TGCTCCAAGC 1164
TCACTCCCAA AACAGACCCA GGCAGTTCCA GCCTCTCTCA CCCTCACGCA GACCCTGGAG 1224
TCCCTGGCTC TCACCTTGCC ATGGATCCCC CTCCACCTTG CCGCACATAG ATAGCAGCAG 1284
GCGTGATCAC ACATGCACAC CAACATGCAT GCCGAGGGCA CATGCTCAAG ACGTGTGGAC 1344
ACCCCAGCGT GTGTGTACTT GTGTAGATGT ATGTAGATGC CCTGAACCTC TTCTTGCTGC 1404
CACCTTCATC CTGTGTGGTC TGAACTTCCC TCTCTAGCCG GTTCTGTGCT GACTGTAGCA 1464
GCCTACCATG GCCCAACCTG TTCTGTGTGA ATAGACATGG TGTGTATGTG TGTGTGTGTG 1524
TGTGTGTGTG TGTGTGTGTG TGTGTGTGTG TGTGTAGATC TGTGCCCATA CAATGTATGT 1584
ACATGGAGTT TTGTGAATGT GAAAACCCAA AGCATTTCCT CCACCTTCTC TCCTATCTGT 1644
TACATTTGGA GTGGGAGGCA TATGTGAGGA TAATTTACAT TCTCAGAGGA TCCAGGGTGG 1704
CCCGGTGACC ATGCCACACA TCTTTTGTGA TGTAGAACAA ACTTTCCTGG CTTGGTTACT 1764
GCCAGGGGTC ACATCATGTC CTGAGGATTC TCTCTCTCAG CCTCTCTCTC TGTCTCTCTG 1824
TCCCTCAGTC TCTGTCTCTG TCTCTGTCTC TGTGTGTGTG TGTGTGTGTG TGTGTGTGTG 1884
TGTGTCCACA TGTATGTAAC CCCTAGATTA GCTGTGCTGA GGAAGGAGGC TGCCTGTCCA 1944
TTCCAGAATA TTCTGCTGCA GGGCCCAGCA CCTCCTGCCC CCACCTTGGC TTCTTTGGAG 2004
ATGTCAGAGG AGGCCCCAGG ATCTAGTTCC CTTCTTCTTT CAGCCCAGCC AGAACTCCCA 2064
TTAACTCAGA TGTTTCTAGC AGCCTCCCTG ACACCCCAGT CATGGTGTTC ACAAGGACAG 2124
GGCTGTGGCT GGCATGCTGC TCCTGCCTCT TTGAATGGCA CTGGGCCCAC AGCTGCCCAC 2184
```

```
CACTGAGCCT CAAACAGATG AGCCGTCCCT GAGAGTCTGC TGTAACCCAG CTTTCTAAGA    2244
CCCACACCTC ACACGATGGA CATGTTCGTT GACTGCTGTC CACATGTGTA TCCTGGATGG    2304
TTGTCTGGGG GCTGGTGTCT GTTGCATGTT CTCAGATGTG TGCTGCGTGC CCTCCACACA    2364
CCCCAAACCA TCAAGCCCAA TTATACTCCC TTGGTGGTCC CAGGCCCAAG CCAGGACTCA    2424
ATGCTTCCAT TCTCCCTTTC CTTGCCTCTT ACAAAGCACC TGCGTGTCCA TCTCATGTGC    2484
CCATGGGTCA TCATGCTCCC GTCATACCTT GAGCGTGTAC ACATGTGTGT TCTATGCACT    2544
CGCCCTGCCC TACCTACCCA ACAGAGGACA AGATGGTCGG CCCCTAGCTC CCTTCTCCCC    2604
CACCTAGCCT TTCCCCACGC CCTGCTGTGC AGCTGTGTGC GTTGGTGTGT TTCTGTGTCG    2664
CTGGCGTGTC ATGTGATGTA GCCATGTTTG CTGACATGAG CCCCTGCCCC CTTCTCTTTT    2724
TCTCCATTGG TTTCTAGAAC TCTCTTCCTC CCCTCCCTG AGGGACAGGA CTCCTGGGGC    2784
CTAGCTGGGG GCCCGAGCCT GGCCACCCTC CTGTTAGCCC TCAGAGTCTT ATTTCTCTCT    2844
ATTGGTGACC AAGTTGCAAA TGGATAAAAT ACAGGAAATT CTGACCCCCT GCCCCAGACC    2904
TGCATGTCCT GTCCCCAGTG CCCCCGAACC CCATCCTGGG CCGGGTTGGG CCTGGTGGGA    2964
CGGGAGAAAT AGCAACTAAT CCAACAGCGA AAAAAA                              3000
```

( 2 ) INFORMATION FOR SEQ ID NO:4:

( i ) SEQUENCE CHARACTERISTICS:
        ( A ) LENGTH: 288 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Lys Asp Arg Thr Gln Glu Leu Arg Ser Ala Lys Asp Ser Asp Asp
 1               5                  10                  15
Glu Glu Glu Val Val His Val Asp Arg Asp His Phe Met Asp Glu Phe
            20                  25                  30
Phe Glu Gln Val Glu Glu Ile Arg Gly Cys Ile Glu Lys Leu Ser Glu
        35                  40                  45
Asp Val Glu Gln Val Lys Lys Gln His Ser Ala Ile Leu Ala Ala Pro
    50                  55                  60
Asn Pro Asp Glu Lys Thr Lys Gln Glu Leu Glu Asp Leu Thr Ala Asp
65                  70                  75                  80
Ile Lys Lys Thr Ala Asn Lys Val Arg Ser Lys Leu Lys Ala Ile Glu
                85                  90                  95
Gln Ser Ile Glu Gln Glu Glu Gly Leu Asn Arg Ser Ser Ala Asp Leu
            100                 105                 110
Arg Ile Arg Lys Thr Gln His Ser Thr Leu Ser Arg Lys Phe Val Glu
        115                 120                 125
Val Met Thr Glu Tyr Asn Ala Thr Gln Ser Lys Tyr Arg Asp Arg Cys
    130                 135                 140
Lys Asp Arg Ile Gln Arg Gln Leu Glu Ile Thr Gly Arg Thr Thr Thr
145                 150                 155                 160
Asn Glu Glu Leu Glu Asp Met Leu Glu Ser Gly Lys Leu Ala Ile Phe
                165                 170                 175
Thr Asp Asp Ile Lys Met Asp Ser Gln Met Thr Lys Gln Ala Leu Asn
            180                 185                 190
Glu Ile Glu Thr Arg His Asn Glu Ile Ile Lys Leu Glu Thr Ser Ile
        195                 200                 205
```

| | | | | | | | | | | | | | | | |
|---|---|---|---|---|---|---|---|---|---|---|---|---|---|---|---|
| Arg | Glu | Leu | His | Asp | Met | Phe | Val | Asp | Met | Ala | Met | Leu | Val | Glu | Ser |
| | | 210 | | | | 215 | | | | 220 | | | | | |
| Gln | Gly | Glu | Met | Ile | Asp | Arg | Ile | Glu | Tyr | Asn | Val | Glu | His | Ser | Val |
| 225 | | | | | 230 | | | | 235 | | | | | | 240 |
| Asp | Tyr | Val | Glu | Arg | Ala | Val | Ser | Asp | Thr | Lys | Lys | Ala | Val | Lys | Tyr |
| | | | | 245 | | | | | 250 | | | | | 255 | |
| Gln | Ser | Lys | Ala | Arg | Arg | Lys | Lys | Ile | Met | Ile | Ile | Ile | Cys | Cys | Val |
| | | | 260 | | | | | 265 | | | | | 270 | | |
| Val | Leu | Gly | Val | Val | Leu | Ala | Ser | Ser | Ile | Gly | Gly | Thr | Leu | Gly | Leu |
| | | 275 | | | | | 280 | | | | | 285 | | | |

( 2 ) INFORMATION FOR SEQ ID NO:5:

( i ) SEQUENCE CHARACTERISTICS:
        ( A ) LENGTH: 911 base pairs
        ( B ) TYPE: nucleic acid
        ( C ) STRANDEDNESS: double
        ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Rat syntaxin 2 (GenBank L20823)

( i x ) FEATURE:
        ( A ) NAME/KEY: CDS
        ( B ) LOCATION: 1..873

( x i ) SEQUENCE DESCRIPTION: SEQ ID NO:5:

| | | | | | | | | | | | | | | | | |
|---|---|---|---|---|---|---|---|---|---|---|---|---|---|---|---|---|
| ATG | CGG | GAC | CGG | CTG | CCG | GAC | CTC | ACG | GCG | TGT | AGG | AAA | AGC | GAC | GAT | 48 |
| Met | Arg | Asp | Arg | Leu | Pro | Asp | Leu | Thr | Ala | Cys | Arg | Lys | Ser | Asp | Asp | |
| 1 | | | | 5 | | | | | 10 | | | | | 15 | | |
| GGA | GAC | AAT | GCT | GTC | ATC | ATC | ACG | GTG | GAG | AAG | GAC | CAC | TTC | ATG | GAT | 96 |
| Gly | Asp | Asn | Ala | Val | Ile | Ile | Thr | Val | Glu | Lys | Asp | His | Phe | Met | Asp | |
| | | | 20 | | | | | 25 | | | | | 30 | | | |
| GCC | TTC | TTC | CAT | CAG | GTG | GAG | GAG | ATT | CGA | AGC | AGC | ATA | GCC | AGG | ATT | 144 |
| Ala | Phe | Phe | His | Gln | Val | Glu | Glu | Ile | Arg | Ser | Ser | Ile | Ala | Arg | Ile | |
| | | 35 | | | | | 40 | | | | | 45 | | | | |
| GCT | CAG | CAC | GTG | GAG | GAT | GTG | AAG | AAG | AAC | CAC | AGC | ATC | ATC | CTC | TCT | 192 |
| Ala | Gln | His | Val | Glu | Asp | Val | Lys | Lys | Asn | His | Ser | Ile | Ile | Leu | Ser | |
| | 50 | | | | | 55 | | | | | 60 | | | | | |
| GCC | CCA | AAC | CCA | GAA | GGA | AAA | ATA | AAA | GAA | GAG | CTG | GAG | GAC | CTG | AAC | 240 |
| Ala | Pro | Asn | Pro | Glu | Gly | Lys | Ile | Lys | Glu | Glu | Leu | Glu | Asp | Leu | Asn | |
| 65 | | | | 70 | | | | | 75 | | | | | 80 | | |
| AAA | GAG | ATC | AAG | AAA | ACT | GCT | AAC | AGG | ATC | CGG | GGC | AAG | CTG | AAG | GCT | 288 |
| Lys | Glu | Ile | Lys | Lys | Thr | Ala | Asn | Arg | Ile | Arg | Gly | Lys | Leu | Lys | Ala | |
| | | | | 85 | | | | | 90 | | | | | 95 | | |
| ATT | GAG | CAG | AGT | TGT | GAT | CAG | GAC | GAG | AAT | GGG | AAC | CGA | ACT | TCA | GTG | 336 |
| Ile | Glu | Gln | Ser | Cys | Asp | Gln | Asp | Glu | Asn | Gly | Asn | Arg | Thr | Ser | Val | |
| | | | 100 | | | | | 105 | | | | | 110 | | | |
| GAT | CTG | CGG | ATA | CGA | AGG | ACC | CAG | CAC | TCA | GTG | CTG | TCA | CGG | AAG | TTT | 384 |
| Asp | Leu | Arg | Ile | Arg | Arg | Thr | Gln | His | Ser | Val | Leu | Ser | Arg | Lys | Phe | |
| | | 115 | | | | | 120 | | | | | 125 | | | | |
| GTG | GAC | GTC | ATG | ACA | GAA | TAC | AAT | GAA | GCA | CAG | ATC | CTG | TTT | CGG | GAG | 432 |
| Val | Asp | Val | Met | Thr | Glu | Tyr | Asn | Glu | Ala | Gln | Ile | Leu | Phe | Arg | Glu | |
| | 130 | | | | | 135 | | | | | 140 | | | | | |
| CGA | AGC | AAA | GGC | CGA | ATC | CAG | CGC | CAG | CTA | GAG | ATC | ACT | GGG | AGG | ACC | 480 |
| Arg | Ser | Lys | Gly | Arg | Ile | Gln | Arg | Gln | Leu | Glu | Ile | Thr | Gly | Arg | Thr | |
| 145 | | | | | 150 | | | | | 155 | | | | | 160 | |
| ACC | ACT | GAC | GAG | GAG | CTG | GAG | GAG | ATG | CTG | GAG | AGC | GGG | AAG | CCG | TCC | 528 |

|  |  |  |  |  |  |  |  |  |  |  |  |  |  |  |  |  |
|---|---|---|---|---|---|---|---|---|---|---|---|---|---|---|---|---|
| Thr | Thr | Asp | Glu | Glu<br>165 | Leu | Glu | Glu | Met | Leu<br>170 | Glu | Ser | Gly | Lys | Pro<br>175 | Ser | |

```
ATC TTC ATC TCG GAC ATT ATA TCA GAT TCA CAG ATT ACT AGG CAA GCT        576
Ile Phe Ile Ser Asp Ile Ile Ser Asp Ser Gln Ile Thr Arg Gln Ala
        180                     185                     190

CTC AAT GAG ATC GAG TCA CGC CAC AAA GAC ATC ATG AAG CTG GAG ACC        624
Leu Asn Glu Ile Glu Ser Arg His Lys Asp Ile Met Lys Leu Glu Thr
        195                     200                     205

AGC ATC CGA GAG CTG CAC GAG ATG TTC ATG GAT ATG GCC ATG TTT GTC        672
Ser Ile Arg Glu Leu His Glu Met Phe Met Asp Met Ala Met Phe Val
        210                     215                     220

GAG ACT CAG GGT GAA ATG GTC AAC AAC ATT GAG AGA AAC GTG GTG AAC        720
Glu Thr Gln Gly Glu Met Val Asn Asn Ile Glu Arg Asn Val Val Asn
225                     230                     235                 240

TCC GTA GAT TAC GTG GAG CAC GCC AAG GAA GAG ACT AAG AAA GCC ATC        768
Ser Val Asp Tyr Val Glu His Ala Lys Glu Glu Thr Lys Lys Ala Ile
                245                     250                     255

AAA TAC CAG AGC AAG GCC AGA CGG AAA AAG TGG ATA ATT GCT GCT GTG        816
Lys Tyr Gln Ser Lys Ala Arg Arg Lys Lys Trp Ile Ile Ala Ala Val
            260                     265                     270

GTG GTG GCT GTC ATT GCT GTC CTG GCT CTA ATC ATT GGC TTG ACG GTT        864
Val Val Ala Val Ile Ala Val Leu Ala Leu Ile Ile Gly Leu Thr Val
        275                     280                     285

GGC AAA TGATTGCGTA GATGGCGCTG GGTGCTTGCC TCTCCCTCAG G                  911
Gly Lys
290
```

( 2 ) INFORMATION FOR SEQ ID NO:6:

( i ) SEQUENCE CHARACTERISTICS:
        ( A ) LENGTH: 290 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

|  |  |  |  |  |  |  |  |  |  |  |  |  |  |  |  |
|---|---|---|---|---|---|---|---|---|---|---|---|---|---|---|---|
| Met<br>1 | Arg | Asp | Arg | Leu<br>5 | Pro | Asp | Leu | Thr | Ala<br>10 | Cys | Arg | Lys | Ser | Asp<br>15 | Asp |
| Gly | Asp | Asn | Ala<br>20 | Val | Ile | Ile | Thr | Val<br>25 | Glu | Lys | Asp | His | Phe<br>30 | Met | Asp |
| Ala | Phe | Phe<br>35 | His | Gln | Val | Glu | Glu<br>40 | Ile | Arg | Ser | Ser | Ile<br>45 | Ala | Arg | Ile |
| Ala | Gln<br>50 | His | Val | Glu | Asp | Val<br>55 | Lys | Lys | Asn | His | Ser<br>60 | Ile | Ile | Leu | Ser |
| Ala<br>65 | Pro | Asn | Pro | Glu | Gly<br>70 | Lys | Ile | Lys | Glu | Glu<br>75 | Leu | Glu | Asp | Leu | Asn<br>80 |
| Lys | Glu | Ile | Lys | Lys<br>85 | Thr | Ala | Asn | Arg | Ile<br>90 | Arg | Gly | Lys | Leu | Lys<br>95 | Ala |
| Ile | Glu | Gln | Ser<br>100 | Cys | Asp | Gln | Asp | Glu<br>105 | Asn | Gly | Asn | Arg | Thr<br>110 | Ser | Val |
| Asp | Leu | Arg<br>115 | Ile | Arg | Arg | Thr | Gln<br>120 | His | Ser | Val | Leu | Ser<br>125 | Arg | Lys | Phe |
| Val | Asp<br>130 | Val | Met | Thr | Glu | Tyr<br>135 | Asn | Glu | Ala | Gln | Ile<br>140 | Leu | Phe | Arg | Glu |
| Arg<br>145 | Ser | Lys | Gly | Arg | Ile<br>150 | Gln | Arg | Gln | Leu | Glu<br>155 | Ile | Thr | Gly | Arg | Thr<br>160 |
| Thr | Thr | Asp | Glu | Glu<br>165 | Leu | Glu | Glu | Met | Leu<br>170 | Glu | Ser | Gly | Lys | Pro<br>175 | Ser |

| | | | | | | | | | | | | | | |
|---|---|---|---|---|---|---|---|---|---|---|---|---|---|---|
|Ile|Phe|Ile|Ser|Asp|Ile|Ile|Ser|Asp|Ser|Gln|Ile|Thr|Arg|Gln|Ala|
| | | |180| | | | |185| | | |190| | |

| | | | | | | | | | | | | |
|---|---|---|---|---|---|---|---|---|---|---|---|---|
|Leu|Asn|Glu|Ile|Glu|Ser|Arg|His|Lys|Asp|Ile|Met|Lys|Leu|Glu|Thr|
| | |195| | | | |200| | | |205| | | |

| | | | | | | | | | | | | |
|---|---|---|---|---|---|---|---|---|---|---|---|---|
|Ser|Ile|Arg|Glu|Leu|His|Glu|Met|Phe|Met|Asp|Met|Ala|Met|Phe|Val|
| |210| | | | |215| | | |220| | | | |

Glu Thr Gln Gly Glu Met Val Asn Asn Ile Glu Arg Asn Val Val Asn
225                 230                 235                     240

Ser Val Asp Tyr Val Glu His Ala Lys Glu Thr Lys Lys Ala Ile
                245             250                 255

Lys Tyr Gln Ser Lys Ala Arg Arg Lys Lys Trp Ile Ile Ala Ala Val
            260                 265                 270

Val Val Ala Val Ile Ala Val Leu Ala Leu Ile Ile Gly Leu Thr Val
        275                 280                 285

Gly Lys
290

(2) INFORMATION FOR SEQ ID NO:7:

(i) SEQUENCE CHARACTERISTICS:
        (A) LENGTH: 1054 base pairs
        (B) TYPE: nucleic acid
        (C) STRANDEDNESS: double
        (D) TOPOLOGY: unknown (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Rat syntaxin 3 (GenBank L20820)

(ix) FEATURE:
        (A) NAME/KEY: CDS
        (B) LOCATION: 78..947

(xi) SEQUENCE DESCRIPTION: SEQ ID NO:7:

```
CCCGCAGTTG CTCCAGGCCG CTCACTTGGG ACGCGCTTAC CTGAGACAAG GCGCCTGCCA          60

CCCTCACCTG GACCAGG ATG AAG GAC CGA CTG GAG CAG CTG AAG GCC AAG           110
                Met Lys Asp Arg Leu Glu Gln Leu Lys Ala Lys
                 1               5                  10

CAG CTG ACG CAG GAT GAT GAC ACG GAC GAG GTT GAG ATT GCT ATT GAT           158
Gln Leu Thr Gln Asp Asp Asp Thr Asp Glu Val Glu Ile Ala Ile Asp
             15                  20                  25

AAT ACA GCG TTC ATG GAT GAG TTC TTT TCT GAG ATT GAG GAA ACG AGG           206
Asn Thr Ala Phe Met Asp Glu Phe Phe Ser Glu Ile Glu Glu Thr Arg
         30                  35                  40

CTC AAC ATC GAC AAG ATC TCA GAG CAT GTG GAG GAA GCT AAG AAA CTC           254
Leu Asn Ile Asp Lys Ile Ser Glu His Val Glu Glu Ala Lys Lys Leu
     45                  50                  55

TAC AGT ATC ATT CTC TCT GCA CCG ATT CCA GAG CCA AAA ACC AAA GAC           302
Tyr Ser Ile Ile Leu Ser Ala Pro Ile Pro Glu Pro Lys Thr Lys Asp
 60                  65                  70                  75

GAC CTT GAA CAG CTC ACA ACT GAG ATC AAG AAA AGG GCC AAC AAC GTC           350
Asp Leu Glu Gln Leu Thr Thr Glu Ile Lys Lys Arg Ala Asn Asn Val
                 80                  85                  90

CGG AAC AAA CTG AAG AGC ATG GAG AAG CAT ATT GAG GAA GAC GAG GTC           398
Arg Asn Lys Leu Lys Ser Met Glu Lys His Ile Glu Glu Asp Glu Val
             95                 100                 105

CGG TCA TCA GCA GAC CTT CGG ATA CGA AAG TCC CAG CAC TCC GTC CTC           446
Arg Ser Ser Ala Asp Leu Arg Ile Arg Lys Ser Gln His Ser Val Leu
```

|   |   |   |   |   |   |   |   |   |   |   |   |   |   |   |   |   |
|---|---|---|---|---|---|---|---|---|---|---|---|---|---|---|---|---|
|   |   |   | 110 |   |   |   |   | 115 |   |   |   |   | 120 |   |   |   |
| TCC | CGG | AAG | TTT | GTG | GAG | GTG | ATG | ACA | AAG | TAC | AAT | GAG | GCA | CAG | GTG | 494 |
| Ser | Arg | Lys | Phe | Val | Glu | Val | Met | Thr | Lys | Tyr | Asn | Glu | Ala | Gln | Val |   |
|   | 125 |   |   |   | 130 |   |   |   |   | 135 |   |   |   |   |   |   |
| GAC | TTC | CGT | GAA | CGC | AGC | AAA | GGG | CGC | ATC | CAA | CGG | CAG | CTT | GAA | ATT | 542 |
| Asp | Phe | Arg | Glu | Arg | Ser | Lys | Gly | Arg | Ile | Gln | Arg | Gln | Leu | Glu | Ile |   |
| 140 |   |   |   |   | 145 |   |   |   |   | 150 |   |   |   |   | 155 |   |
| ACT | GGC | AAG | AAA | ACA | ACA | GAT | GAG | GAG | CTG | GAA | GAA | ATG | TTG | GAG | AGT | 590 |
| Thr | Gly | Lys | Lys | Thr | Thr | Asp | Glu | Glu | Leu | Glu | Glu | Met | Leu | Glu | Ser |   |
|   |   |   |   | 160 |   |   |   |   | 165 |   |   |   |   | 170 |   |   |
| GGC | AAC | CCA | GCC | ATC | TTC | ACT | TCT | GGG | ATC | ATT | GAC | TCC | CAG | ATT | TCC | 638 |
| Gly | Asn | Pro | Ala | Ile | Phe | Thr | Ser | Gly | Ile | Ile | Asp | Ser | Gln | Ile | Ser |   |
|   |   |   | 175 |   |   |   |   | 180 |   |   |   |   | 185 |   |   |   |
| AAG | CAA | GCC | CTC | AGC | GAG | ATT | GAG | GGT | CGG | CAC | AAG | GAC | ATC | GTG | AGG | 686 |
| Lys | Gln | Ala | Leu | Ser | Glu | Ile | Glu | Gly | Arg | His | Lys | Asp | Ile | Val | Arg |   |
|   |   | 190 |   |   |   |   | 195 |   |   |   |   | 200 |   |   |   |   |
| CTG | GAG | AGC | AGC | ATC | AAG | GAG | CTC | CAT | GAC | ATG | TTT | ATG | GAC | ATC | GCC | 734 |
| Leu | Glu | Ser | Ser | Ile | Lys | Glu | Leu | His | Asp | Met | Phe | Met | Asp | Ile | Ala |   |
|   | 205 |   |   |   |   | 210 |   |   |   |   | 215 |   |   |   |   |   |
| ATG | CTG | GTG | GAG | AAT | CAG | GGT | GAG | ATG | TTA | GAT | AAC | ATA | GAG | TTG | AAT | 782 |
| Met | Leu | Val | Glu | Asn | Gln | Gly | Glu | Met | Leu | Asp | Asn | Ile | Glu | Leu | Asn |   |
| 220 |   |   |   |   | 225 |   |   |   |   | 230 |   |   |   |   | 235 |   |
| GTC | ATG | CAC | ACG | GTG | GAC | CAT | GTG | GAG | AAG | GCA | CGG | GAT | GAA | ACT | AAA | 830 |
| Val | Met | His | Thr | Val | Asp | His | Val | Glu | Lys | Ala | Arg | Asp | Glu | Thr | Lys |   |
|   |   |   | 240 |   |   |   |   | 245 |   |   |   |   | 250 |   |   |   |
| AGA | GCC | ATG | AAG | TAT | CAG | GGT | CAG | GCT | CGA | AAG | AAA | TTG | ATA | ATT | ATC | 878 |
| Arg | Ala | Met | Lys | Tyr | Gln | Gly | Gln | Ala | Arg | Lys | Lys | Leu | Ile | Ile | Ile |   |
|   |   |   | 255 |   |   |   |   | 260 |   |   |   |   | 265 |   |   |   |
| ATT | GTG | ATA | GTA | GTT | GTG | TTG | CTG | GGC | ATT | TTA | GCG | TTG | ATT | ATT | GGA | 926 |
| Ile | Val | Ile | Val | Val | Val | Leu | Leu | Gly | Ile | Leu | Ala | Leu | Ile | Ile | Gly |   |
|   |   | 270 |   |   |   |   | 275 |   |   |   |   | 280 |   |   |   |   |
| TTG | TCC | GTT | GGG | CTG | AAA | TAAGAGTGGC | CTAAGGGCT | GCTGCACTGA |   |   |   |   |   |   |   | 974 |
| Leu | Ser | Val | Gly | Leu | Lys |   |   |   |   |   |   |   |   |   |   |   |
| 285 |   |   |   |   | 290 |   |   |   |   |   |   |   |   |   |   |   |

AATCTTGGCC TGACCACTCT TGTCTCCAGA TGGGAACAAA GATTAAATGG CCTTCCTGAG    1034

AATGAGGGGT ACTGTTCTTT    1054

( 2 ) INFORMATION FOR SEQ ID NO:8:

( i ) SEQUENCE CHARACTERISTICS:
        ( A ) LENGTH: 289 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Met | Lys | Asp | Arg | Leu | Glu | Gln | Leu | Lys | Ala | Lys | Gln | Leu | Thr | Gln | Asp |
|---|---|---|---|---|---|---|---|---|---|---|---|---|---|---|---|
| 1 |   |   |   | 5 |   |   |   |   | 10 |   |   |   |   | 15 |   |
| Asp | Asp | Thr | Asp | Glu | Val | Glu | Ile | Ala | Ile | Asp | Asn | Thr | Ala | Phe | Met |
|   |   |   | 20 |   |   |   |   | 25 |   |   |   |   | 30 |   |   |
| Asp | Glu | Phe | Phe | Ser | Glu | Ile | Glu | Glu | Thr | Arg | Leu | Asn | Ile | Asp | Lys |
|   |   | 35 |   |   |   |   | 40 |   |   |   |   | 45 |   |   |   |
| Ile | Ser | Glu | His | Val | Glu | Glu | Ala | Lys | Lys | Leu | Tyr | Ser | Ile | Ile | Leu |
|   | 50 |   |   |   |   | 55 |   |   |   |   | 60 |   |   |   |   |
| Ser | Ala | Pro | Ile | Pro | Glu | Pro | Lys | Thr | Lys | Asp | Asp | Leu | Glu | Gln | Leu |
| 65 |   |   |   |   | 70 |   |   |   |   | 75 |   |   |   |   | 80 |
| Thr | Thr | Glu | Ile | Lys | Lys | Arg | Ala | Asn | Asn | Val | Arg | Asn | Lys | Leu | Lys |
|   |   |   |   | 85 |   |   |   |   | 90 |   |   |   |   | 95 |   |

```
Ser  Met  Glu  Lys  His  Ile  Glu  Glu  Asp  Glu  Val  Arg  Ser  Ser  Ala  Asp
               100                      105                      110

Leu  Arg  Ile  Arg  Lys  Ser  Gln  His  Ser  Val  Leu  Ser  Arg  Lys  Phe  Val
          115                      120                      125

Glu  Val  Met  Thr  Lys  Tyr  Asn  Glu  Ala  Gln  Val  Asp  Phe  Arg  Glu  Arg
     130                      135                      140

Ser  Lys  Gly  Arg  Ile  Gln  Arg  Gln  Leu  Glu  Ile  Thr  Gly  Lys  Lys  Thr
145                      150                      155                           160

Thr  Asp  Glu  Glu  Leu  Glu  Glu  Met  Leu  Glu  Ser  Gly  Asn  Pro  Ala  Ile
                    165                      170                      175

Phe  Thr  Ser  Gly  Ile  Ile  Asp  Ser  Gln  Ile  Ser  Lys  Gln  Ala  Leu  Ser
               180                      185                      190

Glu  Ile  Glu  Gly  Arg  His  Lys  Asp  Ile  Val  Arg  Leu  Glu  Ser  Ser  Ile
          195                      200                      205

Lys  Glu  Leu  His  Asp  Met  Phe  Met  Asp  Ile  Ala  Met  Leu  Val  Glu  Asn
     210                      215                      220

Gln  Gly  Glu  Met  Leu  Asp  Asn  Ile  Glu  Leu  Asn  Val  Met  His  Thr  Val
225                      230                      235                           240

Asp  His  Val  Glu  Lys  Ala  Arg  Asp  Glu  Thr  Lys  Arg  Ala  Met  Lys  Tyr
                    245                      250                      255

Gln  Gly  Gln  Ala  Arg  Lys  Lys  Leu  Ile  Ile  Ile  Val  Ile  Val  Val
               260                      265                      270

Val  Leu  Leu  Gly  Ile  Leu  Ala  Leu  Ile  Ile  Gly  Leu  Ser  Val  Gly  Leu
          275                      280                      285

Lys
```

( 2 ) INFORMATION FOR SEQ ID NO:9:

( i ) SEQUENCE CHARACTERISTICS:
        ( A ) LENGTH: 973 base pairs
        ( B ) TYPE: nucleic acid
        ( C ) STRANDEDNESS: double
        ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Rat syntaxin 4 (GenBank L20821)

( i x ) FEATURE:
        ( A ) NAME/KEY: CDS
        ( B ) LOCATION: 32..928

( x i ) SEQUENCE DESCRIPTION: SEQ ID NO:9:

```
TTTGGGCTCA GGTCCAGGCA CTCCGGCCAC C ATG CGC GAC AGG ACC CAT GAG        52
                                   Met Arg Asp Arg Thr His Glu
                                    1               5

TTG AGG CAG GGG GAT AAC ATC TCA GAC GAT GAA GAT GAG GTT CGA GTC      100
Leu Arg Gln Gly Asp Asn Ile Ser Asp Asp Glu Asp Glu Val Arg Val
         10              15                  20

GCG TTG GTG GTG CAC TCA GGT GCC GCC CGG CTG AGC AGC CCG GAC GAC      148
Ala Leu Val Val His Ser Gly Ala Ala Arg Leu Ser Ser Pro Asp Asp
     25                  30                  35

GAG TTC TTC CAG AAG GTG CAG ACA ATT CGG CAG ACT ATG GCC AAA CTG      196
Glu Phe Phe Gln Lys Val Gln Thr Ile Arg Gln Thr Met Ala Lys Leu
 40              45                  50                      55

GAG AGT AAA GTC CGG GAG TTG GAG AAA CAG CAG GTC ACC ATT CTG GCC      244
Glu Ser Lys Val Arg Glu Leu Glu Lys Gln Gln Val Thr Ile Leu Ala
```

| | | | | | | | | 60 | | | | | 65 | | | | 70 | | | |
|---|---|---|---|---|---|---|---|---|---|---|---|---|---|---|---|---|---|---|---|---|
| ACG | CCT | CTT | CCC | GAG | GAG | AGC | ATG | AAG | CAG | GGC | CTG | CAG | AAC | CTG | CGA | | | | | 292 |
| Thr | Pro | Leu | Pro | Glu | Glu | Ser | Met | Lys | Gln | Gly | Leu | Gln | Asn | Leu | Arg | | | | | |
| | | | 75 | | | | | 80 | | | | | 85 | | | | | | | |
| GAG | GAG | ATC | AAA | CAG | CTG | GGG | AGA | GAA | GTC | CGG | GCA | CAG | CTA | AAA | GCC | | | | | 340 |
| Glu | Glu | Ile | Lys | Gln | Leu | Gly | Arg | Glu | Val | Arg | Ala | Gln | Leu | Lys | Ala | | | | | |
| | | | 90 | | | | | 95 | | | | | 100 | | | | | | | |
| ATA | GAG | CCC | CAG | AAG | GAA | GAA | GCT | GAT | GAG | AAT | TAT | AAT | TCA | GTC | AAC | | | | | 388 |
| Ile | Glu | Pro | Gln | Lys | Glu | Glu | Ala | Asp | Glu | Asn | Tyr | Asn | Ser | Val | Asn | | | | | |
| | | 105 | | | | | 110 | | | | | 115 | | | | | | | | |
| ACA | AGA | ATG | AAG | AAA | ACC | CAG | CAT | GGG | GTC | CTG | TCC | CAG | CAG | TTT | GTG | | | | | 436 |
| Thr | Arg | Met | Lys | Lys | Thr | Gln | His | Gly | Val | Leu | Ser | Gln | Gln | Phe | Val | | | | | |
| 120 | | | | | 125 | | | | | 130 | | | | | 135 | | | | | |
| GAG | CTC | ATC | AAC | AAG | TGT | AAC | TCA | ATG | CAG | TCC | GAG | TAC | CGA | GAG | AAG | | | | | 484 |
| Glu | Leu | Ile | Asn | Lys | Cys | Asn | Ser | Met | Gln | Ser | Glu | Tyr | Arg | Glu | Lys | | | | | |
| | | | | 140 | | | | | 145 | | | | | 150 | | | | | | |
| AAC | GTG | GAG | CGC | ATT | CGG | CGG | CAG | CTG | AAG | ATC | ACC | AAT | GCT | GGA | ATG | | | | | 532 |
| Asn | Val | Glu | Arg | Ile | Arg | Arg | Gln | Leu | Lys | Ile | Thr | Asn | Ala | Gly | Met | | | | | |
| | | | 155 | | | | | 160 | | | | | 165 | | | | | | | |
| GTG | TCT | GAC | GAG | GAA | CTG | GAG | CAG | ATG | CTG | GAC | AGT | GGG | CAG | AGT | GAG | | | | | 580 |
| Val | Ser | Asp | Glu | Glu | Leu | Glu | Gln | Met | Leu | Asp | Ser | Gly | Gln | Ser | Glu | | | | | |
| | | 170 | | | | | 175 | | | | | 180 | | | | | | | | |
| GTG | TTT | GTG | TCT | AAT | ATA | CTG | AAG | GAC | ACA | CAG | GTG | ACC | CGG | CAG | GCC | | | | | 628 |
| Val | Phe | Val | Ser | Asn | Ile | Leu | Lys | Asp | Thr | Gln | Val | Thr | Arg | Gln | Ala | | | | | |
| | 185 | | | | | 190 | | | | | 195 | | | | | | | | | |
| CTG | AAT | GAG | ATC | TCT | GCG | CGA | CAC | AGT | GAG | ATC | CAG | CAG | TTG | GAG | CGC | | | | | 676 |
| Leu | Asn | Glu | Ile | Ser | Ala | Arg | His | Ser | Glu | Ile | Gln | Gln | Leu | Glu | Arg | | | | | |
| 200 | | | | 205 | | | | | 210 | | | | | 215 | | | | | | |
| ACG | ATC | CGT | GAA | CTC | CAT | GAG | ATC | TTC | ACT | TTT | CTA | GCT | ACC | GAG | GTG | | | | | 724 |
| Thr | Ile | Arg | Glu | Leu | His | Glu | Ile | Phe | Thr | Phe | Leu | Ala | Thr | Glu | Val | | | | | |
| | | | | 220 | | | | | 225 | | | | | 230 | | | | | | |
| GAG | ATG | CAG | GGA | GAG | ATG | ATC | AAT | CGT | ATC | GAA | AAG | AAC | ATT | CTG | AGC | | | | | 772 |
| Glu | Met | Gln | Gly | Glu | Met | Ile | Asn | Arg | Ile | Glu | Lys | Asn | Ile | Leu | Ser | | | | | |
| | | | 235 | | | | | 240 | | | | | 245 | | | | | | | |
| TCA | GCA | GAC | TAT | GTG | GAA | CGT | GGG | CAA | GAA | CAT | GTC | AAG | ATA | GCG | CTA | | | | | 820 |
| Ser | Ala | Asp | Tyr | Val | Glu | Arg | Gly | Gln | Glu | His | Val | Lys | Ile | Ala | Leu | | | | | |
| | | 250 | | | | | 255 | | | | | 260 | | | | | | | | |
| GAG | AAT | CAG | AAG | AAG | GCG | AGG | AAG | AAA | AAG | GTC | ATG | ATT | GCC | ATC | TGT | | | | | 868 |
| Glu | Asn | Gln | Lys | Lys | Ala | Arg | Lys | Lys | Lys | Val | Met | Ile | Ala | Ile | Cys | | | | | |
| | 265 | | | | | 270 | | | | | 275 | | | | | | | | | |
| GTT | TCT | GTC | ACT | GTT | CTC | ATC | TTG | GCT | GTC | ATC | ATT | GGC | ATC | ACC | ATA | | | | | 916 |
| Val | Ser | Val | Thr | Val | Leu | Ile | Leu | Ala | Val | Ile | Ile | Gly | Ile | Thr | Ile | | | | | |
| 280 | | | | | 285 | | | | | 290 | | | | | 295 | | | | | |
| ACC | GTT | GGA | TAATGTCACA | TGTTCTTGGC | ACTGGGAGAA | ACAGAGACCC | AGCATTTG | | | | | | | | | | | | | 973 |
| Thr | Val | Gly | | | | | | | | | | | | | | | | | | |

( 2 ) INFORMATION FOR SEQ ID NO:10:

( i ) SEQUENCE CHARACTERISTICS:
        ( A ) LENGTH: 298 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | Arg | Asp | Arg | Thr | His | Glu | Leu | Arg | Gln | Gly | Asp | Asn | Ile | Ser | Asp |
|---|---|---|---|---|---|---|---|---|---|---|---|---|---|---|---|
| 1 | | | | 5 | | | | | 10 | | | | | 15 | |
| Asp | Glu | Asp | Glu | Val | Arg | Val | Ala | Leu | Val | Val | His | Ser | Gly | Ala | Ala |
| | | | 20 | | | | | 25 | | | | | 30 | | |
| Arg | Leu | Ser | Ser | Pro | Asp | Asp | Glu | Phe | Phe | Gln | Lys | Val | Gln | Thr | Ile |

|   |   |   |   |   | 35 |   |   |   |   | 40 |   |   |   |   | 45 |   |   |   |
|---|---|---|---|---|---|---|---|---|---|---|---|---|---|---|---|---|---|---|

Arg Gln Thr Met Ala Lys Leu Glu Ser Lys Val Arg Glu Leu Glu Lys
    50              55                  60

Gln Gln Val Thr Ile Leu Ala Thr Pro Leu Pro Glu Glu Ser Met Lys
65              70                  75                      80

Gln Gly Leu Gln Asn Leu Arg Glu Glu Ile Lys Gln Leu Gly Arg Glu
                85                  90                  95

Val Arg Ala Gln Leu Lys Ala Ile Glu Pro Gln Lys Glu Glu Ala Asp
            100                 105                 110

Glu Asn Tyr Asn Ser Val Asn Thr Arg Met Lys Lys Thr Gln His Gly
            115                 120                 125

Val Leu Ser Gln Gln Phe Val Glu Leu Ile Asn Lys Cys Asn Ser Met
    130                 135                 140

Gln Ser Glu Tyr Arg Glu Lys Asn Val Glu Arg Ile Arg Arg Gln Leu
145                 150                 155                 160

Lys Ile Thr Asn Ala Gly Met Val Ser Asp Glu Glu Leu Glu Gln Met
                165                 170                 175

Leu Asp Ser Gly Gln Ser Glu Val Phe Val Ser Asn Ile Leu Lys Asp
                180                 185                 190

Thr Gln Val Thr Arg Gln Ala Leu Asn Glu Ile Ser Ala Arg His Ser
    195                 200                 205

Glu Ile Gln Gln Leu Glu Arg Thr Ile Arg Glu Leu His Glu Ile Phe
    210                 215                 220

Thr Phe Leu Ala Thr Glu Val Glu Met Gln Gly Glu Met Ile Asn Arg
225                 230                 235                 240

Ile Glu Lys Asn Ile Leu Ser Ser Ala Asp Tyr Val Glu Arg Gly Gln
                245                 250                 255

Glu His Val Lys Ile Ala Leu Glu Asn Gln Lys Lys Ala Arg Lys Lys
            260                 265                 270

Lys Val Met Ile Ala Ile Cys Val Ser Val Thr Val Leu Ile Leu Ala
        275                 280                 285

Val Ile Ile Gly Ile Thr Ile Thr Val Gly
    290                 295

( 2 ) INFORMATION FOR SEQ ID NO:11:

( i ) SEQUENCE CHARACTERISTICS:
        ( A ) LENGTH: 1608 base pairs
        ( B ) TYPE: nucleic acid
        ( C ) STRANDEDNESS: double
        ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Rat syntaxin 5 (GenBank L20822)

( i x ) FEATURE:
        ( A ) NAME/KEY: CDS
        ( B ) LOCATION: 130..1035

( x i ) SEQUENCE DESCRIPTION: SEQ ID NO:11:

ACGGATCAGG GTGTCTACCT GGGTCTCTCA AAGACACAGG TTCTGTCCCC TGCAACTGCT    60

ATCAATAGCA GCAGTGACAT CGCTCCTTTG CCCACCCCGG TGGCCCTGGT CCCCTCCCCT  120

CCCGACACT ATG TCC TGC CGG GAT CGG ACC CAG GAG TTC CTG TCT GCC    168
        Met Ser Cys Arg Asp Arg Thr Gln Glu Phe Leu Ser Ala

```
        1                     5                           10
TGC  AAG  TCG  CTG  CAG  AGC  CGT  CAG  AAT  GGA  ATC  CAA  ACA  AAT  AAA  CCA      216
Cys  Lys  Ser  Leu  Gln  Ser  Arg  Gln  Asn  Gly  Ile  Gln  Thr  Asn  Lys  Pro
     15                  20                       25

GCT  CTG  CAC  GCT  ACC  CGG  CAG  TGC  AGC  GAG  TTT  ACC  CTC  ATG  GCC  AGG      264
Ala  Leu  His  Ala  Thr  Arg  Gln  Cys  Ser  Glu  Phe  Thr  Leu  Met  Ala  Arg
30                       35                       40                         45

CGC  ATT  GGG  AAA  GAT  CTC  AGC  AAT  ACA  TTT  GCC  AAG  CTG  GAG  AAG  CTA      312
Arg  Ile  Gly  Lys  Asp  Leu  Ser  Asn  Thr  Phe  Ala  Lys  Leu  Glu  Lys  Leu
                    50                       55                       60

ACA  ATC  CTG  GCA  AAG  CGC  AAG  TCC  CTC  TTT  GAT  GAT  AAA  GCA  GTA  GAA      360
Thr  Ile  Leu  Ala  Lys  Arg  Lys  Ser  Leu  Phe  Asp  Asp  Lys  Ala  Val  Glu
               65                       70                       75

ATT  GAG  GAA  CTA  ACA  TAC  ATC  ATC  AAA  CAG  GAC  ATC  AAT  AGC  CTC  AAC      408
Ile  Glu  Glu  Leu  Thr  Tyr  Ile  Ile  Lys  Gln  Asp  Ile  Asn  Ser  Leu  Asn
          80                       85                       90

AAA  CAA  ATT  GCT  CAG  CTT  CAA  GAT  TTT  GTG  AGG  GCC  AAG  GGC  AGC  CAG      456
Lys  Gln  Ile  Ala  Gln  Leu  Gln  Asp  Phe  Val  Arg  Ala  Lys  Gly  Ser  Gln
     95                       100                      105

AGT  GGC  CGG  CAT  CTG  CAG  ACC  CAT  TCC  AAC  ACC  ATT  GTA  GTT  TCA  TTG      504
Ser  Gly  Arg  His  Leu  Gln  Thr  His  Ser  Asn  Thr  Ile  Val  Val  Ser  Leu
110                      115                      120                      125

CAG  TCA  AAA  CTG  GCT  TCC  ATG  TCC  AAT  GAC  TTC  AAG  TCT  GTT  TTG  GAA      552
Gln  Ser  Lys  Leu  Ala  Ser  Met  Ser  Asn  Asp  Phe  Lys  Ser  Val  Leu  Glu
                    130                      135                      140

GTG  AGG  ACT  GAA  AAT  CTG  AAA  CAG  CAG  AGG  AAC  CGT  CGG  GAA  CAG  TTC      600
Val  Arg  Thr  Glu  Asn  Leu  Lys  Gln  Gln  Arg  Asn  Arg  Arg  Glu  Gln  Phe
               145                      150                      155

TCC  AGG  GCG  CCA  GTG  TCG  GCA  CTG  CCT  CTG  GCC  CCC  AAC  AAC  CTT  GGA      648
Ser  Arg  Ala  Pro  Val  Ser  Ala  Leu  Pro  Leu  Ala  Pro  Asn  Asn  Leu  Gly
          160                      165                      170

GGT  GGT  CCC  ATA  GTT  CTG  GGA  GGA  GAG  TCC  CGA  GCC  TCC  AGG  GAC  GTG      696
Gly  Gly  Pro  Ile  Val  Leu  Gly  Gly  Glu  Ser  Arg  Ala  Ser  Arg  Asp  Val
175                      180                      185

GCC  ATC  GAC  ATG  ATG  GAC  CCT  AGA  ACA  AGC  CAG  CAG  CTT  CAG  CTC  ATT      744
Ala  Ile  Asp  Met  Met  Asp  Pro  Arg  Thr  Ser  Gln  Gln  Leu  Gln  Leu  Ile
190                      195                      200                      205

GAT  GAG  CAG  GAT  TCC  TAC  ATC  CAG  AGT  CGG  GCA  GAC  ACC  ATG  CAG  AAC      792
Asp  Glu  Gln  Asp  Ser  Tyr  Ile  Gln  Ser  Arg  Ala  Asp  Thr  Met  Gln  Asn
                    210                      215                      220

ATT  GAG  TCT  ACA  ATT  GTT  GAG  CTG  GGC  TCC  ATT  TTT  CAA  CAA  TTG  GCA      840
Ile  Glu  Ser  Thr  Ile  Val  Glu  Leu  Gly  Ser  Ile  Phe  Gln  Gln  Leu  Ala
               225                      230                      235

CAC  ATG  GTT  AAA  GAA  CAG  GAG  GAA  ACA  ATT  CAG  AGG  ATT  GAC  GAG  AAT      888
His  Met  Val  Lys  Glu  Gln  Glu  Glu  Thr  Ile  Gln  Arg  Ile  Asp  Glu  Asn
          240                      245                      250

GTG  CTT  GGA  GCC  CAG  CTG  GAT  GTT  GAG  GCC  GCC  CAT  TCA  GAG  ATC  CTC      936
Val  Leu  Gly  Ala  Gln  Leu  Asp  Val  Glu  Ala  Ala  His  Ser  Glu  Ile  Leu
255                      260                      265

AAG  TAC  TTC  CAG  TCA  GTC  ACC  TCC  AAT  CGG  TGG  CTC  ATG  GTC  AAA  ATC      984
Lys  Tyr  Phe  Gln  Ser  Val  Thr  Ser  Asn  Arg  Trp  Leu  Met  Val  Lys  Ile
270                      275                      280                      285

TTC  CTC  ATC  CTC  ATT  GTC  TTC  TTC  ATC  ATC  TTT  GTG  GTC  TTC  CTT  GCC     1032
Phe  Leu  Ile  Leu  Ile  Val  Phe  Phe  Ile  Ile  Phe  Val  Val  Phe  Leu  Ala
                    290                      295                      300

TGAACCCTCC  TCCCTCATTC  TGAGCCACTC  CATGGAGGGC  CTGGAACCCT  TCTGGAAGGA                1092

CAGGTGGCCA  CTATTGCCAC  TGAGCCTGTG  CAGGGTAGTT  GGGAGAAAGG  CCATTTCCTT                1152

GGAACTGCTA  AGAATGGCCA  GTGTCCCTGA  TTCCCCACCC  TTGTCTCTGG  CCACTCTGTC                1212
```

| | | | | |
|---|---|---|---|---|
| CTACCCTCAG | GCCCATGAAA | CACACTGGTT | CTGGATTTGG | CCTCTGCTGT GAAGTGGCAG | 1272 |
| GGAACAGAAG | CCAGCTAGGG | CCAGTGGGGA | GGTTGTCTCT | ACCATGAGAT TTTTATAAAC | 1332 |
| CCAGACCAGC | CTCCCCTAAA | GGTAACTGGC | AGCAAGAGGA | AACAATGCCC TCCTTGCCTT | 1392 |
| CTGGAGAGTG | AGGTGAGGAA | GTAAAACTAT | CCCAGGGACC | AACTTAATCA TCTGGGTCAT | 1452 |
| CTAGAACTTG | ACTGCCACCT | TCTCCTCACC | ATGTGAGGTG | GGGGGGCTCT GAGCCCTACA | 1512 |
| GTTGCACAAA | CCTGACTTTG | GCTACTGGTG | ACTCTCAATC | TGCCAAACAT GCTGCAGCCT | 1572 |
| GTTTCCTCCC | AATTACAGCA | AGACTGTCAG | CCTTCA | | 1608 |

( 2 ) INFORMATION FOR SEQ ID NO:12:

( i ) SEQUENCE CHARACTERISTICS:
        ( A ) LENGTH: 301 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Ser Cys Arg Asp Arg Thr Gln Glu Phe Leu Ser Ala Cys Lys Ser
 1               5                  10                  15

Leu Gln Ser Arg Gln Asn Gly Ile Gln Thr Asn Lys Pro Ala Leu His
            20                  25                  30

Ala Thr Arg Gln Cys Ser Glu Phe Thr Leu Met Ala Arg Arg Ile Gly
        35                  40                  45

Lys Asp Leu Ser Asn Thr Phe Ala Lys Leu Glu Lys Leu Thr Ile Leu
    50                  55                  60

Ala Lys Arg Lys Ser Leu Phe Asp Asp Lys Ala Val Glu Ile Glu Glu
65                  70                  75                  80

Leu Thr Tyr Ile Ile Lys Gln Asp Ile Asn Ser Leu Asn Lys Gln Ile
                85                  90                  95

Ala Gln Leu Gln Asp Phe Val Arg Ala Lys Gly Ser Gln Ser Gly Arg
            100                 105                 110

His Leu Gln Thr His Ser Asn Thr Ile Val Val Ser Leu Gln Ser Lys
        115                 120                 125

Leu Ala Ser Met Ser Asn Asp Phe Lys Ser Val Leu Glu Val Arg Thr
    130                 135                 140

Glu Asn Leu Lys Gln Gln Arg Asn Arg Arg Glu Gln Phe Ser Arg Ala
145                 150                 155                 160

Pro Val Ser Ala Leu Pro Leu Ala Pro Asn Asn Leu Gly Gly Gly Pro
                165                 170                 175

Ile Val Leu Gly Gly Glu Ser Arg Ala Ser Arg Asp Val Ala Ile Asp
            180                 185                 190

Met Met Asp Pro Arg Thr Ser Gln Gln Leu Gln Leu Ile Asp Glu Gln
        195                 200                 205

Asp Ser Tyr Ile Gln Ser Arg Ala Asp Thr Met Gln Asn Ile Glu Ser
    210                 215                 220

Thr Ile Val Glu Leu Gly Ser Ile Phe Gln Gln Leu Ala His Met Val
225                 230                 235                 240

Lys Glu Gln Glu Glu Thr Ile Gln Arg Ile Asp Glu Asn Val Leu Gly
                245                 250                 255

Ala Gln Leu Asp Val Glu Ala Ala His Ser Glu Ile Leu Lys Tyr Phe
            260                 265                 270

Gln Ser Val Thr Ser Asn Arg Trp Leu Met Val Lys Ile Phe Leu Ile
        275                 280                 285
```

```
Leu  Ile  Val  Phe  Phe  Ile  Ile  Phe  Val  Val  Phe  Leu  Ala
     290                 295                      300
```

( 2 ) INFORMATION FOR SEQ ID NO:13:

( i ) SEQUENCE CHARACTERISTICS:
        ( A ) LENGTH: 1482 base pairs
        ( B ) TYPE: nucleic acid
        ( C ) STRANDEDNESS: double
        ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Rat VAMP-1 (GenBank M24104)

( i x ) FEATURE:
        ( A ) NAME/KEY: CDS
        ( B ) LOCATION: 98..454

( x i ) SEQUENCE DESCRIPTION: SEQ ID NO:13:

```
GAATTCGGGT  TCCGTCTACT  TCAGCCGCAG  CGTCTCCCTG  CCTGTCTCAT  TGCATTCTCC         60

AGAGAGGGGA  CGGACCTCCA  CTTCCTCTTT  CAGAAAA ATG TCT GCT CCA GCT CAG           115
                                            Met Ser Ala Pro Ala Gln
                                              1               5

CCA CCT GCT GAA GGG ACA GAA GGG GCT GCC CCA GGT GGG GGT CCT CCT             163
Pro Pro Ala Glu Gly Thr Glu Gly Ala Ala Pro Gly Gly Gly Pro Pro
            10                  15                  20

GGT CCT CCT CCC AAT ACG ACC AGT AAC AGA CGA TTA CAG CAA ACC CAG             211
Gly Pro Pro Pro Asn Thr Thr Ser Asn Arg Arg Leu Gln Gln Thr Gln
        25                  30                  35

GCA CAA GTG GAG GAG GTG GTG GAC ATC ATT CGC GTG AAT GTG GAC AAG             259
Ala Gln Val Glu Glu Val Val Asp Ile Ile Arg Val Asn Val Asp Lys
    40                  45                  50

GTC TTG GAG AGG GAC CAG AAG TTG TCA GAG TTG GAT GAC CGA GCT GAC             307
Val Leu Glu Arg Asp Gln Lys Leu Ser Glu Leu Asp Asp Arg Ala Asp
55                  60                  65                  70

GCC TTG CAG GCA GGA GCG TCA GTG TTT GAG AGC AGT GCT GCC AAG CTA             355
Ala Leu Gln Ala Gly Ala Ser Val Phe Glu Ser Ser Ala Ala Lys Leu
                75                  80                  85

AAA AGG AAG TAT TGG TGG AAA AAC TGC AAG ATG ATG ATC ATG CTG GGA             403
Lys Arg Lys Tyr Trp Trp Lys Asn Cys Lys Met Met Ile Met Leu Gly
            90                  95                 100

GCT ATC TGT GCC ATC ATC GTG GTA GTA ATT GTA ATC TAC ATT TTT ACT             451
Ala Ile Cys Ala Ile Ile Val Val Val Ile Val Ile Tyr Ile Phe Thr
        105                 110                 115

TGAGAATGTG  CCATCCCTTC  CCTGTTCTCC  ATTGCCATCC  AAGCTCATGT  TTCCCCTCTG       511

TTTGCTCTCT  CAACAAAGTC  CTCCATCTTC  CGTTCTCCAT  CCTGGCCCAG  GCTTCTCTGT       571

GATCCGACCT  TCCCTTTTTG  TGCATTCATT  CGCACTCTTC  CTCAAAACTA  GAAATGCTGC       631

TCGTGGCACA  GTCCTGAAAG  TCACTGCCCG  AAGAGAACAC  CCAGCACCTC  CTCTTTACCC       691

ATTTATCATG  TGCCCTGGAG  CTTAAAAGAG  TTGTGGCCAA  TGGCAGAGGT  GAAGTGTCTG       751

AGAAGTTAGC  ATGGCTGAGG  GGAAGAGAAA  GGCATTTGTG  TCCAAGAAAG  GCTGGCCTTT       811

GGCAGGAGGG  AAGCAAGAAT  AGTTGGGAAG  TAGTAGCTTG  CTGCCAGTGT  ATATGTATAT       871

GTATATGTAT  ATGTATATGT  ATATGTATAT  GTATATGTAT  ATATTAGTTG  GGAACTATGA       931

CCTGCTGTCC  TCATTTGGAA  CTTTCCTCCC  ATACCAGGCC  TGTCTTGGGT  CCCAGAGGTC       991

TGTTTAAAGA  CCAACTTCAA  ATCCCTTTTA  GAAAAACATC  AAACTTGCAT  TTTGTAGCTA      1051
```

```
CTGTTATCTG  TCAGTACAAG  ATTTTCTGTG  TCTTTGGGGG  AACTTTACAA  CTTTTCGCTT      1111
TGTCTCTATA  GCCCCAGGAG  AGAAGTACTT  TCTGATTTTA  AAAACAGCAG  GACACTCTTA      1171
CCTTCTTCTA  GAAGGCGTCC  CACATGCTTC  TGACTAGAAG  GAGCTACCAC  CTCTTCATGT      1231
CATCTGAAGC  ATTTGATGTT  GTTCATGAAG  GCACCAAATA  ATTTCAGGGA  ATGAGGGGCT      1291
TTGAGGATAA  CAGGCTCTCA  GGAACACGCT  CCATGCCATC  CCACTCTCCA  ATGAAAGCCC      1351
TGTACCTCCC  TTGTTGATTA  AGAGAAATGA  GAGTTATATG  GTGAGACTCC  CAGGGTCCCA      1411
CAGAACACTT  CCCCCTGCAC  TACCCACTTA  CTGTGTGTAA  GACAAGGATG  AGGCAGGAGG      1471
GCCCCGAATT  C                                                                1482
```

( 2 ) INFORMATION FOR SEQ ID NO:14:

( i ) SEQUENCE CHARACTERISTICS:
        ( A ) LENGTH: 118 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Ser Ala Pro Ala Gln Pro Pro Ala Glu Gly Thr Glu Gly Ala Ala
 1               5                  10                  15

Pro Gly Gly Gly Pro Pro Gly Pro Pro Asn Thr Thr Ser Asn Arg
            20                  25                  30

Arg Leu Gln Gln Thr Gln Ala Gln Val Glu Glu Val Val Asp Ile Ile
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Val Phe Glu
 65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
                100                 105                 110

Val Ile Tyr Ile Phe Thr
            115
```

( 2 ) INFORMATION FOR SEQ ID NO:15:

( i ) SEQUENCE CHARACTERISTICS:
        ( A ) LENGTH: 2071 base pairs
        ( B ) TYPE: nucleic acid
        ( C ) STRANDEDNESS: double
        ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Rat VAMP-2 (GenBank M24105)

( i x ) FEATURE:
        ( A ) NAME/KEY: CDS
        ( B ) LOCATION: 21..371

( x i ) SEQUENCE DESCRIPTION: SEQ ID NO:15:

```
GAATTCGGGC  TACCCCCGCC ATG TCG GCT ACC GCT GCC ACC GTC CCG CCT              50
                       Met Ser Ala Thr Ala Ala Thr Val Pro Pro
                        1               5                  10
```

| | | |
|---|---|---|
| GCC GCC CCG GCC GGC GAG GGT GGC CCC CCT GCA CCT CCT CCA AAT CTT<br>Ala Ala Pro Ala Gly Glu Gly Gly Pro Pro Ala Pro Pro Pro Asn Leu<br>15           20           25 | | 98 |
| ACC AGT AAC AGG AGA CTG CAG CAG ACC CAG GCC CAG GTG GAT GAG GTG<br>Thr Ser Asn Arg Arg Leu Gln Gln Thr Gln Ala Gln Val Asp Glu Val<br>30           35           40 | | 146 |
| GTG GAC ATC ATG AGG GTG AAT GTG GAC AAG GTC CTG GAG CGA GAC CAG<br>Val Asp Ile Met Arg Val Asn Val Asp Lys Val Leu Glu Arg Asp Gln<br>45           50           55 | | 194 |
| AAG CTA TCG GAA CTG GAT GAT CGC GCA GAT GCC CTC CAG GCA GGG GCC<br>Lys Leu Ser Glu Leu Asp Asp Arg Ala Asp Ala Leu Gln Ala Gly Ala<br>60           65           70 | | 242 |
| TCC CAG TTT GAA ACA AGT GCA GCC AAG CTC AAG CGC AAA TAC TGG TGG<br>Ser Gln Phe Glu Thr Ser Ala Ala Lys Leu Lys Arg Lys Tyr Trp Trp<br>75           80           85           90 | | 290 |
| AAA AAC CTC AAG ATG ATG ATC ATC TTG GGA GTG ATT TGC GCC ATC ATC<br>Lys Asn Leu Lys Met Met Ile Ile Leu Gly Val Ile Cys Ala Ile Ile<br>95           100           105 | | 338 |
| CTC ATC ATC ATC ATC GTT TAC TTC AGC ACT TAAGTCCCTG AGGAGTCTGC<br>Leu Ile Ile Ile Ile Val Tyr Phe Ser Thr<br>110           115 | | 388 |
| CCTGCCTAAG AAGGGCCTCT CCCCCACCCT CAGCCCGTCC TCCACCTCTC AGCCATATCT | | 448 |
| TTCAGCCCCC TCCCTTGGAT CCGTGTGTGT GTGTGTCCGT GTGTGCCC CCTGTAAATA | | 508 |
| GCCAGCTGTT ATTTATACAT ATATAATATT ATATATATTT GGTCTGTTTG TAGTTTTATT | | 568 |
| ACTAGAAGAT TTTTTCCGGT TGTCCTTAAC ACCCCTTCCT GAGGTTCCA TCACCTCTCT | | 628 |
| CTCTCACCCT CTGCCCCCTT TCCTCTTTCC TGTTCAGCCC CAAGTCCCTT CATTTGCATC | | 688 |
| TGCTATGCAA TAGCCCCTCT CCTCCTTCCC TTGGATTTAA CCAATCCTTC CCTATCTTC | | 748 |
| CCTGTACAAT TCCAGACCCT CCCCAAACAG AGCAAACCCC ACAGAAACAA ACAAAACACC | | 808 |
| CCACCTGTCT AGGCTTCCAT AGGTTGCATC TTTGTATCCC TTGGGAGCCT CTAAGACTGG | | 868 |
| TCCTACTTGG TCCTAAGAAT CCCAAGGATT TCTGGGAGCT TCCAACATGT TGATTAGCAT | | 928 |
| ATCATTTGCA TACACTGTCT TTTTTTTCCC TCGGTTTCTT CCTTTCTGTT CCATTACTCT | | 988 |
| TCACTCTTCT GTGTTTTTTT TTTTTCTTT CTTTCTTTTC GGAAGAGTTA GTTCCATTG | | 1048 |
| GTCCTCTTAT CACACTTTTA TTTGCACGAC ATTATCTGCA GGTGGTGGGG AGCCTGGGCT | | 1108 |
| TTTGGGGAAC TAGGACCCCA AAGTTGCCTC CTCCCAGCCC CTCTAGTCTA GTTTGCTTCC | | 1168 |
| CTTACCCCAT TTCCACACCT CTTGTACCCT CCTCTCCCTC CCCAGCTGG TGTGTAAGTG | | 1228 |
| TCTTGGAGTT CAGTGTGTTA TGATGGGACC AATAATTCTG CCACTTGGGG TCTCTCCCTA | | 1288 |
| CATTCCTGCT CCCCAGTTTT CGTGTGGGGC ATTCAGCTGA CATTTCCCGG GGGTCTCCCT | | 1348 |
| CCCTCCCATC TGCCTGATCT GCTGCCTCCT CCCACCAGGA GAACTGGAGG CTGACCACAA | | 1408 |
| TCTGGTTCTT TGAGGAGGGG TGGCTCTAGT GTGTGTGGGG GTCATCACTG CCTTGGGGAG | | 1468 |
| GAGTAGGACA AAACAGAACC CCCCTAATT CCTGCCTGAA ATCTCTGGCC TCATCCTTGC | | 1528 |
| TAGAGGTTGG ACTGAAAACT TTCCTCCCCA ATCCTGGGGG GTATTACCCC CCATCACTGC | | 1588 |
| CCAGCTCCTC TGACTGCCCC CCTGTATTCA GGGTGGGGGT ACTAGTCACT GCCAATATGT | | 1648 |
| GTATGGGACT TGCTGGAGGA TGGGGATCCT TGTCCTTCTC TAGGGCTGCT GAGCCCTGAG | | 1708 |
| AGAGAGAGAG AGAGAGAGAG AGAGAGAGAG AGAGAGAGAG AGAGAAGCAA GCTATTTCCC | | 1768 |
| TGTTGGGTAC AATGATAGAG AAAGGATCTA ATCGGGAAAA ATGGCACAGT TTAGGGGTC | | 1828 |
| TGAGGGTACA GCCCCTTAAC CTGCCTCTTG GGGGGGGGTG TTCCCCAAAC TCTTCCCCCA | | 1888 |
| CACACACCAG GTTTTCTGTG TGGAGGGGAA CCAAGGAGAT GTAAACTGTG GTGTGAAAGG | | 1948 |

```
GTAGGAGAGA TGCTGGGGGT GGGGGTGCTT GTGTTTTACA CCCCCAATAT TATCCCAGTG      2008

TCCCCTGCCT TCCTTCTTCC CCTGCCCCAT GCCCCAATT  CTGTGGCGCA TCCAGCCGAA      2068

TTC                                                                    2071
```

( 2 ) INFORMATION FOR SEQ ID NO:16:

( i ) SEQUENCE CHARACTERISTICS:
        ( A ) LENGTH: 116 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met Ser Ala Thr Ala Ala Thr Val Pro Pro Ala Ala Pro Ala Gly Glu
 1           5                  10                 15

Gly Gly Pro Pro Ala Pro Pro Pro Asn Leu Thr Ser Asn Arg Arg Leu
            20                  25                 30

Gln Gln Thr Gln Ala Gln Val Asp Glu Val Val Asp Ile Met Arg Val
            35              40                 45

Asn Val Asp Lys Val Leu Glu Arg Asp Gln Lys Leu Ser Glu Leu Asp
    50                  55                 60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                110

Tyr Phe Ser Thr
        115
```

( 2 ) INFORMATION FOR SEQ ID NO:17:

( i ) SEQUENCE CHARACTERISTICS:
        ( A ) LENGTH: 2040 base pairs
        ( B ) TYPE: nucleic acid
        ( C ) STRANDEDNESS: double
        ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Mouse SNAP- 25 (GenBank M22012)

( i x ) FEATURE:
        ( A ) NAME/KEY: CDS
        ( B ) LOCATION: 164..784

( x i ) SEQUENCE DESCRIPTION: SEQ ID NO:17:

```
CCCGAGGTTT GGAGCTGTCT TTCCTTCCCT CCCTACCCGG CGGCTCCTCC ACTCTTGCTA      60

CCTGCAGGGA TCAGCGGACA GCATCCTCTG AAGAAGACAA GGTTCCTTAA CTAAGCACCA     120

CTGACTTGCT GGCCCCGGCG CCCAGCAACC CCCACCACT ACC ATG GCC GAG GAC       175
                                              Met Ala Glu Asp
                                               1

GCA GAC ATG CGT AAT GAA CTG GAG GAG ATG CAG AGG AGG GCT GAC CAG       223
Ala Asp Met Arg Asn Glu Leu Glu Glu Met Gln Arg Arg Ala Asp Gln
  5               10                  15                  20

CTG GCT GAT GAG TCC CTG GAA AGC ACC CGT CGC ATG CTG CAG CTG GTC       271
```

```
         Leu Ala Asp Glu Ser Leu Glu Ser Thr Arg Arg Met Leu Gln Leu Val
                          25                  30                  35

GAA GAG AGT AAA GAT GCT GGC ATC AGG ACT TTG GTT ATG TTG GAT GAG              319
Glu Glu Ser Lys Asp Ala Gly Ile Arg Thr Leu Val Met Leu Asp Glu
            40                  45                  50

CAA GGC GAA CAA CTG GAA CGC ATT GAG GAA GGG ATG GAC CAA ATC AAT              367
Gln Gly Glu Gln Leu Glu Arg Ile Glu Glu Gly Met Asp Gln Ile Asn
            55                  60                  65

AAG GAT ATG AAA GAA GCA GAA AAG AAT TTG ACG GAC CTA GGA AAA TTC              415
Lys Asp Met Lys Glu Ala Glu Lys Asn Leu Thr Asp Leu Gly Lys Phe
        70                  75                  80

TGC GGG CTT TGT GTG TGT CCC TGT AAC AAG CTT AAA TCC AGT GAT GCT              463
Cys Gly Leu Cys Val Cys Pro Cys Asn Lys Leu Lys Ser Ser Asp Ala
    85                  90                  95                 100

TAC AAA AAA GCC TGG GGC AAT AAT CAG GAT GGA GTA GTG GCC AGC CAG              511
Tyr Lys Lys Ala Trp Gly Asn Asn Gln Asp Gly Val Val Ala Ser Gln
                   105                 110                 115

CCT GCC CGT GTG GTG GAT GAA CGG GAG CAG ATG GCC ATC AGT GGT GGC              559
Pro Ala Arg Val Val Asp Glu Arg Glu Gln Met Ala Ile Ser Gly Gly
                120                 125                 130

TTC ATC CGC AGG GTA ACA AAC GAT GCC CGG GAA AAT GAA ATG GAT GAA              607
Phe Ile Arg Arg Val Thr Asn Asp Ala Arg Glu Asn Glu Met Asp Glu
            135                 140                 145

AAC CTA GAG CAG GTG AGC GGC ATC ATC GGA AAC CTC CGT CAT ATG GCC              655
Asn Leu Glu Gln Val Ser Gly Ile Ile Gly Asn Leu Arg His Met Ala
        150                 155                 160

CTA GAC ATG GGC AAT GAG ATT GAC ACC CAG AAT CGC CAG ATT GAC AGG              703
Leu Asp Met Gly Asn Glu Ile Asp Thr Gln Asn Arg Gln Ile Asp Arg
165                 170                 175                 180

ATC ATG GAG AAG GCT GAC TCC AAC AAA ACC AGA ATT GAT GAA GCC AAC              751
Ile Met Glu Lys Ala Asp Ser Asn Lys Thr Arg Ile Asp Glu Ala Asn
                185                 190                 195

CAA CGT GCA ACA AAG ATG CTG GGA AGT GGT TAAATCTGCC GTTCTGCTGT                801
Gln Arg Ala Thr Lys Met Leu Gly Ser Gly
                200                 205

GCTGTCCTCC AATGTTGTTG GACAAGAGAG AAGAGAGCTC CTTCATGCTT CTCTCATGGT            861
ATTACCTAGT AAGACTTACA CACACACACA CACACACACA CACACACACA CACACACACA            921
CACACACACA GAGTAGTCAC CCCCATTGTA AATGTCTGTG TGGTTTGT.CA GCTTCCCAAT           981
GATACCATGT GTCTTTTGTT TTCTCCGGCT CTCTTTCTTT GCCAAGGTT  GTACATAGTG           1041
GTCATCTGGT GACTCTATTT CCTGACTTAA GAGTTCTTGG GTCTCTCTCT TTCTTTTCTC           1101
AGTGGCGTTT GCTGAATGAC AACAATTTAG GAATGCTCAA TGTACTGTTG ATTTTTCTCA           1161
ATACACAGTA TTGTTCTTGT AAAACTGTGA CTTACCACAG AGCTACTACC ACAGTCCTTT           1221
CTTAGGGTGT CAGGCTCTGA ATCTCTCCAA ATGTGCTCTC TTTGGTTCCT CAGTGCTATT           1281
CTTTGTCTTT ATGATTTCAT AATTAGACAA TGTGAAATTA CATAACAGGC ATTGCACTAA           1341
AAGTGATGTG ATTTATGCAT TTATGCATGA GAACTAAATA GACTTTTAGA TCCTACTTAA           1401
ACAAAAACTT CCATGACAGT AGCATACTGA CAAGAAAACA CACAACAAG  CAACAATAAC           1461
AAAGCAACAA CTACGCATGC TCAGCATTGG GACACTGTCA AGATTAAGTC ATACCAGCAA           1521
AACCTGCAGC TGTGTCACCT TCTTCTGTCA ACATACAGAC TGATCATAAT GATCCCTTCT           1581
TTACACACAC ACACACACAC ACACACACAC ACACACACAC AAATGGAATT TAACCAACTT           1641
CCCAGAATTG ATGAAGCAAA TATATGTTTG GCTGAAACTA TTGTAAATGG GTGTAATATA           1701
GGGTTTGTCG AATGCTTTTG AAAGCTCTGT TTTCCAGACA ATACTCTTGT GTGGAAAACG           1761
TGAAGATCTT CTAAGTCTGG CTCTTGTGAT CACCAAACCC TGGTGCATCA GTACAACACT           1821
```

```
TTGCGCTAAT CTAGAGCTAT GCACAACCAA ATTGCTGAGA TGTTTAGTAG CTGATAAAGA    1881

AACCTTTAAA AAATTATATA AATGAATGAA ATATAGATAA ACTGTGAGAT AAATATCATT    1941

ACAGCATGTA TATTAAATCC CTCCTGTCTC CTCTGTTGGT TTGTGAAGTG ATTTGACATT    2001

TTGTAGCTAG TTTAAAATTA TTAAAAATTA TAGATGTTA                            2040
```

( 2 ) INFORMATION FOR SEQ ID NO:18:

( i ) SEQUENCE CHARACTERISTICS:
        ( A ) LENGTH: 206 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met Ala Glu Asp Ala Asp Met Arg Asn Glu Leu Glu Glu Met Gln Arg
  1               5                  10                  15

Arg Ala Asp Gln Leu Ala Asp Glu Ser Leu Glu Ser Thr Arg Arg Met
             20                  25                  30

Leu Gln Leu Val Glu Glu Ser Lys Asp Ala Gly Ile Arg Thr Leu Val
         35                  40                  45

Met Leu Asp Glu Gln Gly Glu Gln Leu Glu Arg Ile Glu Glu Gly Met
     50                  55                  60

Asp Gln Ile Asn Lys Asp Met Lys Glu Ala Glu Lys Asn Leu Thr Asp
 65                  70                  75                  80

Leu Gly Lys Phe Cys Gly Leu Cys Val Cys Pro Cys Asn Lys Leu Lys
             85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
            195                 200                 205
```

( 2 ) INFORMATION FOR SEQ ID NO:19:

( i ) SEQUENCE CHARACTERISTICS:
        ( A ) LENGTH: 76 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( C ) INDIVIDUAL ISOLATE: amino acids 191-266 of Syn1A - H3 region ( x i ) SEQUENCE DESCRIPTION: SEQ ID NO:19:

```
Ala Leu Ser Glu Ile Glu Thr Arg His Ser Glu Ile Ile Lys Leu Glu
 1           5                  10                    15

Asn Ser Ile Arg Glu Leu His Asp Met Phe Met Asp Met Ala Met Leu
             20              25                  30

Val Glu Ser Gln Gly Glu Met Ile Asp Arg Ile Glu Tyr Asn Val Glu
         35              40                  45

His Ala Val Asp Tyr Val Glu Arg Ala Val Ser Asp Thr Lys Lys Ala
     50              55                  60

Val Lys Tyr Gln Ser Lys Ala Arg Arg Lys Lys Ile
 65              70                  75
```

(2) INFORMATION FOR SEQ ID NO:20:

(i) SEQUENCE CHARACTERISTICS:
      (A) LENGTH: 50 amino acids
      (B) TYPE: amino acid
      (C) STRANDEDNESS: single
      (D) TOPOLOGY: unknown (ii) MOLECULE TYPE: protein (iii) HYPOTHETICAL: NO (iv) ANTI-SENSE: NO (vi) ORIGINAL SOURCE:
      (C) INDIVIDUAL ISOLATE: amino acids 191-240 of Syn1A (xi) SEQUENCE DESCRIPTION: SEQ ID NO:20:

```
Ala Leu Ser Glu Ile Glu Thr Arg His Ser Glu Ile Ile Lys Leu Glu
 1           5                  10                    15

Asn Ser Ile Arg Glu Leu His Asp Met Phe Met Asp Met Ala Met Leu
             20              25                  30

Val Glu Ser Gln Gly Glu Met Ile Asp Arg Ile Glu Tyr Asn Val Glu
         35              40                  45

His Asp
 50
```

(2) INFORMATION FOR SEQ ID NO:21:

(i) SEQUENCE CHARACTERISTICS:
      (A) LENGTH: 31 amino acids
      (B) TYPE: amino acid
      (C) STRANDEDNESS: single
      (D) TOPOLOGY: unknown (ii) MOLECULE TYPE: protein (iii) HYPOTHETICAL: NO (iv) ANTI-SENSE: NO (vi) ORIGINAL SOURCE:
      (C) INDIVIDUAL ISOLATE: amino acids 191-221 of Syn1A (xi) SEQUENCE DESCRIPTION: SEQ ID NO:21:

```
Ala Leu Ser Glu Ile Glu Thr Arg His Ser Glu Ile Ile Lys Leu Glu
 1           5                  10                    15

Asn Ser Ile Arg Glu Leu His Asp Met Phe Met Asp Met Ala Asp
             20              25                  30
```

(2) INFORMATION FOR SEQ ID NO:22:

(i) SEQUENCE CHARACTERISTICS:
      (A) LENGTH: 790 base pairs
      (B) TYPE: nucleic acid ( C ) STRANDEDNESS: double
( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
( C ) INDIVIDUAL ISOLATE: Cytoplasmic domain of Rat syntaxin 1A ( i x ) FEATURE:
( A ) NAME/KEY: CDS
( B ) LOCATION: 2..790

( x i ) SEQUENCE DESCRIPTION: SEQ ID NO:22:

```
C CGA ACC CAG GAG CTC CGC ACG GCC AAG GAC AGC GAT GAC GAC GAT        46
  Arg Thr Gln Glu Leu Arg Thr Ala Lys Asp Ser Asp Asp Asp Asp
   1               5                  10                  15

GAT GTC ACT GTC ACT GTG GAC CGA GAC CGC TTC ATG GAT GAG TTC TTT      94
Asp Val Thr Val Thr Val Asp Arg Asp Arg Phe Met Asp Glu Phe Phe
             20                  25                  30

GAA CAG GTG GAA GAG ATC CGG GGC TTT ATT GAC AAG ATT GCT GAA AAC     142
Glu Gln Val Glu Glu Ile Arg Gly Phe Ile Asp Lys Ile Ala Glu Asn
         35                  40                  45

GTG GAG GAG GTG AAG AGG AAA CAC AGC GCC ATC CTG GCC TCC CCG AAC     190
Val Glu Glu Val Lys Arg Lys His Ser Ala Ile Leu Ala Ser Pro Asn
     50                  55                  60

CCC GAT GAG AAG ACC AAG GAG GAA CTG GAG GAG CTC ATG TCG GAC ATT     238
Pro Asp Glu Lys Thr Lys Glu Glu Leu Glu Glu Leu Met Ser Asp Ile
 65                  70                  75

AAG AAG ACA GCG AAC AAA GTT CGC TCC AAG CTA AAG AGC ATC GAG CAG     286
Lys Lys Thr Ala Asn Lys Val Arg Ser Lys Leu Lys Ser Ile Glu Gln
 80                  85                  90                  95

AGC ATC GAG CAG GAG GAA GGT CTG AAC CGC TCG TCG GCG GAC CTG AGG     334
Ser Ile Glu Gln Glu Glu Gly Leu Asn Arg Ser Ser Ala Asp Leu Arg
                100                 105                 110

ATC CGG AAG ACG CAG CAT TCC ACG CTG TCC CGA AAG TTT GTG GAG GTC     382
Ile Arg Lys Thr Gln His Ser Thr Leu Ser Arg Lys Phe Val Glu Val
            115                 120                 125

ATG TCC GAG TAC AAC GCC ACT CAG TCA GAC TAC CGA GAA CGC TGC AAA     430
Met Ser Glu Tyr Asn Ala Thr Gln Ser Asp Tyr Arg Glu Arg Cys Lys
        130                 135                 140

GGG CGC ATC CAG AGG CAG CTG GAG ATC ACT GGC CGG ACC ACG AGT         478
Gly Arg Ile Gln Arg Gln Leu Glu Ile Thr Gly Arg Thr Thr Thr Ser
    145                 150                 155

GAG GAG TTG GAA GAC ATG CTG GAG AGT GGG AAT CCC GCC ATC TTT GCC     526
Glu Glu Leu Glu Asp Met Leu Glu Ser Gly Asn Pro Ala Ile Phe Ala
160                 165                 170                 175

TCT GGG ATC ATC ATG GAC TCC AGC ATC TCG AAG CAG GCC CTC AGT GAG     574
Ser Gly Ile Ile Met Asp Ser Ser Ile Ser Lys Gln Ala Leu Ser Glu
                180                 185                 190

ATC GAG ACC AGG CAC AGT GAG ATC ATC AAG TTG GAG AAC AGC ATC CGG     622
Ile Glu Thr Arg His Ser Glu Ile Ile Lys Leu Glu Asn Ser Ile Arg
            195                 200                 205

GAG CTA CAC GAT ATG TTC ATG GAC ATG GCC ATG CTG GTG GAG AGC CAG     670
Glu Leu His Asp Met Phe Met Asp Met Ala Met Leu Val Glu Ser Gln
        210                 215                 220

GGG GAG ATG ATT GAC AGG ATC GAG TAC AAT GTG GAA CAC GCT GTG GAC     718
Gly Glu Met Ile Asp Arg Ile Glu Tyr Asn Val Glu His Ala Val Asp
    225                 230                 235

TAC GTG GAG AGG GCC GTG TCT GAC ACC AAG AAG GCC GTC AAG TAC CAG     766
Tyr Val Glu Arg Ala Val Ser Asp Thr Lys Lys Ala Val Lys Tyr Gln
```

```
                  240                         245                         250                         255
AGC   AAG   GCA   CGC   AGG   AAG   AAG   ATC                                                                                      790
Ser   Lys   Ala   Arg   Arg   Lys   Lys   Ile
                        260
```

( 2 ) INFORMATION FOR SEQ ID NO:23:

( i ) SEQUENCE CHARACTERISTICS:
        ( A ) LENGTH: 263 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
Arg   Thr   Gln   Glu   Leu   Arg   Thr   Ala   Lys   Asp   Ser   Asp   Asp   Asp   Asp
  1                       5                          10                          15

Val   Thr   Val   Thr   Val   Asp   Arg   Asp   Arg   Phe   Met   Asp   Glu   Phe   Glu
                   20                          25                          30

Gln   Val   Glu   Glu   Ile   Arg   Gly   Phe   Ile   Asp   Lys   Ile   Ala   Glu   Asn   Val
                   35                          40                          45

Glu   Glu   Val   Lys   Arg   Lys   His   Ser   Ala   Ile   Leu   Ala   Ser   Pro   Asn   Pro
        50                          55                          60

Asp   Glu   Lys   Thr   Lys   Glu   Glu   Leu   Glu   Glu   Leu   Met   Ser   Asp   Ile   Lys
 65                          70                          75                          80

Lys   Thr   Ala   Asn   Lys   Val   Arg   Ser   Lys   Leu   Lys   Ser   Ile   Glu   Gln   Ser
                         85                          90                          95

Ile   Glu   Gln   Glu   Glu   Gly   Leu   Asn   Arg   Ser   Ser   Ala   Asp   Leu   Arg   Ile
                  100                         105                         110

Arg   Lys   Thr   Gln   His   Ser   Thr   Leu   Ser   Arg   Lys   Phe   Val   Glu   Val   Met
             115                         120                         125

Ser   Glu   Tyr   Asn   Ala   Thr   Gln   Ser   Asp   Tyr   Arg   Glu   Arg   Cys   Lys   Gly
      130                         135                         140

Arg   Ile   Gln   Arg   Gln   Leu   Glu   Ile   Thr   Gly   Arg   Thr   Thr   Thr   Ser   Glu
145                         150                         155                         160

Glu   Leu   Glu   Asp   Met   Leu   Glu   Ser   Gly   Asn   Pro   Ala   Ile   Phe   Ala   Ser
                        165                         170                         175

Gly   Ile   Ile   Met   Asp   Ser   Ser   Ile   Ser   Lys   Gln   Ala   Leu   Ser   Glu   Ile
                  180                         185                         190

Glu   Thr   Arg   His   Ser   Glu   Ile   Ile   Lys   Leu   Glu   Asn   Ser   Ile   Arg   Glu
             195                         200                         205

Leu   His   Asp   Met   Phe   Met   Asp   Met   Ala   Met   Leu   Val   Glu   Ser   Gln   Gly
      210                         215                         220

Glu   Met   Ile   Asp   Arg   Ile   Glu   Tyr   Asn   Val   Glu   His   Ala   Val   Asp   Tyr
225                         230                         235                         240

Val   Glu   Arg   Ala   Val   Ser   Asp   Thr   Lys   Lys   Ala   Val   Lys   Tyr   Gln   Ser
                        245                         250                         255

Lys   Ala   Arg   Arg   Lys   Lys   Ile
                  260
```

( 2 ) INFORMATION FOR SEQ ID NO:24:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
    ( C ) INDIVIDUAL ISOLATE: fragment at the amino terminus of VAMP 2 used in SPR ( x i ) SEQUENCE DESCRIPTION: SEQ ID NO:24:

```
Gly 5,693,476

81

82

-continued ( i v ) ANTI-SENSE: NO ( v i ) ORIGINAL SOURCE:
      ( C ) INDIVIDUAL ISOLATE: oligonucleotide used for mutant M1

( x i ) SEQUENCE DESCRIPTION: SEQ ID NO:26:

GACCGCGCAC AGTGAGGCCA TCAAGTTGGA           30

( 2 ) INFORMATION FOR SEQ ID NO:27:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: oligonucleotide used for mutant M4

( x i ) SEQUENCE DESCRIPTION: SEQ ID NO:27:

GCTGGCGGAG AGCGCGGGGG AGATGATT           28

( 2 ) INFORMATION FOR SEQ ID NO:28:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: oligonucleotide used for mutant M6

( x i ) SEQUENCE DESCRIPTION: SEQ ID NO:28:

ACACGTTGTG GACTACGCGG AGAGGGCCG           29

( 2 ) INFORMATION FOR SEQ ID NO:29:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: oligonucleotide used for mutant M2

( x i ) SEQUENCE DESCRIPTION: SEQ ID NO:29:

TCAAGGCGGA GAACAGCGCC CGGGAGCTAC           30

( 2 ) INFORMATION FOR SEQ ID NO:30:

( i ) SEQUENCE CHARACTERISTICS:
        ( A ) LENGTH: 30 base pairs

83

-continued

84

( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: oligonucleotide used for mutant M3

( x i ) SEQUENCE DESCRIPTION: SEQ ID NO:30:

GGGAGGCACA CGATATGGCC ATGGACATGG          30

( 2 ) INFORMATION FOR SEQ ID NO:31:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: oligonucleotide used for mutant M5

( x i ) SEQUENCE DESCRIPTION: SEQ ID NO:31:

AGATGGCTGA CAGGGCCGAG TACAATG             27

( 2 ) INFORMATION FOR SEQ ID NO:32:

( i ) SEQUENCE CHARACTERISTICS:
        ( A ) LENGTH: 87 base pairs
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: pGEX-KG polylinker ( i x ) FEATURE:
        ( A ) NAME/KEY: CDS
        ( B ) LOCATION: 1..87

( x i ) SEQUENCE DESCRIPTION: SEQ ID NO:32:

CTG  GTT  CCG  CGT  GGA  TCC  CCG  GGA  ATT  TCC  GGT  GGT  GGT  GGT  GGA  ATT     48
Leu  Val  Pro  Arg  Gly  Ser  Pro  Gly  Ile  Ser  Gly  Gly  Gly  Gly  Gly  Ile
  1                   5                  10                          15

CTA  GAC  TCC  ATG  GGT  CGA  CTC  GAG  CTC  AAG  CTT  AAT  TCA                    87
Leu  Asp  Ser  Met  Gly  Arg  Leu  Glu  Leu  Lys  Leu  Asn  Ser
                20                  25

( 2 ) INFORMATION FOR SEQ ID NO:33:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: protein (xi) SEQUENCE DESCRIPTION: SEQ ID NO:33:

Leu Val Pro Arg Gly Ser Pro Gly Ile Ser Gly Gly Gly Gly Gly Ile
1               5                   10                  15

Leu Asp Ser Met Gly Arg Leu Glu Leu Lys Leu Asn Ser
            20              25

(2) INFORMATION FOR SEQ ID NO:34:

(i) SEQUENCE CHARACTERISTICS:
        (A) LENGTH: 12 base pairs
        (B) TYPE: nucleic acid
        (C) STRANDEDNESS: unknown
        (D) TOPOLOGY: unknown (ii) MOLECULE TYPE: DNA (iii) HYPOTHETICAL: NO (iv) ANTI-SENSE: NO (vi) ORIGINAL SOURCE:
        (C) INDIVIDUAL ISOLATE: sequence between RBSII and 6xHis regions of pQE-9

(xi) SEQUENCE DESCRIPTION: SEQ ID NO:34:

ATGAGAGGAT CG          12

(2) INFORMATION FOR SEQ ID NO:35:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (ii) MOLECULE TYPE: DNA (iii) HYPOTHETICAL: NO (iv) ANTI-SENSE: NO (vi) ORIGINAL SOURCE:
        (C) INDIVIDUAL ISOLATE: sequence between 6xHis and t0 regions of pQE-9

(xi) SEQUENCE DESCRIPTION: SEQ ID NO:35:

GGATCCGTCG ACCTGCAGCC AAGCTTAATT AGCTGAG    37

It is claimed:

1. A method of identifying a compound capable of affecting binding of a SNAP-25, α-SNAP, n-sec1 or VAMP syntaxin-binding protein (SBP) to syntaxin, comprising
contacting said SBP with a corresponding binding protein binding site (BPBS) from a region of syntaxin, in the presence and absence of a test compound,
measuring the effect of the test compound on the extent of binding between the SBP and the BPBS, and
identifying said compound as effective if its measured effect on the extent of binding is above a threshold level.

2. The method of claim 1, wherein said syntaxin is syntaxin 1A.

3. The method of claim 1, wherein said region corresponds to the region of syntaxin 1A defined by SEQ ID NO:19.

4. The method of claim 1, wherein said test compound is effective to inhibit binding between the SBP and the BPBS.

5. The method of claim 1, wherein said test compound is effective to displace the SBP from the BPBS.

6. The method of claim 1, wherein said contacting includes contacting an SBP that is immobilized on a solid support.

7. The method of claim 1, wherein said contacting includes contacting a BPBS that is immobilized on a solid support.

8. The method of claim 1, wherein said test compound is one of a plurality of small molecules in a small molecule combinatorial library.

9. The method of claim 1, wherein said test compound is one of a plurality of peptides in a peptide combinatorial library.

10. The method of claim 1, wherein said SBP is SNAP-25 and said BPBS corresponds to the SNAP-25 binding domain of syntaxin 1A.

11. The method of claim 10, wherein said BPBS has an amino acid sequence represented as SEQ ID NO:21.

12. The method of claim 1, wherein said SBP is SNAP and said BPBS corresponds to the α-SNAP binding domain of syntaxin 1A.

13. The method of claim 12, wherein said BPBS has an amino acid sequence represented as SEQ ID NO:20.

14. The method of claim 1, wherein said SBP is VAMP and said BPBS corresponds to the VAMP binding domain of syntaxin 1A.

15. The method of claim 14, wherein said BPBS has an amino acid sequence represented as SEQ ID NO:19.

* * * * *